(12) United States Patent
Sliman

(10) Patent No.: US 11,872,268 B2
(45) Date of Patent: *Jan. 16, 2024

(54) SAFE AND EFFECTIVE BETA-LACTAMASE DOSING FOR MICROBIOME PROTECTION

(71) Applicant: Theriva Biologics, Inc., Rockville, MD (US)

(72) Inventor: Joseph Sliman, Rockville, MD (US)

(73) Assignee: Theriva Biologics, Inc., Rockville, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 17/572,055

(22) Filed: Jan. 10, 2022

(65) Prior Publication Data

US 2022/0125895 A1 Apr. 28, 2022

Related U.S. Application Data

(63) Continuation of application No. 16/892,647, filed on Jun. 4, 2020, now Pat. No. 11,253,577, which is a continuation of application No. 15/062,559, filed on Mar. 7, 2016, now Pat. No. 10,709,773.

(60) Provisional application No. 62/260,979, filed on Nov. 30, 2015, provisional application No. 62/167,006, filed on May 27, 2015, provisional application No. 62/129,199, filed on Mar. 6, 2015.

(51) Int. Cl.
| | |
|---|---|
| *A61K 38/50* | (2006.01) |
| *A61K 31/546* | (2006.01) |
| *A61K 45/06* | (2006.01) |
| *A61K 9/50* | (2006.01) |

(52) U.S. Cl.
CPC ............ *A61K 38/50* (2013.01); *A61K 9/5026* (2013.01); *A61K 9/5078* (2013.01); *A61K 31/546* (2013.01); *A61K 45/06* (2013.01); *C12Y 305/02006* (2013.01)

(58) Field of Classification Search
CPC .... A61K 38/50; A61K 9/5026; A61K 9/5078; A61K 31/546; A61K 45/06; C12Y 305/02006
See application file for complete search history.

(56) References Cited

U.S. PATENT DOCUMENTS

| | | | |
|---|---|---|---|
| 2,890,986 A | 6/1959 | Kraut et al. | |
| 2,941,995 A | 6/1960 | Doyle et al. | |
| 2,982,696 A | 5/1961 | Puetzer et al. | |
| 3,070,511 A | 12/1962 | Weitnauer | |
| 3,150,059 A | 9/1964 | Kleinschmidt et al. | |
| 3,239,394 A | 3/1966 | Walton | |
| 3,488,729 A | 1/1970 | Chauvette et al. | |
| 3,499,909 A | 3/1970 | Weissenburger et al. | |
| 5,607,671 A | 3/1997 | Heino | |
| 7,319,030 B2 | 1/2008 | Koski et al. | |
| 7,745,193 B2 | 6/2010 | Giannotta et al. | |
| 7,989,192 B2 | 8/2011 | Kaariainen et al. | |
| 8,894,994 B2 | 11/2014 | Koski et al. | |
| 2004/0248279 A1 | 12/2004 | Sawada et al. | |
| 2005/0158843 A1 | 7/2005 | Koski et al. | |
| 2005/0249716 A1 | 11/2005 | Bourgeois et al. | |
| 2009/0181004 A1 | 7/2009 | Kaariainen et al. | |
| 2009/0311234 A1 | 12/2009 | Koski et al. | |
| 2013/0216622 A1 | 8/2013 | Koski et al. | |
| 2016/0193307 A1 | 7/2016 | Kaleko et al. | |

FOREIGN PATENT DOCUMENTS

| | | |
|---|---|---|
| EP | 0384559 A1 | 8/1990 |
| EP | 0420600 A2 | 4/1991 |
| EP | 0420600 A3 | 11/1992 |
| EP | 1564286 A1 | 8/2005 |
| FI | 59265 B | 3/1981 |
| FI | 880017 A | 7/1988 |
| GB | 1241844 A | 8/1971 |
| GB | 1463513 A | 2/1977 |
| GB | 2199582 A | 7/1988 |
| WO | 1988/07865 A1 | 10/1988 |
| WO | 1993/13795 A1 | 7/1993 |
| WO | 1997/03185 A1 | 1/1997 |
| WO | 2003/040352 A1 | 5/2003 |
| WO | 2004/016248 A2 | 2/2004 |
| WO | 2005/078075 A2 | 8/2005 |
| WO | 2006/122835 A1 | 11/2006 |
| WO | 2007/147945 A1 | 12/2007 |
| WO | 2008/065247 A1 | 6/2008 |
| WO | 2011/148041 A1 | 12/2011 |
| WO | 2016/057744 A1 | 4/2016 |

OTHER PUBLICATIONS

Katz, "Probiotics for the Prevention of Antibiotic-associated Diarrhea and Clostridium difficile Diarrhea," J. Clin. Gastroenterol., Mar. 2006, vol. 40, No. 3, pp. 249-255.
Kim and Buyn, "Purification and properties of ampicillin acylase from Pseudomonas melanogenum," (1990) Biochim Biophys Acta 1040, 12-18.
Kim et al., "Construction of spore mutants of Bacillus subtilis for the development as a host for foreign protein production," Biotechnology Letters 23:999-1004 (2001).
Kisselev L., "Polypeptide release factors in prokaryotes and eukaryotes: same function, different structure," Structure, 2002, vol. 10: 8-9.
Knox and Moews, "β-Lactamase of Bacillus licheniformis 749/C: Refinement at 2 Å Resolution and Analysis of Hydration," J. Mol. Bioi., 1991, 220, pp. 435-455.
Knox, "Extended-spectrum and inhibitor-resistant TEM-Type β-lactamases: Mutations, Specificity, and Three-Dimensional Structure," Antimicrob. Agents Chemother., 1995, 39, 2593-2601.
Korhonen et al., "Milk Immunoglobulins and Complement Factors," British Journal of Nutrition, 2000, 84 Suppl 1, pp. S75-S80.
Kropp et al., "Metabolism of Thienamycin and Related Carbapenem Antibiotics by the Renal Dipeptidase, Dehydropeptidase-I," (1982) Antimicrob Agents Chemother 22, 62-70.

(Continued)

*Primary Examiner* — Paul J Holland
(74) *Attorney, Agent, or Firm* — Morgan, Lewis & Bockius LLP

(57) ABSTRACT

The present invention relates to, inter alia, safe and effective doses of a beta-lactamase for, e.g. microbiome protection.

8 Claims, 24 Drawing Sheets

Specification includes a Sequence Listing.

(56) References Cited

OTHER PUBLICATIONS

Kumakura et al., "Metabolic Fate of Clavulanic Acid and BRL 28500 in the Rat and Dog," Chemotherapy (Tokyo), 1986, 34 Suppl 4, pp. 187-201.
Lambert et al., "Susceptibility of Campylobacter pyloridis to 20 antimicrobial agents," (1986) Antimicrob Agents Chemother 30, (210): 510-511.
Li et al., "Bottlenecks in the expression and secretion of heterologous proteins in Bacillus subtilis," Res. Microbiol. 155:605-610 (2004).
Lim et al., "Cloning, Nucleotide Sequence, and Expression of the Bacillus cereus 5/B/6 β-Lactamase II Structural Gene," J. Bacteriol. 170:2873-2878 (1988).
Madan, "Methods of preparing microcapsules: interfacial polymerization," (1978) Pharm Technol 2, 68-75.
Madgwick and Waley, "β-Lactamase I from Bacillus cereus," Biochem. J. 248(3):657-662 (1987).
Madonna et al., "Nucleotide sequence of the β-lactamase I gene of Bacillus cereus strains 569/H and 5/B," Nucl. Acids Res. 15(4):1877 (1987).
Mandell and Sande, "Chapter 46. Antimicrobial Agents," (1990) In: Goodman and Gilman's, The Pharmacological Basis of Therapeutics, 8th Edition. New York: Pergamon Press, 1065-1097.
Marciano et al., "Analysis of the plasticity of location of the Arg244 positive charge within the active site of the TEM-1 β-lactamase," Prot. Sci. 18:2080-2089 (2009).
Marmur, "A Procedure for the Isolation of Deoxyribonucleic Acid from Micro-organisms," J. Mol. Biol. (1961) 3: 208-218.
Matagne et al., "Catalytic properties of class A β-lactamases: efficiency and diversity," Biochem. J. 330:581-598 (1998).
Matagne et al., "Ragged N-termini and other Variants of Class A β-Lactamases Analysed by Chromatofocusing," Biochem. J., 1991, 273, pp. 503-510.
Mentula et al., "Inhibition of ampicillin-induced emergence of resistance in intestinal coliforms by targeted recombinant β-lactamase," International Journal of Antimicrobial Agents, (2004)24:555-561.
Mezes, et al., "Construction of penP delta 1, Bacillus licheniformis 749/C β-Lactamase Lacking Site for Lipoprotein Modification," The Journal of Biological Chemistry, 1993, vol. 258, No. 18, pp. 11211-11218.
O'Callaghan et al., "Novel Method for Detection of β-Lactamases by Using a Chromogenic Cephalosporin Substrate," Antimicrobial Agents and Chemotherapy, Apr. 1972, vol. 1, No. 4, pp. 283-288.
Pedraza-Reyes et al., "Temporal Regulation and Forespore-Specific Expression of the Spore Photoproduct Lyase Gene by Sigma-G RNA Polymerase during Bacillus subtilis Sporulation," J. Bacteriol. 176(13): 3983-3991. 1994.
Perez-Llarena et al., "Structure-function studies of arginine at position 276 in CTX-M β-lactamases," J. Antimicrob. Chemother. 61(4):792-797 (2008).
Pitout, (Abstract) "IPSAT P1A, a class A beta-lactamase therapy for the prevention of penicillin-induced disruption to the intestinal microflora," Current Opinion in investigational drugs (London, England: 2000) 10.8 (2009): 838-844.
Pluckthun and Knowles, "The consequence of of stepwise deletions from the signal-processing site of β-lactamase," J. Biol Chem., 1987, vol. 262 (9): 3951-3957.
Rauws and Tytgat, "Cure of duodenal ulcer associated with eradication of Helicobacter pylori," (1990) Lancet 335, 1233-1235.
Rauws et al., "Campylobacter pyloridis-Associated Chronic Active Antral Gastritis," (1988) Gastroenterol 94, 33-40.
Rice et al., "β-Lactam Antibiotics and Gastrointestinal Colonization with Vancomycin-Resistant Enterococci," J. Infect. Dis., 2004, 189, pp. 1113-1118.
Sambrook and Russell. Molecular Cloning: A Laboratory Manual. "In vitro Amplification of DNA by the Polymerase Chain Reaction," vol. 2, Ch. 8, p. 8.1-8.126. 2001.
Sande et al., "Chapter 44. Antimicrobial Agents," (1990) In: Goodman and Gilman's, The Pharmacological Basis of Therapeutics, 8th Edition. New York: Pergamon Press, 1018-1046.
Santillana et al., "Crystal structure of the carbapenemase OXA-24 reveals insights into the mechanism of carbapenem hydrolysis," Proc. Natl. Acad. Sci. USA, 104:5354-5359 (2007).
Santos et al., "Folding of an Abridged β-Lactamase," Biochemistry, 2004, 43, pp. 1715-1723.
Saunders et al., "Use of Chromosomal Integration in the Establishment and Expression of blaZ, a Staphylococcus aureus β-lactamase Gene, in Bacillus subtilis," J. Bacteriol. 157(3): 718-726. 1984.
Saves et al., "The Asparagine to Aspartic Acid Substitution at Position 276 of TEM-35 and TEM-36 Is Involved in the β-Lactamase Resistance to Clavulanic Acid," J. Biol. Chem. 270:18240-18245 (1995).
Sawa et al., (Abstract) "The Effect of Cefixime on Bacterial Flora in the Intestinal Tracts of Healthy Male Volunteers," (1985) Chemotherapy (Tokyo) 33, Suppl. 6, 169-180.
Sen et al., "Developments in directed evolution for improving enzyme functions," Appl. Biochem. Biotechnol., Aug. 18, 2007, vol. 143: 212-223.
Shimooka et al, (Abstract) "Absorption, Distribution, and Excretion of Sulbactam and Ampilcillin after Intravenous Administration in Rats and Dogs," Chemotherapy (Tokyo), 1988, 36 Suppl 8, pp. 66-80.
Simm et al., "Characterization of Monomeric L1 Metallo-β-lactamase and the Role of the N-terminal Extension in Negative Cooperativity and Antibiotic Hydrolysis," The Journal of Biological Chemistry (Jul. 2002) vol. 277 No. 27: 24744-24752.
Sjolund et al., "Long-Term Persistence of Resistant Enterococcus Species after Antibiotics To Eradicate Helicobacter bylori," Ann. Intern. Med. 139:483-487 (2003).
Stiefel et al., "Oral Administration of β-Lactamase Preserves Colonization Resistance of Piperacillin-Treated Mice," J. Infect. Dis., 2003, 188, pp. 1605-1609.
Stiefel et al., "Orally Administered Recombinant Metallo-β-Lactamase Preserves Colonization Resistance of Piperacillin-Tazobactam-Treated Mice," Antimicrobial Agents and Chemotherapy, Dec. 2005, vol. 49, No. 12, pp. 5190-5191.
Stiefel, et al. "Gastrointestinal Colonization with a Cephalosporinase-Producing Bacteroides Species Preserves Colonization Resistance against Vancomycin-Resistant Enterococcus and Clostridium difficile in Cephalosporin-Treated Mice." Antimicrobial Agents and Chemotherapy, 2014, vol. 58, No. 8, pp. 4535-4542.
Sullivan et al., "Effect of Antimicrobial Agents on the Ecological Balance of Human Microflora," Lancet Infect. Dis., 2001, vol. 1, pp. 101-114.
Tarkkanen et al., "P1A Recombinant β-Lactamase Prevents Emergence of Antimicrobial Resistance in Gut Microflora of Healthy Subjects during Intravenous Administration of Ampicillin," Antimicrob. Agents Chemother. 53:2455-2462 (2009).
Therapeutic Drugs (1991), Dollery C, ed. Edinburgh: Churchill Livingstone, "Ceftriaxone (sodium)," c 127-c133.
Tranier et al., "The High Resolution Crystal Structure for Class A β-Lactamase PER-1 Reveals the Bases for Its Increase in Breadth of Activity," J. Biol. Chem. 275:28075-28082 (2000).
Walsh et al., "Metallo-β-Lactamases: the Quiet before the Storm?" Clinical Microbiology Reviews (Apr. 2005) vol. 18 No. 2: 306-325.
Walther-Rasmussen et al., "Terminal truncations in Amp C β-lactamase from a clinical isolate of Pseudomonas aeruginosa," Eur. J. Biochem. (1999) 263: 478-485.
Westphal et al., "Assessment of Biliary Excretion of Piperacilin-Tazobactam in Humans," Antimicrobial Agents and Chemotherapy, Aug. 1997, vol. 41, No. 8, pp. 1636-1640.
Whisstock et al., "Prediction of protein function from protein sequence," Q. Rev. Biophysics., 2003, vol. 36 (3): 307-340.
Wildfeuer et al., "Pharmacokinetics of Sulbactam and Ampicillin Intravenously Applied in Combination to Healthy Volunteers and Patients", Arzneimittel-Forschung, 1988, vol. 38, No. 11, pp. 1640-1643.
Wishart et al., "A single mutation converts a novel phosphotyrosine binding domain into a dual-specificity phosphatase," J. Biol. Chem., 1995, vol. 270(45): 26782-26785.
Witkowski et al., "Conversion of β-ketoacyl synthase to a Malonyl Decarboxylase by replacement of the active cysteine with glutamine," Biochemistry, 1999, vol. 38: 11643-11650.

(56) References Cited

OTHER PUBLICATIONS

Database UniProtKB/Swiss-Prot: P00808 (BLAC_BACLI), 1986.
Girlich et al., "Value of the Modified Hodge Test for Detection o Emerging Carbapenemases in Enterobacteriaceae", Journal of Clinical Microbiology, 2012, vol. 50, No. 2, pp. 477-479.
Gerrits et al., Helicobacter Ppylori and Antimicrobial Resistance: Molecular Mechanism and Clinical Implications. The Lancet Infectious Disease, 2006, vol. 6, pp. 699-709.
International Search Report PCT/US2016/019129, dated Jun. 30, 2016, 4 pages.
International Search Report PCT/US2016/021152, dated Jun. 30, 2016, 4 pages.
Patel et al., "Status Report on Carbapenemases: Challenges and Prospects", Expert review of Anti-Infective Therapy, 2011, vol. 9, No. 5, pp. 555-570.
Altschul et al., "Gapped BLAST and PSI-BLAST: A New Generation of Protein Database Search Programs," Nucleic Acids Research, 1997, vol. 25, No. 17, pp. 3389-3402.
Ambler et al., "A Standard Numbering Scheme for the Class A Beta-Lactamases," Biochem. J., 1991, 276, pp. 269-270.
Ambler, "the structure of β-lactamases," Phil. Trans. R. Soc. Lond. B 289: 321-331 (1980).
Bonnet, "Growing Group of Extended-Spectrum β-Lactamases: the CTX-M Enzymes," Antimicrob. Agents Chemother. 48(1):1-14 (2004).
Bonomo et al., "β-Lactamase mutations far from the active site influence inhibitor binding," Biochim. Biophys. Acta 1247:121-125 (1995).
Brogard et al., "Biliary Elimination of Ticarcillin Plus Clavulanic Acid (Ciaventin®)," Experimental and Clinical Study, International Journal of Clinical Pharmacology, Therapy and Toxicology, 1989, vol. 27, No. 3, pp. 135-144.
Broun et al., "Catalytic plasticity of fatty acid modification enzymes underlying chemical diversity of plant lipids," Science 1998, vol. 282: 1315-1317.
Bush et al., "A Functional Classification Scheme for β-Lactamases and Its Correlation with Molecular Structure," Antimicrobial Agents and Chemotherapy, Jun. 1995, vol. 39, No. 6, pp. 1211-1233.
Bush, "Metallo-β-Lactamases: A Class Apart," Clinical Infectious Diseases, 1998; 27(Suppl 1):S48-53.
Canica et al., "Phenotypic Study of Resistance of β-Lactamase-Inhibito-Resistant TEM Enzymes Which Differ by Naturally Occurring Variations and by Site-Directed Substitution at Asp276," Antimicrob. Agents Chemother. 42(6):1323-1328 (1998).
Carfi et al., "1.85 ÅResolution Structure of the Zinc II β-Lactamase from Bacillus cereus," Acta Cryst. (1998) D54: 313-323.
Carfi et al., "The 3-D structure of a zinc metallo-β-lactamase from Bacillus cereus reveals a new type of protein fold," The EMBO Journal, 1995, vol. 14 No. 20: 4914-4921.
Carfi et al., "X-ray Structure of the Zn11 β-Lactamase from Bacteroides fragilis in an Orthorhombic Crystal Form," Acta. Cryst. (1998) D54: 47-57.
Chambliss, "The forgotten dosage form: enteric coated tablets," (1983) Pharm Technol 7, 124-140.
Chen et al., "β-Lactamase Genes of the Penicillin-Susceptible Bacillus anthracis Sterne Strain," J. Bacteriol. 185 (3):823-830 (2003).
Chica et al., "Semi-rational approaches to engineering enzyme activity: combining the benefits of directed evolution and rational design," Curr. Opin. Biotechnol., 2005, vol. 16: 378-384.
Cole, "Hydrolysis of Penicillins and Related Compounds by the Cell-Bound Penicillin Acylase of *Escherichia coli*," (1969) Biochem. J. 115, 733-739.
Colombo et al., "The ybxl Gene of Bacillus Subtilis 168 Encodes a Class D β-Lactamase of Low Activity," Antimicrobial Agents and Chemotherapy, Feb. 2004, vol. 48, No. 2, pp. 484-490.
Concha et al., "Crystal Structure of the IMP-1 Metallo β-Lactamase from Pseudomonas aeruginosa and Its Complex with a Mercaptocarboxylate Inhibitor: Binding Determinants of a Potent, Broad-Spectrum Inhibitor," Biochemistry (2000) 39(15): 4288-4298.
Crawford, et al., "Over-expression, purification, and characterization of metallo-β-lactamase ImiS from Aeromonas veronii bv. sobria," Protein Expression and Purification 36 (2004) 272-279.
Davies and Abraham, "Separation, Purification and Properties of β-Lactamase I and β-Lactamase II from Bacillus cereus 569/H/9," (1974) Biochem. J. 143:115-127.
Delmas et al., "Structural Insights into Substrate Recognition and Product Expulsion in CTX-M Enzymes," J. Mol. Biol. 400:108-120 (2010).
Devos et al., "Practical limits of function prediction," Proteins: Structure, Function, and Genetics. 2000, vol. 41: 98-107.
Donskey, "Antibiotic Regimens and Intestinal Colonization with Antibiotic-Resistant Gram-Negative Bacilli," Clinical Infectious Diseases, 2006, 43 Suppl 2, pp. S62-S69.
Drawz et al., "The Role of a Second-Shell Residue in Modifying Substrate and Inhibitor Interactions in the SHV β-Lactamase: A Study of Ambler Position Asn276," Biochem. 48(21):4557-4566 (2009).
Drawz, et al., "Three Decades of β-Lactamase Inhibitors," Clin Microbiol Rev., 2010, vol. 23, No. 1, pp. 160-201.
Fey et al., Cetriaxone-Resistant *Salmonella* Infection Acquired by a Child from Cattle, New England J. Med., 2000, 342,1242-1249.
Fonze et al., "Crystal Structures of the Bacillus Licheniformis BS3 Class A β-Lactamase and of the Acyl-Enzyme Adduct Formed with Cefoxitin," Biochemistry, 2002, 41, 1877-1885.
Galleni et al., "Standard Numbering Scheme for Class B β-Lactamases," Antimicrobial Agents and Chemotherapy, Mar. 2001, vol. 45, No. 3, pp. 660-663.
Garau et al., "Update of the Standard Numbering Scheme for Class B β-Lactamases," Guest Commentary, Antimicrobial Agents and Chemotherapy, Jul. 2004, pp. 2347-2349, vol. 48, No. 7.
Garau et al., "A Metallo-β-lactamase Enzyme in Action: Crystal Structures of the Monozinc Carbapenemase CphA and its Complex with Biapenem," J. Mol. Biol. (2005) 345, 785-795.
Gazouli et al., "Effect of substitution of Asn for Arg-276 in the cefotaxime-hydrolyzing class A β-lactamase CTX-M-4," FEMS Microbiol. Lett. 168:289-293 (1998).
Gebhard et al., "Mapping the Distribution of Conformational Information Throughout a Protein Sequence," J. Mol. Biol., 2006, 358, pp. 280-288.
Giakkoupi et al., "Aspartic acid for asparagine substitution at position 276 reduces susceptibility to mechanism-based inhibitors in SHV-1 and SHV-5 β-lactamases," J. Antimicrobial. Chemother. 43:23-29 (1999).
Harmoinen et al., "Enzymic Degradation of a β-Lactam Antibiotic, Ampicillin, in the Gut: A Novel Treatment Modality," Journal of Antimicrobial Chemotherapy, 2003,51, pp. 361-365.
Harmoinen et al., "Orally Administered Targeted Recombinant Beta-Lactamase Prevents Ampicillin-Induced Selective Pressure on the Gut Microbiota: A Novel Approach to Reducing Antimicrobial Resistance," Antimicrobial Agents and Chemotherapy, Jan. 2004, vol. 48, No. 1, pp. 75-79.
Hata et al., "Substrate Deacylation Mechanisms of Serine-β-lactamases," Biol. Pharm. Bull. 29:2151-2159 (2006).
Herzberg, "Refined Crystal Structure of β-Lactamase from *Staphylococcus aureus* PC1 at 2.0 Å Resolution," J. Mol. Biol. 217:701-719 (1991).
Diggins et al., "In Vitro Activities of the β-Lactamase Inhibitors Clavulanic Acid, Sulbactam, and Tazobactam Alone or in Combination with β-Lactams against Epidemiologically Characterized Multidrug-Resistant Acinetobacter baumannii Strains," Antimicrobial Agents and Chemotherapy, May 2004, vol. 48, No. 5, pp. 1586-1592.
Hirschi A et al. (Abstract) "Campylobacter pylori, Gastritis and Ulcus pepticum," Wien. Klin. Wsch. 14:493-497 (1987).
Horton et al., "Engineering hybrid genes without the use of restriction enzymes: gene splicing by overlap extension," 1989, Gene 77:61-68 (1989).

(56) References Cited

OTHER PUBLICATIONS

Huber et al. "Chapter 2. Preparative Methods for 7-Aminocephalosporanic Acid and 6-Aminopenicillanic Acid," (1972) In: Flynn E, ed. Cephalosporins and Penicillins. New York: Academic Press, 27-73.

Hyman, "Anaphylactic Shock After Therapy With Penicillinase," (1959) JAMA 169, 593-594.

Illing et al., "Use of integrational plasmid excision to identify cellular localization of gene expression during sporulation in Bacillus subtilis," J. Bacteriol. 172(12):6937-6941 (1990).

Iserhard et al., "Epidemiology and Treatment of Gastric Campylobacter pylori Infection: more Questions than Answers," (1990) Hepato-Gastroenterol 37, 38-44.

International Search Report PCT/US2015/000228, dated Apr. 19, 2016, 6 pages.

Izui et al., "Large Exopenicillinase, Initial Extracellular Form Detected in Cultures of Bacillus licheniformis," Biochemistry, 1980, 19, pp. 1882-1886.

Jones et al., Cefoperazone: A Review of its Antimicrobial Spectrum, β-Lactamase Stability, Enzyme Inhibition, and Other in Vitro Characteristics, 1983, Rev. Infectious Disease 5 S108-S126.

Kaleko, et al., "SYN-004, a Class A β-Lactamase Therapy for the Prevention of Antibiotic-Induced Disruption of Intestinal Microflora", Open Forum Infect Dis, Oct. 9, 2014, I (suppl 1): SI15-SI16.

Kato et al., "Nucleotide Sequence of the β-Lactamase Gene of *Alkalophilic bacillus* sp. Strain 170," J. Gen. Microbiol. 131:3317-3324 (1985).

Freedberg DE, et al. The impact of proton pump inhibitors on the human gastrointestinal microbiome. Clin Lab Med. 2014;34(4):771-785(Sep. 24, 2014.).

FIG. 3

| Screening | Treatment Period 1 | | Run-in | Treatment Period 2 | | Phone Call | EOS Visit |
|---|---|---|---|---|---|---|---|
| | Check-in | SYN-004 + Ceftriaxone | | Check-in | Esomeprazole + SYN-004 + Ceftriaxone | | |
| Day -49 to -2 | Day -1 N = 20 | Day 1* | 5 to 7 days | Day -1 | Day 1** | 24 hr after discharge | 3-7 days after discharge |
| | <------ Confinement ------> | | <------ Esomeprazole ------> | <------ Confinement ------> | | | |

Treatments:

*Treatment Period 1* = 30-minute infusion of 1 g ceftriaxone beginning at approximately 8 AM, and 2 oral 150 mg doses of SYN-004 administered 0.5 hour prior to and 5.5 hours after the start of the infusion (approximately 7:30 AM and 1:30 PM, respectively).

Esomeprazole 40 mg delayed-release capsules QD during Run-in phase for 5 to 7 days prior to Period 2; dosing continues through the start of Day 1 in Treatment Period 2.

*Treatment Period 2* = Esomeprazole 40 mg delayed-release capsule administered 1.5 hours prior to start of infusion (approximately 6:30 AM), with a 30-minute infusion of 1 g ceftriaxone beginning at approximately 8 AM, and 2 oral 150 mg doses of SYN-004 administered 0.5 hour prior to and 5.5 hours after the start of the infusion (approximately 7:30 AM and 1:30 PM, respectively).

*Subjects will be released from clinical research unit (CRU) following completion of study procedures on Day 1 of Period 1 and return after completion of 5 to 7 days of run-in esomeprazole treatment on Day -1 of Treatment Period 2.

**Subjects will be discharged from CRU following completion of study procedures on Day 1 of Treatment Period 2 and return for the EOS Visit within 3 to 7 days.

Abbreviations: CRU = clinical research unit; EOS = end of study; QD = once daily

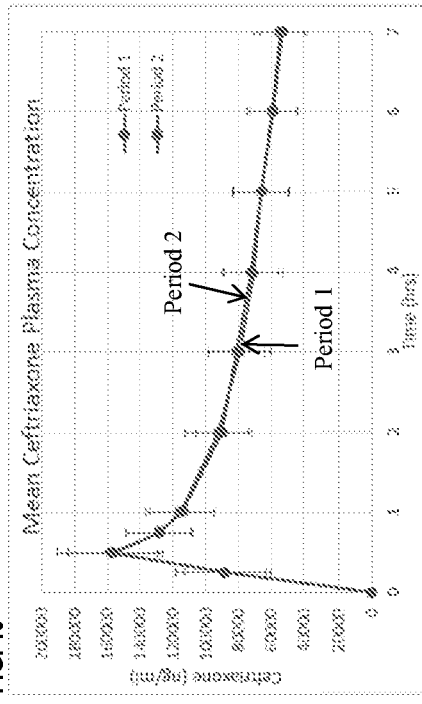
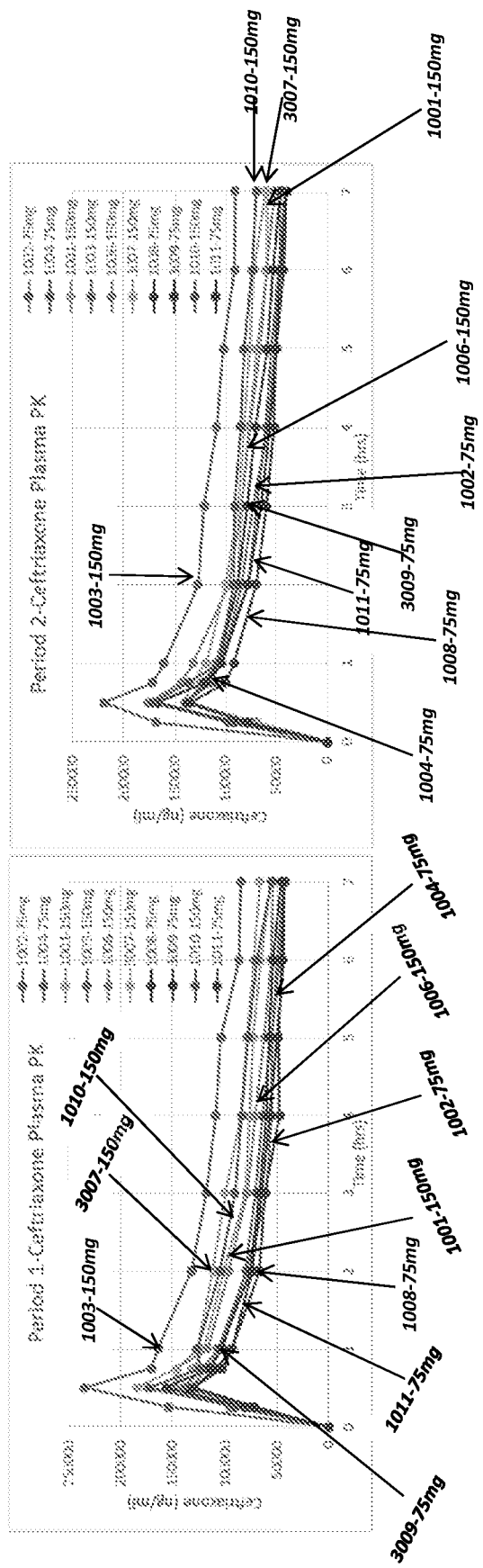
FIG. 10

C.

A.

B.

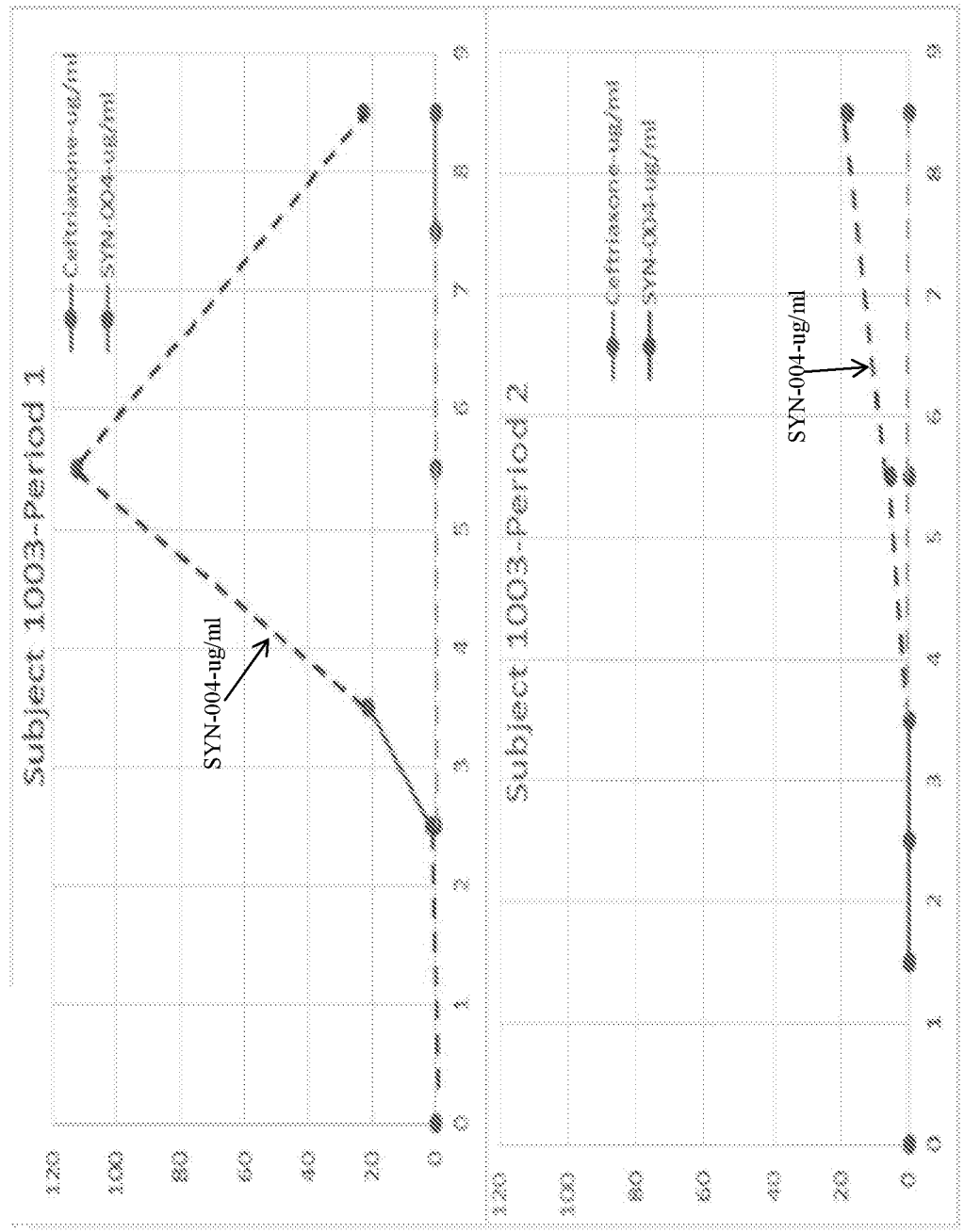
FIG. 13 (continued) C.

D.

E.

F.

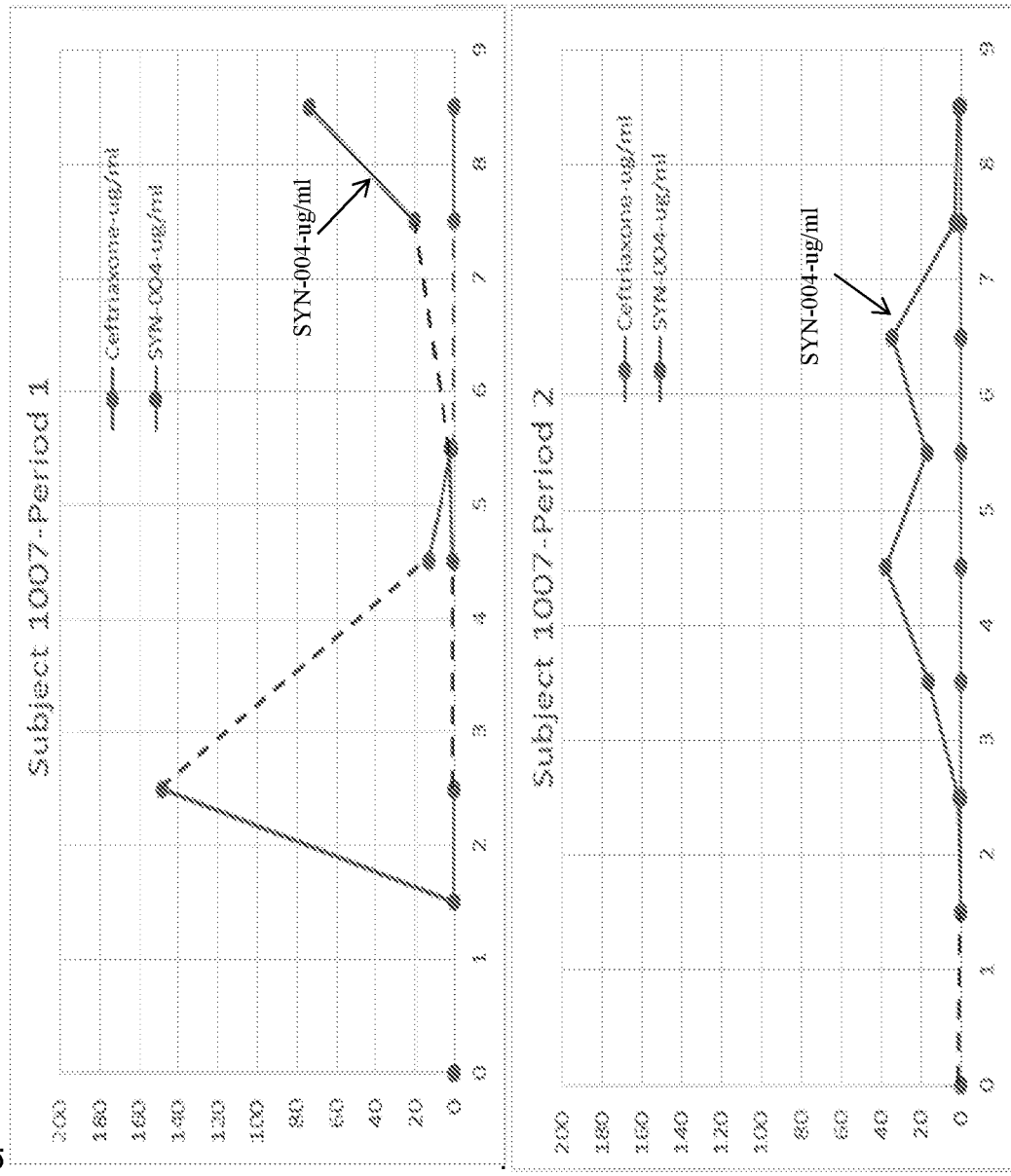
FIG. 13 (continued) G.

SAFE AND EFFECTIVE BETA-LACTAMASE DOSING FOR MICROBIOME PROTECTION

PRIORITY

This application is a continuation of U.S. patent application Ser. No. 16/892,647, filed Jun. 4, 2020 (now U.S. Pat. No. 11,253,577), which is a continuation of U.S. patent application Ser. No. 15/062,559, filed Mar. 7, 2016 (now U.S. Pat. No. 10,709,773), which claims the benefit of and priority to U.S. Provisional Patent Application Nos. 62/129,199, filed Mar. 6, 2015, 62/167,006, filed May 27, 2015, and 62/260,979, filed Nov. 30, 2015, the entire contents of all of which are incorporated by reference herein.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: SYN-12C2-SequenceListing.txt; date recorded: Jan. 10, 2022; file size: 3.96KB).

FIELD OF THE INVENTION

This invention relates, in part, to various compositions and methods for protecting the gastrointestinal microbiome from antibiotic disruption.

BACKGROUND

The gastrointestinal (GI) tract, which houses over one thousand distinct bacterial species and an estimated excess of $1 \times 10^{14}$ microorganisms, appears to be central in defining human host health status and a key part of the microbiome. Disruption of this microbiome is believed to be causative of a number of disorders.

Indeed, antibiotics, often a frontline therapy to prevent deleterious effects of microbes on human health can induce disruption in the microbiome, including in the GI tract, and lead to further disease. For instance, beta-lactam antibiotics are excreted in the bile into the gastrointestinal tract, and can damage the colonic microflora and lead to serious illnesses such as *Clostridium difficile* infection.

There remains a need for safe and effective doses and regimens of agents that prevent microbiome disruption by antibiotics while not reducing or eradicating the beneficial anti-infective effects of these antibiotics in a patient.

SUMMARY OF THE INVENTION

Accordingly, the present invention provides compositions and methods for protecting the gastrointestinal microbiome of a patient. In one aspect, the invention provides a method of protecting a patient's gastrointestinal microbiome, comprising administering an effective amount, of between about 1 mg to about 1,000 mg, of a pharmaceutical composition comprising a beta-lactamase, which comprises an amino acid sequence having at least 95% identity with SEQ ID NO: 1, to a patient in need thereof, including a patient who is undergoing treatment, or has recently undergone treatment, with a beta-lactam antibiotic, optionally selected from a penicillin and/or a cephalosporin.

In various embodiments, the bloodstream or plasma levels of beta-lactam antibiotic in the patient are not substantially reduced relative to an untreated patient. In various embodiments, the beta-lactamase is substantially absent from the bloodstream or plasma of the patient. In various embodiments, the beta-lactamase does not substantially interfere with blood or plasma levels of the antibiotic. In various embodiments, the beta-lactamase degrades or inactivates excess or residual antibiotic in the GI tract. In various embodiments, the beta-lactam antibiotic is degraded in the patient's intestinal chyme. In various embodiments, the beta-lactam antibiotic is degraded in the small intestines before the antibiotic reaches the colon. Accordingly, in various embodiments, the present doses allow for systemic antibiotic activity while sparing the GI tract microbiome from undesired systemic antibiotic.

In some embodiments, the beta-lactam antibiotic and beta-lactamase are administered simultaneously or sequentially. In some embodiments, the beta-lactam antibiotic is administered orally. In other embodiments, the beta-lactam antibiotic is administered parenterally, optionally selected from intravenously, intramuscularly and/or by infusion, while the beta-lactamase is administered orally.

In various embodiments, the present methods further comprise administering food to the patient. In various embodiments, the present methods further comprise administering an agent that modulates GI tract pH (e.g. a proton pump inhibitor).

In various embodiments, the protection of the patient's microbiome comprises treatment or prevention of a microbiome-mediated disorder, including, without limitation, antibiotic-induced adverse effects, *C. difficile* infection (CDI), *C. difficile*-associated disease, ulcerative colitis, Crohn's disease, irritable bowel syndrome and antibiotic-associated diarrhea. In various embodiments, the protection of the microbiome comprises treatment or prevention of microbiome mediated systemic or metabolic disorders including, without limitation, fatty liver disease, obesity, Parkinson's disease, autism, depression, and immune-mediated disorders (e.g., Lupus).

DESCRIPTION OF THE DRAWINGS

FIG. 3 shows a schematic of the study design employed in Example 6.

FIG. 10 shows ceftriaxone plasma concentrations from the Example 5 study. The top panel shows mean for all 10 subjects Period 1 (no SYN-004) vs. Period 2 (plus SYN-004) and the bottom panels show each subject individually.

Figure 11:
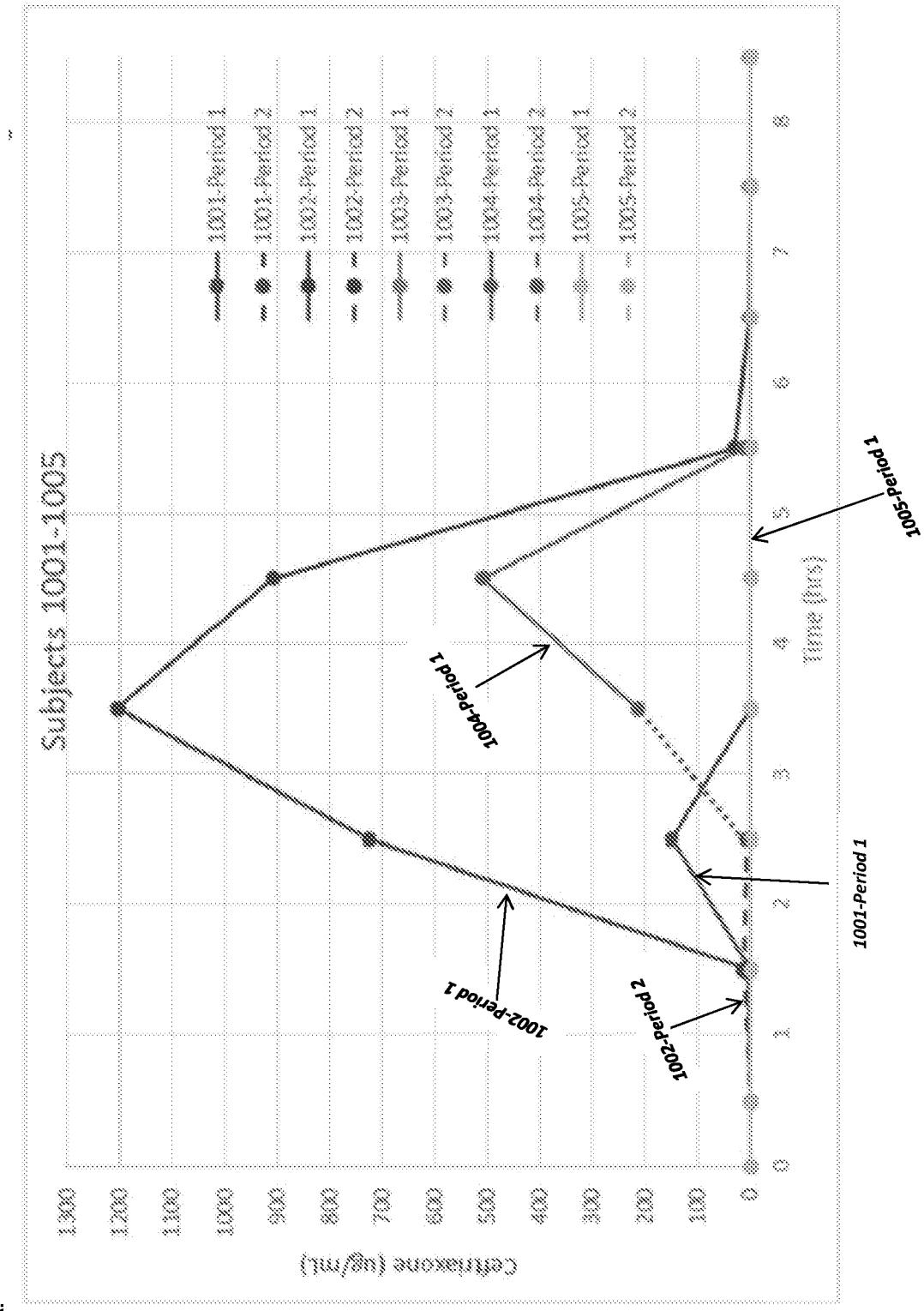
Figure 11:
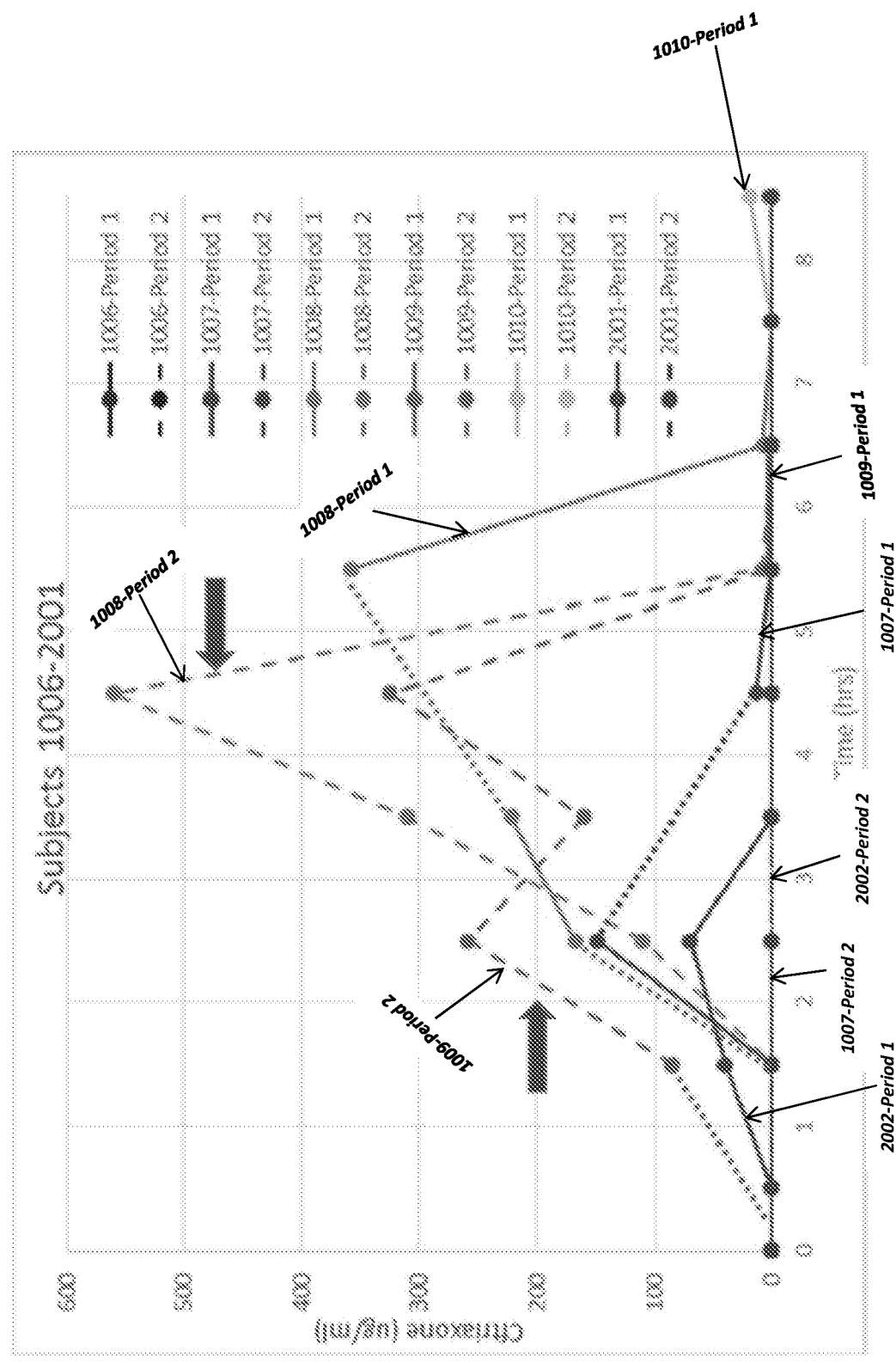
Figure 11:
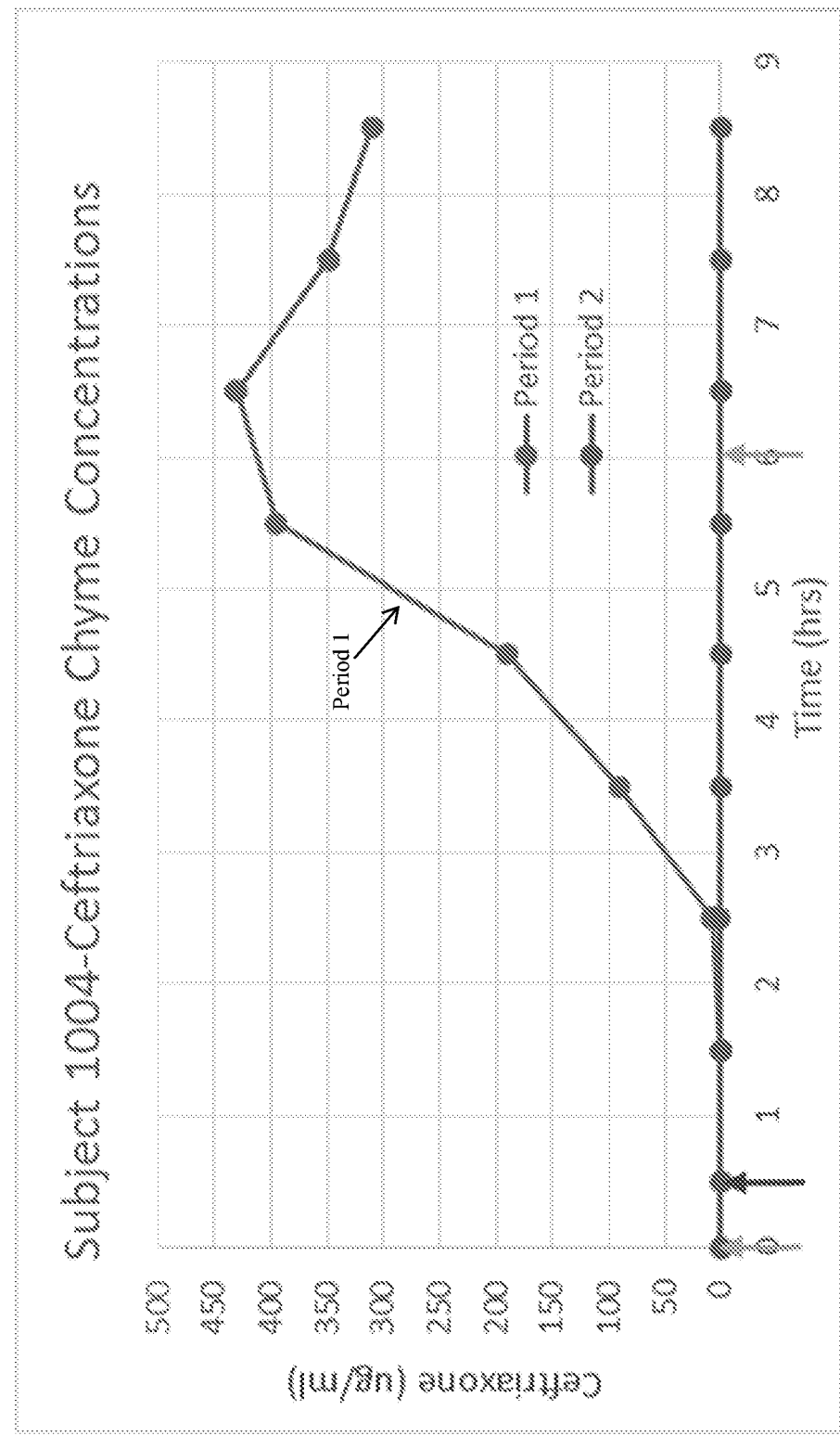

FIG. 11, panel A depicts the ceftriaxone levels of subjects 1001, 1002, 1003, 1004, and 1005 during Periods 1 and 2 as described in Example 6. Panel B depicts the ceftriaxone levels of subjects 1006, 1007, 1008, 1009, 1010, and 2001 during Periods 1 and 2. Panel C depicts the ceftriaxone levels of a subject (i.e., subject 1004) during Periods 1 and 2 as described in Example 6.

Figure 12:
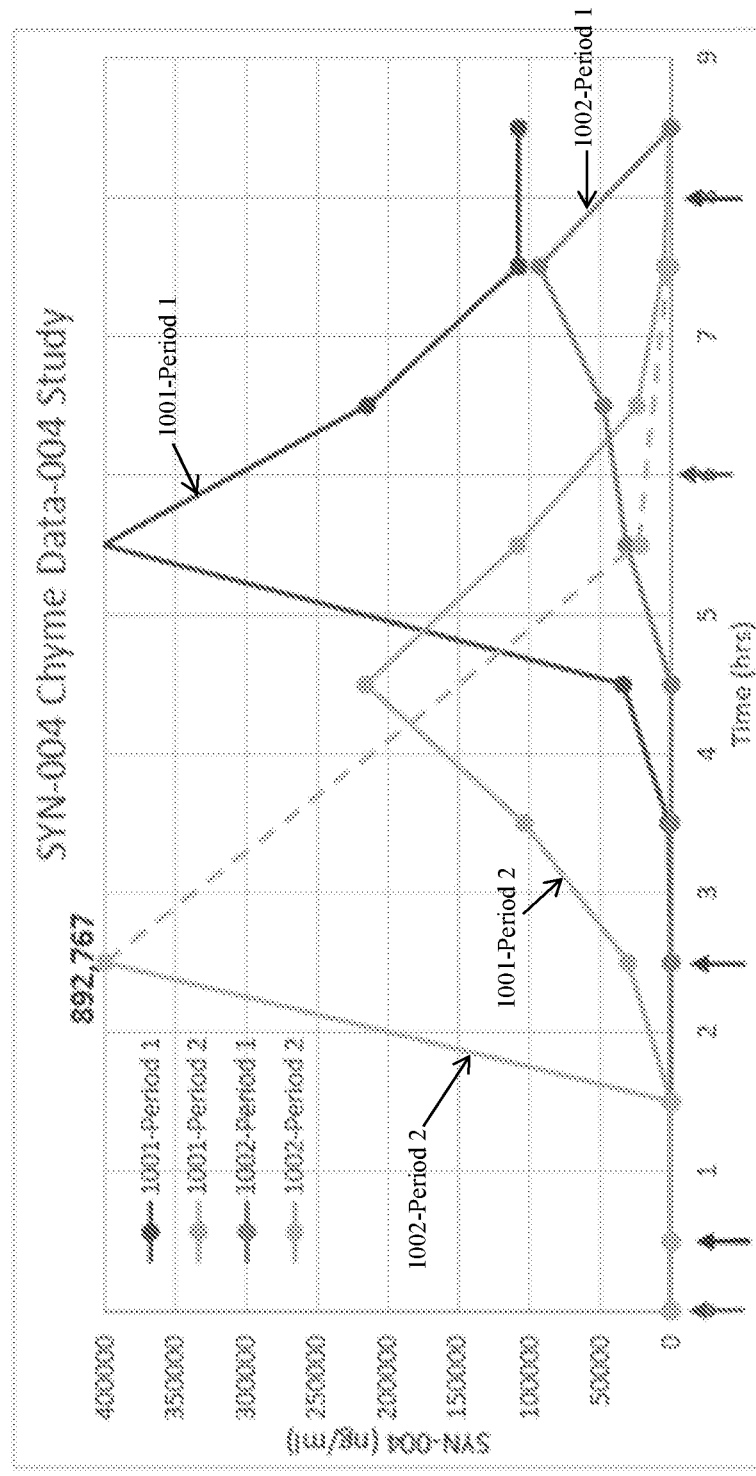
Figure 12:
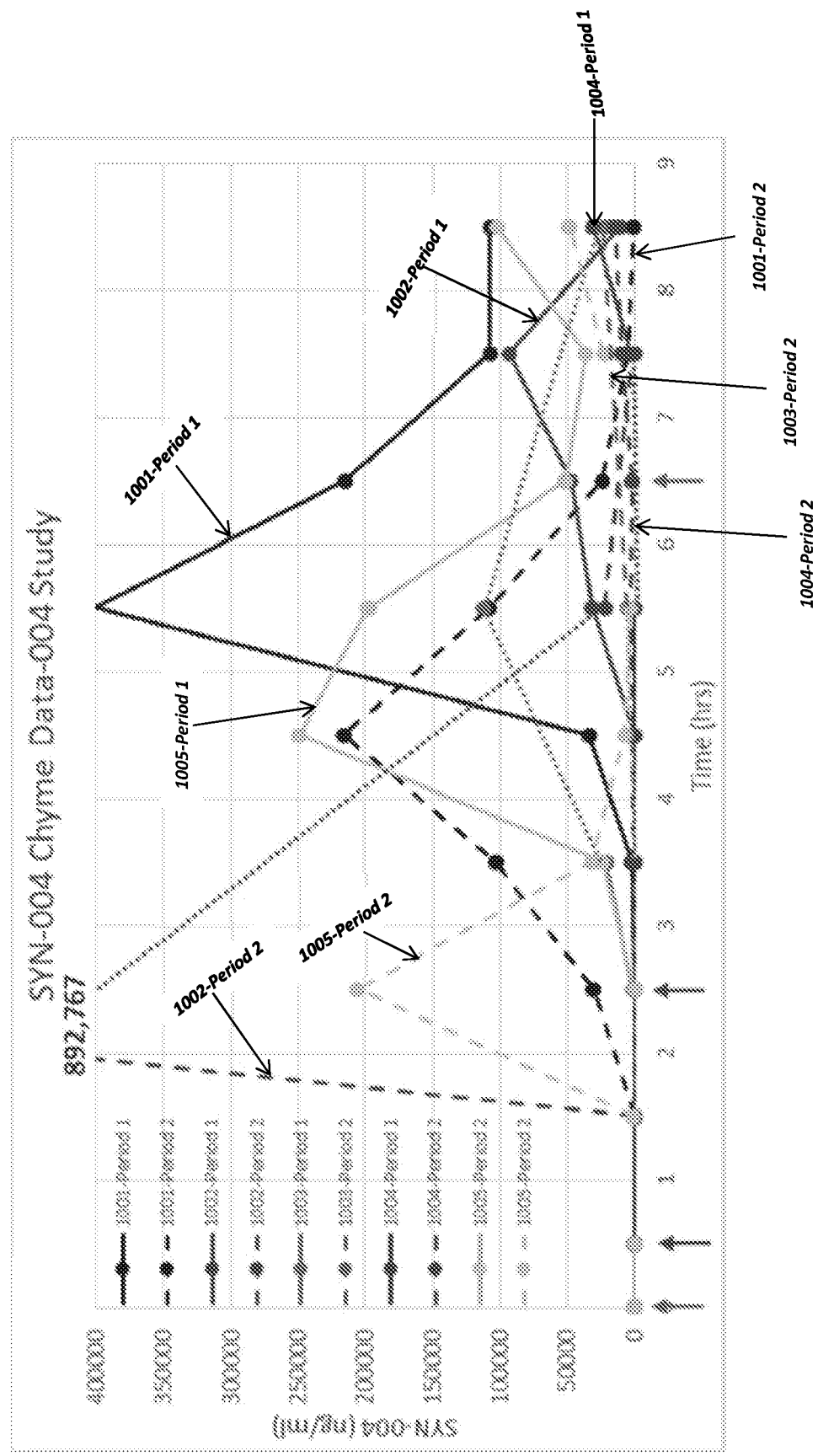

FIG. 12, panel A depicts the SYN-004 levels in the chyme of two subjects (i.e., subjects 1001 and 1002) during Periods 1 and 2 as described in Example 6. Panel B depicts the SYN-004 levels in the chyme of additional subjects (i.e., subjects 1001, 1002, 1003, 1004, and 1005) during Periods 1 and 2 as described in Example 6.

Figure 13:
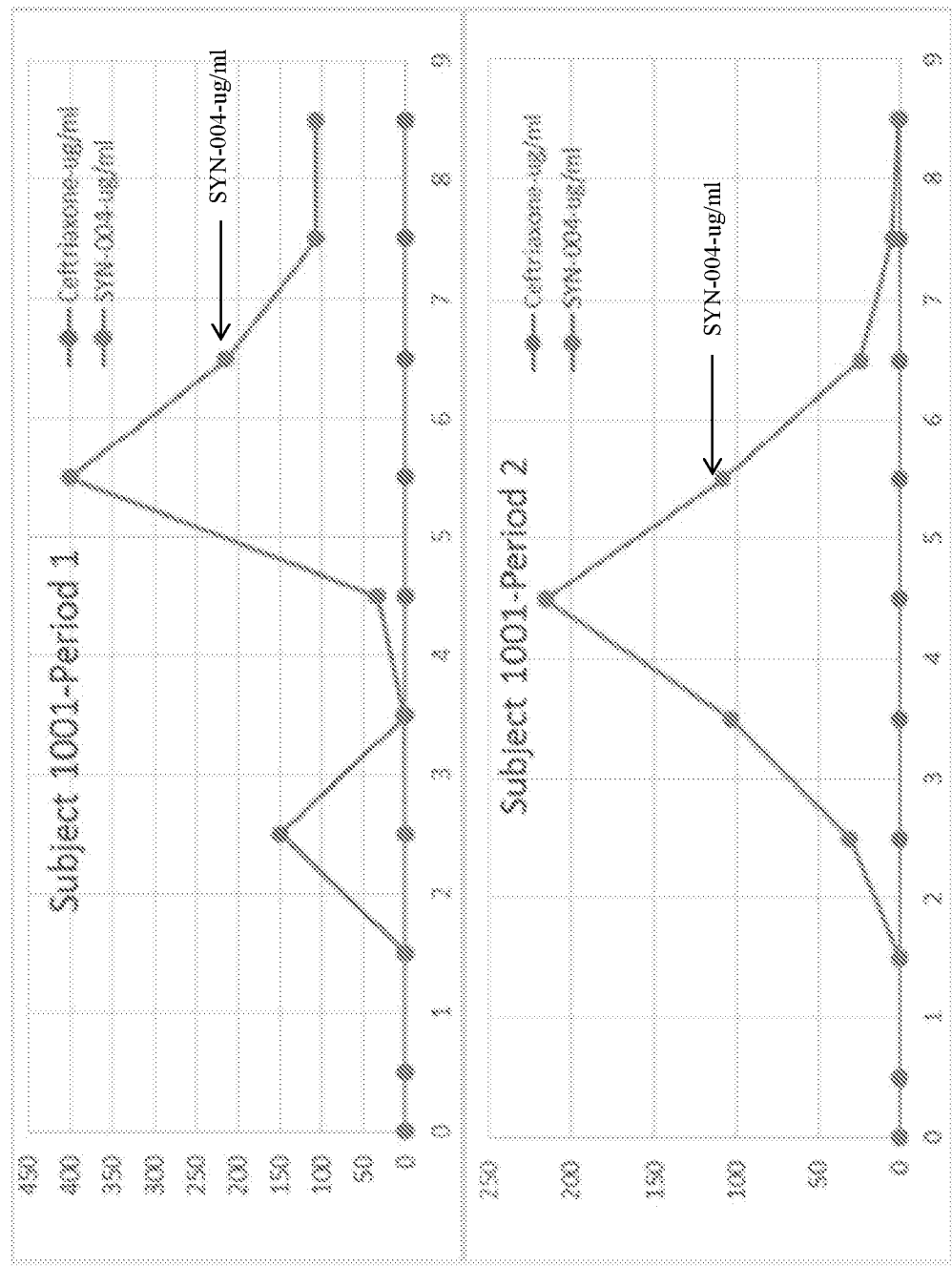
Figure 13:
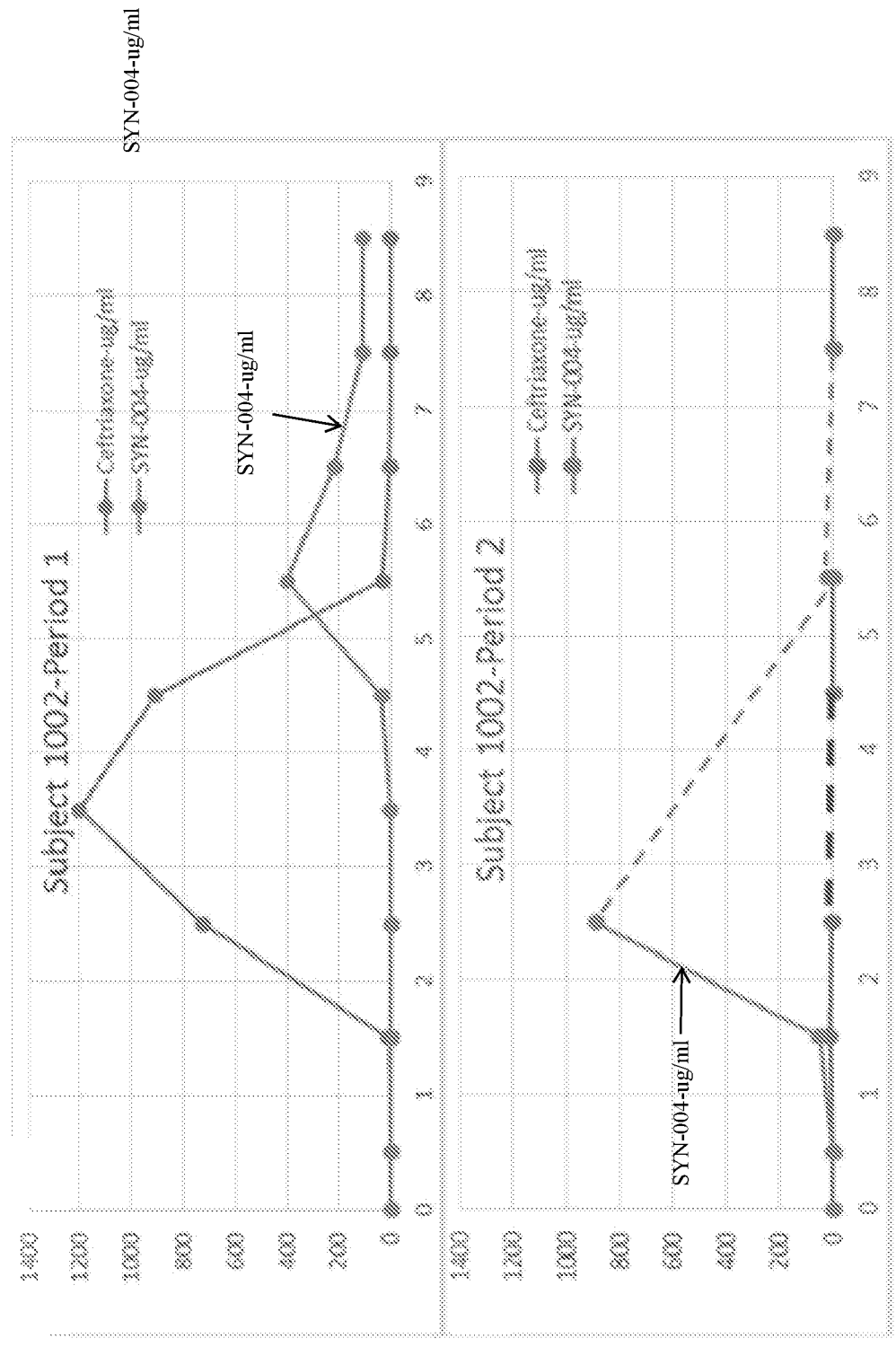
Figure 13:
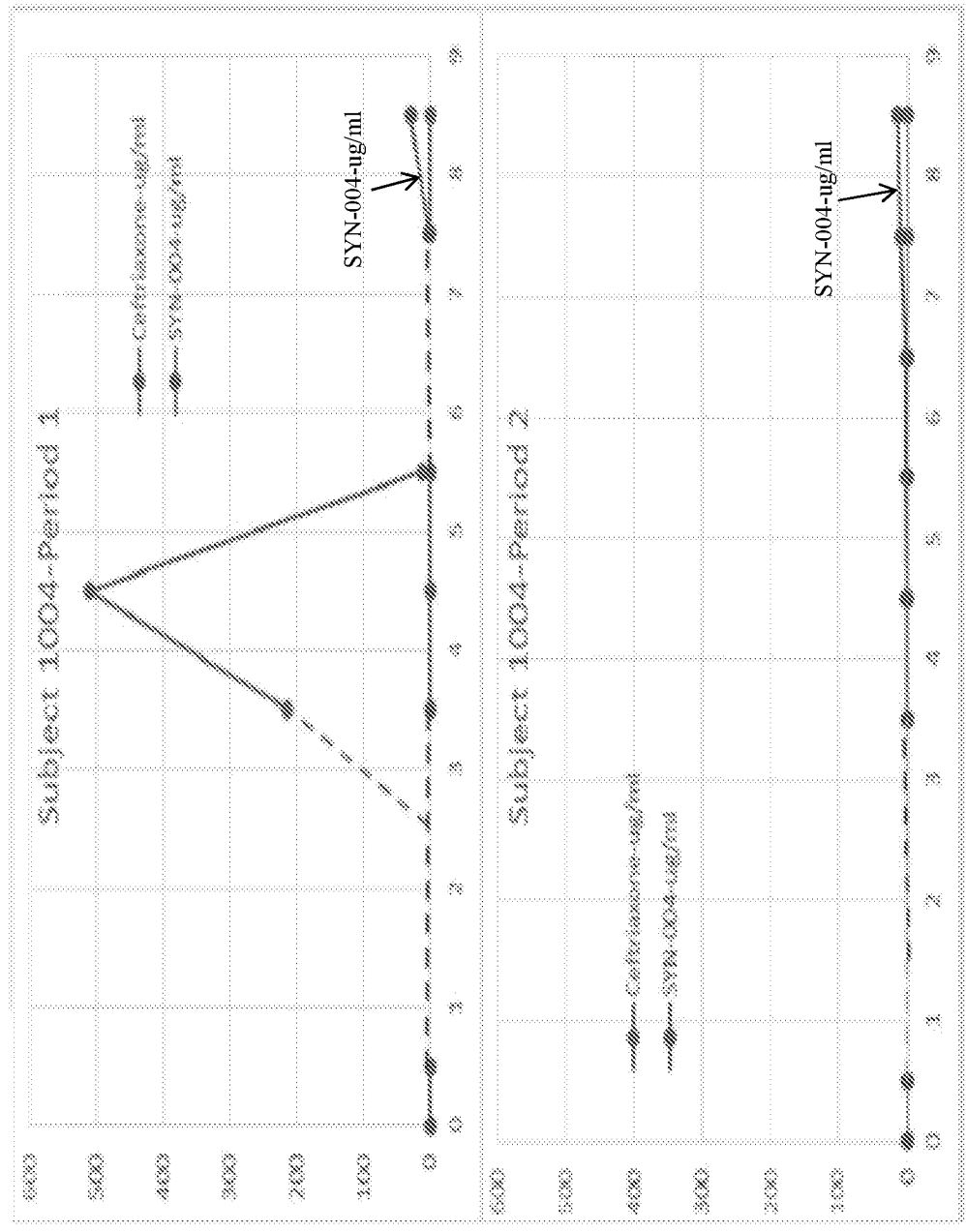
Figure 13:
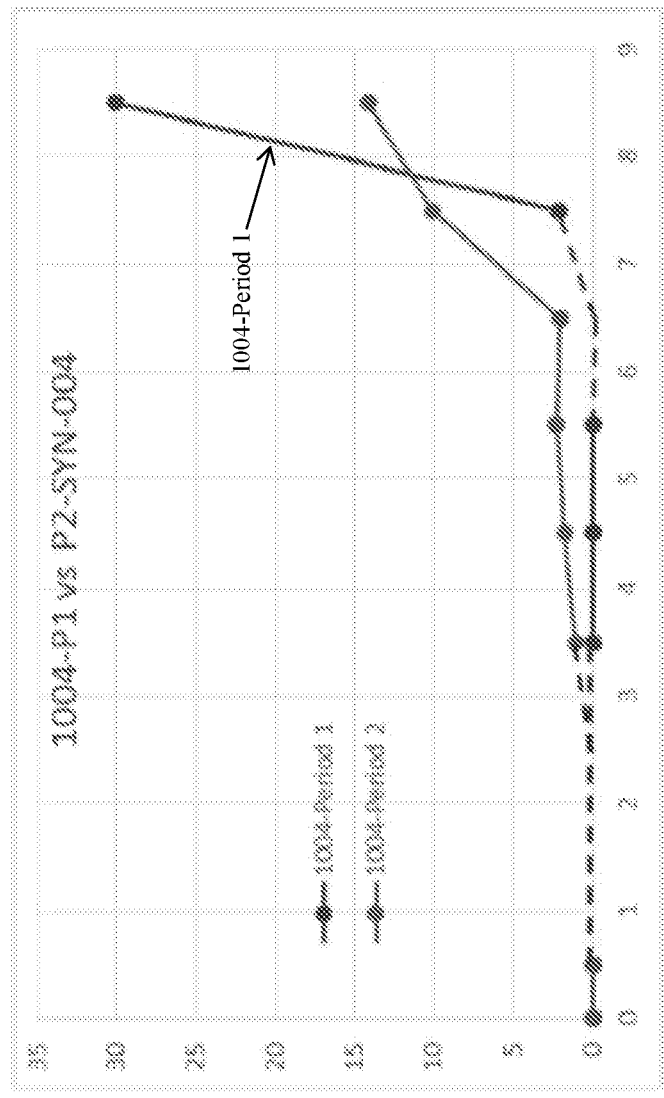
Figure 13:
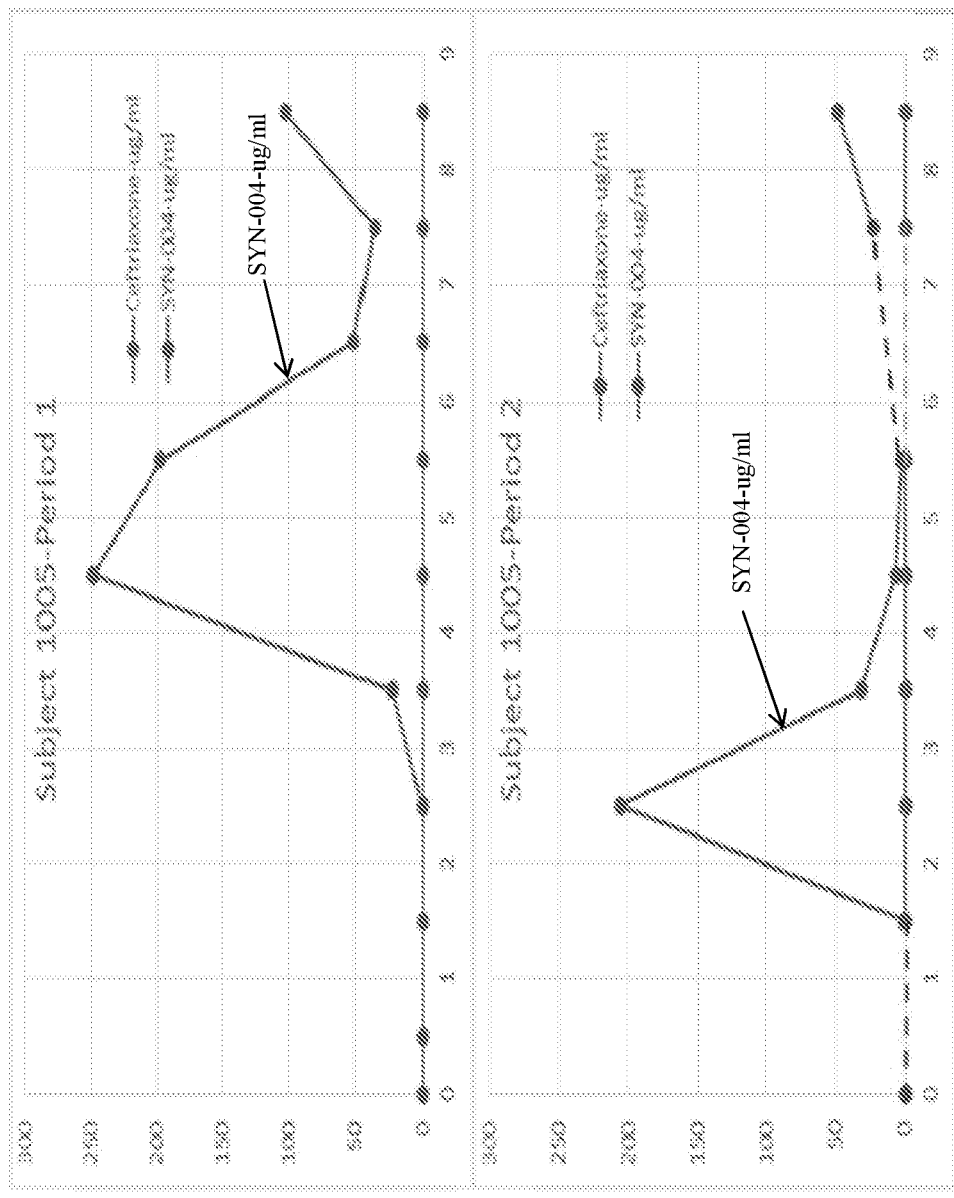

FIG. 13 provides overlays of the ceftriaxone levels and SYN-004 levels in the chyme of various subjects as described in Example 6. Panel A: subject 1001, Periods 1 and 2; Panel B: subject 1002, Periods 1 and 2; Panel C: subject 1003, Periods 1 and 2; Panel D: subject 1004, Periods 1 and 2; Panel E: subject 1004, overlay of SYN-004 levels during Periods 1 and 2; Panel F: subject 1005, Periods 1 and 2; and Panel G: subject 1007, Periods 1 and 2.

DETAILED DESCRIPTION

The present invention is based, in part, on the discovery of safe and effective doses of beta-lactamases which can protect the gastrointestinal microbiome of a patient who is undergoing treatment, or has undergone treatment, with an antibiotic. Administration of antibiotics often disrupts the ecological balance of normal intestinal microbiota due to residual or unabsorbed antibiotics remaining in the intestines or being excreted into the intestines (e.g., the small intestine and/or the large intestine). In various embodiments, the doses of beta-lactamase inactivate the unabsorbed antibiotics in the GI tract thereby restoring and/or maintaining the normal intestinal microbiota of a patient (e.g. a healthy balance (e.g. a healthy ratio and/or distribution)) and preventing any overgrowth of potentially pathogenic microorganisms that may disrupt the healthy state.

Beta-Lactamases

In various aspects, the beta-lactamase has the amino acid sequence of SEQ ID NO: 1 (i.e., "P3A" or "SYN-004" as described in WO 2011/148041, the entire contents of which are hereby incorporated by reference.). Mutations may be made to this sequence to generate beta-lactamase derivatives that may be utilized by methods of the invention.

SEQ ID NO: 1
TEMKDDFAKLEEQFDAKLGIFALDTGTNRTVAYRPDERFAFASTIKALTV

GVLLQQKSIEDLNQRITYTRDDLVNYNPITEKHVDTGMTLKELADASLRY

SDNAAQNLILKQIGGPESLKKELRKIGDEVTNPERFEPELNEVNPGETQD

TSTARALVTSLRAFALEDKLPSEKRELLIDWMKRNTTGDALIRAGVPDGW

EVADKTGAASYGTRNDIAIIWPPKGDPWLAVLSSRDKKDAKYDNKLIAEA

TKVVMKALNMNGK.

In some embodiments, SEQ ID NO: 1 may have a Met and/or Thr preceding the first residue of the sequence. In various embodiments, the Met may be cleaved. As described herein, mutations may be made to the sequence comprising the Met and/or Thr preceding the first residue to generate beta-lactamase derivatives. In some embodiments, the leading Thr may bring about increased stability of the enzyme relative to another leading amino acid (e.g. Lys). For example, such a residue may confer increased resistance to an amino peptidase.

Also provided herein is the nucleotide sequence of the P3A as SEQ ID NO: 2:

SEQ ID NO: 2
atgactgagatgaaagatgattttgcgaagctggaagaacagtttgacgc aaaattgggcattttcgcgttggacacgggtacgaatcgtacggttgcct accgtccggacgagcgcttcgccttcgcgagcacgatcaaagccctgacc gtcggcgtgctgctccagcaaaagagcatcgaggacctgaaccagcgcat tacctacaccgtgatgatctggtgaactataatccgatcaccgagaaac acgttgataccggtatgaccctgaaagaactggcagatgcaagcctgcgc tacagcgataacgcggctcagaatctgattctgaagcaaatcggtggtcc ggagagcttgaagaaagaactgcgtaaaatcggcgatgaagtcactaatc cggagcgttttgagccggagctgaacgaagtgaatccgggtgaaacgcaa gacacgagcaccgcgcgtgcgcttgtcacctccctgcgcgcttcgcact ggaagataagctgccgtcggagaaacgcgagctgctgatcgactggatga agcgcaatacgaccggcgacgcgctgattcgtgcgggcgttccggacggt tgggaagtggctgacaagaccggtgcggcgagctacggcacccgtaacga tatcgcgatcatttggccacctaaaggtgacccggtcgtgctggccgtac tgagcagccgtgacaagaaagacgcaaagtatgataacaagctgattgca gaggcgaccaaagttgttatgaaggcactgaacatgaatggtaag Further, the beta-lactamase polypeptide may include additional upstream residues from the first residue of SEQ ID NO: 1 (see, e.g., JBC 258 (18): 11211, 1983, the contents of which are hereby incorporated by reference-including the exo-large and exo-small versions of penP and penP1). Further, the beta-lactamase polypeptide may also include additional downstream residues from the last residue of SEQ ID NO: 1.

In some embodiments, the beta-lactamase includes one or more (e.g. about 1, or about 2, or about 3, or about 4, or about 5, or about 6, or about 7, or about 8, or about 9, or about 10) mutations relative to SEQ ID NO: 1 or SEQ ID NO: 2. In some embodiments the beta-lactamase includes a variant of P3A, i.e. a sequence with at least 95, 96, 97, 98, 99, 99.5, 99.8, 99.9% identity to SEQ ID NO: 1 or SEQ ID NO: 2. In various embodiments, one or more amino acid of SEQ ID NO: 1 is substituted with a naturally occurring amino acid, such as a hydrophilic amino acid (e.g. a polar and positively charged hydrophilic amino acid, such as arginine (R) or lysine (K); a polar and neutral of charge hydrophilic amino acid, such as asparagine (N), glutamine (Q), serine (S), threonine (T), proline (P), and cysteine (C), a polar and negatively charged hydrophilic amino acid, such as aspartate (D) or glutamate (E), or an aromatic, polar and positively charged hydrophilic amino acid, such as histidine (H)) or a hydrophobic amino acid (e.g. a hydrophobic, aliphatic amino acid such as glycine (G), alanine (A), leucine (L), isoleucine (I), methionine (M), or valine (V), a hydrophobic, aromatic amino acid, such as phenylalanine (F), tryptophan (W), or tyrosine (Y) or a non-classical amino acid (e.g. selenocysteine, pyrrolysine, N-formylmethionine β-alanine, GABA and δ-Aminolevulinic acid. 4-Aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β methyl amino acids, C α-methyl amino acids, N α-methyl amino acids, and amino acid analogs in general). In some embodiments, SEQ ID NO: 1 may have a Met and/or Thr preceding the first residue of the sequence. These residues may be similarly mutated as above.

In some embodiments, a leader sequence may be attached to either the N-terminus or C-terminus of the beta-lactamase polypeptide which may allow secretion of the polypeptide from the host organism or allow the polypeptide to be purified using affinity purification (e.g., a poly-histidine tag or another affinity purification target). The leader sequence may be attached directly to the polypeptide or through a linker sequence.

In all of these mutants, the numbering of residues corresponds to SEQ ID NO: 1. These residue numbers may be converted to Ambler numbers (Ambler et al., 1991, A standard numbering scheme for the Class A β-lactamases, *Biochem. J.* 276:269-272, the contents of which are hereby incorporated by reference) through use of any conventional bioinformatic method, for example by using BLAST (Basic Local Alignment Search Tools) or FASTA (FAST-All).

Dosing and Regimens

In various embodiments, the present invention relates to an effective amount of beta-lactamase of between about 1 mg to about 1,000 mg, (e.g. about 1 mg to about 900 mg, about 1 mg to about 800 mg, about 1 mg to about 750 mg, about 5 mg to about 750 mg, about 10 mg to about 750 mg, about 50 and about 750 mg about 50 mg to about 700 mg, or about 50 mg to about 650 mg, or about 50 mg to about 600 mg, or about 50 mg to about 550 mg, or about 50 mg to about 500 mg, or about 50 mg to about 450 mg, or about 50 mg to about 400 mg, or about 50 mg to about 350 mg, or about 50 mg to about 300 mg, or about 50 mg to about 250 mg, or about 50 mg to about 200 mg, or about 50 mg to about 150 mg, or about 50 mg to about 100 mg, or about 50 mg to about 75 mg, or about 75 mg to about 700 mg, or about 100 mg to about 700 mg, or about 150 mg to about 700 mg, or about 200 mg to about 700 mg, or about 250 mg to about 700 mg, or about 300 mg to about 700 mg, or about 350 mg to about 700 mg, or about 400 mg to about 700 mg, or about 450 mg to about 700 mg, or about 500 mg to about 700 mg, or about 550 mg to about 700 mg, or about 600 mg to about 700 mg, or about 650 mg to about 700 mg).

In various embodiments, the present invention relates to an effective amount of beta-lactamase of about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 450 mg, about 500 mg, about 550 mg, about 600 mg, about 650 mg, about 700 mg, about 750 mg, about 800 mg, about 850 mg, about 900 mg, about 950 mg, or about 1,000 mg that is used in various methods of treatment, regimens and formulations.

In various embodiments, the present invention relates to an effective amount of beta-lactamase of between about 1 mg to about 750 mg, about 5 mg to about 750 mg, about 50 and about 750 mg (e.g., about 50 mg, or about 75 mg, or about 100 mg, or about 125 mg, or about 150 mg, or about 175 mg, or about 200 mg, or about 250 mg, or about 300 mg, or about 350 mg, or about 400 mg, or about 450 mg, or about 450 mg, or about 500 mg, or about 550 mg, or about 600 mg, or about 650 mg, or about 700 mg, or about 750 mg) that is used in various methods of treatment, regimens and formulations.

In various embodiments, the present invention relates to an effective amount of beta-lactamase of between about 50 and about 200 mg (e.g., about 50 mg, or about 75 mg, or about 100 mg, or about 125 mg, or about 150 mg, or about 175 mg, or about 200 mg) that is used in various methods of treatment, regimens and formulations. In an embodiment, the effective amount of beta-lactamase is about 75 mg. In an embodiment, the effective amount of beta-lactamase is about 150 mg.

In certain embodiments, the beta-lactamase is administered as a single dose of about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 450 mg, about 500 mg, about 550 mg, about 600 mg, about 650 mg, about 700 mg, about 750 mg, about 800 mg, about 850 mg, about 900 mg, about 950 mg, or about 1,000 mg. In an embodiment, the beta-lactamase is administered as a single dose of about 75 mg. In another embodiment, the beta-lactamase is administered as a single dose of about 150 mg. In a further embodiment, the beta-lactamase is administered as a single dose of about 300 mg. In a yet further embodiment, the beta-lactamase is administered as a single dose of about 600 mg. In another embodiment, the beta-lactamase is administered as a single dose of about 750 mg.

In some embodiments, the beta-lactamase is administered once daily. For example, the beta-lactamase may be administered at a single dose of about 5 mg, about 10 mg, about 25 mg, about 50 mg, about 75 mg, or about 150 mg, or about 300 mg, or about 600 mg, or about 750 mg once daily.

In other embodiments, the beta-lactamase is administered more than once daily. For example, the beta-lactamase may be administered at least twice, at least three times, at least four times, at least five times, at least six times, at least seven times, at least eight times, at least nine times, or at least ten times daily. In an embodiment, the beta-lactamase is administered twice daily. In another embodiment, the beta-lactamase is administered three times daily. In a further embodiment, the beta-lactamase is administered four times daily. In an embodiment, the beta-lactamase is administered at a dose of about 75 mg for two times daily. In another embodiment, the beta-lactamase is administered at a dose of about 150 mg for two times daily. In a further embodiment, the beta-lactamase is administered at a dose of about 300 mg for two times daily. In an embodiment, the beta-lactamase is administered at a dose of about 75 mg for four times daily. In another embodiment, the beta-lactamase is administered at a dose of about 150 mg for four times daily. In a further embodiment, the beta-lactamase is administered at a dose of about 300 mg for four times daily.

In some embodiments, the beta-lactamase is administered to a subject for the entire course of an antibiotic treatment, e.g., an antibiotic from which the present beta-lactamase is providing GI microbiome protection. In some embodiments, the beta-lactamase is administered to a subject for about 1, about 2, about 3, about 4, about 5, about 6, or about 7 days. In an embodiment, the beta-lactamase is administered to a subject for about 7 consecutive days. In other embodiments, the beta-lactamase is administered for at least about 1, about 2, about 3, or about 4 weeks. In some embodiments, the beta-lactamase is administered for at least about 1, about 2, about 3, about 4, about 5, about 6, about 7, about 8, about 9, about 10, about 11, or about 12 months. In some embodiments, the beta-lactamase is administered for at least about 1 year.

In various embodiments, the beta-lactamase is administered to a subject prior to the start of the beta-lactam antibiotics. For example, the beta-lactamase may be administered about 30 minutes prior, about 1 hour prior, about 2 hours prior, about 3 hours prior, about 4 hours prior, about 5 hours prior, about 6 hours prior, about 7 hours prior, about 8 hours prior, about 9 hours prior, about 10 hours prior, about 11 hours prior, about 12 hours prior, about 13 hours prior, about 14 hours prior, about 15 hours prior, about 16 hours prior, about 17 hours prior, about 18 hours prior, about 19 hours prior, about 20 hours prior, about 21 hours prior, about 22 hours prior, about 23 hours prior, about 24 hours prior, about 2 days prior, or about 3 days prior. In an embodiment, the beta-lactamase is administered to a subject about 30 minutes prior to start of the beta-lactam antibiotics. In another embodiment, the beta-lactamase is administered to a subject about 1 hour prior to start of the beta-lactam antibiotics. In another embodiment, the beta-lactamase is administered to a subject about 2 hours prior to start of the beta-lactam antibiotics. In yet another embodiment, the beta-lactamase is administered to a subject about 3 hours prior to start of the beta-lactam antibiotics. In a further embodiment, the beta-lactamase is administered to a subject about 4 hours prior to start of the beta-lactam antibiotics.

In various embodiments, the beta-lactamase is administered for about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 1 week, about 2 weeks, about 3 weeks, or about 4 weeks after the conclusion of the beta-lactam antibiotics. In an embodiment, the beta-lactamase is administered for about 1 day after the conclusion of the beta-lactam antibiotics. In another embodiment, the beta-lactamase is administered for about 2 days after the conclusion of the beta-lactam antibiotics. In a further embodiment, the beta-lactamase is administered for about 3 days after the conclusion of the beta-lactam antibiotics.

In various embodiments, the present treatment methods include administering the described beta-lactam antibiotic and the described beta-lactamase simultaneously or sequentially. In some embodiments, the administration is sequential and the beta-lactam antibiotic is administered before the beta-lactamase. In some embodiments, the administration is sequential and the beta-lactamase is administered before the beta-lactam antibiotic.

In various embodiments, the beta-lactam antibiotic is administered orally. In various embodiments, the beta-lactam antibiotic is administered parenterally, optionally selected from intravenously, intramuscularly and/or by infusion while the beta-lactamase is administered orally.

In various embodiments, the method further comprises administering food to the patient. For example, in various embodiments, the present methods exploit a food effect on the administration of the present beta-lactamases, e.g., in some embodiments, food alters the rate and/or extent of absorption of the beta lactamase and/or beta-lactam antibiotic. In various embodiments, the present invention provides a regimen in which the patient being treated with the beta-lactamase and/or beta-lactam antibiotic is administered a snack or meal, optionally being high-calorie and/or high-fat or low calorie and/or low-fat, during and/or before treatment. In some embodiments, the snack or meal may have one or more illustrative effects: delay gastric emptying, stimulating bile flow, changing gastrointestinal (GI) pH, increasing splanchnic blood flow, changing luminal metabolism of a drug substance, and physically or chemically interacting with a dosage form or a drug substance. In various embodiments, the beta-lactamase and/or beta-lactam antibiotic is administered prior to a snack or meal. In various embodiments, the beta-lactamase and/or beta-lactam antibiotic is administered subsequent to a snack or meal.

In various embodiments, a small non-fatty meal is administered prior to administration of beta-lactam antibiotic and optionally again after infusion of beta-lactam antibiotic begins.

In various embodiments, the snack or meal is high in fat, for example, about 50 percent of total caloric content of the snack or meal are fat. In various embodiments, less than about 50 percent of total caloric content of the snack or meal is collectively protein, and carbohydrate. In some embodiments, the high-fat and/or high-calorie meal has about 800 to 1000 calories.

In various embodiments of the present invention, the beta-lactamase is administered sprinkled on or combined with a soft food, for example, applesauce or pudding to aid in swallowing.

In various embodiments, the present invention relates to fasting treatments. In various embodiments, the present invention relates to fed treatments.

In various embodiments, the method further comprises administering an agent that modulates GI tract pH (e.g. a proton pump inhibitor). In various embodiments, the proton pump inhibitor is selected from one or more of omeprazole (PRILOSEC), esomeprazole (NEXIUM), lansoprazole (PREVACID), rabeprazole (ACIPHEX), pantoprazole (PROTONIX), and dexlansoprazole (KAPIDEX). In one embodiment, the proton pump inhibitor is esomeprazole. In some embodiments, the patient is undergoing treatment with the proton pump inhibitor.

In some embodiments, the present invention provides for a method of promoting early release of the beta-lactamase into the intestines by administering the beta-lactamase with an agent that modulates GI tract pH (e.g. a proton pump inhibitor). In some embodiments, the release is earlier than the release of the beta-lactamase into the intestines in the absence of a proton pump inhibitor. In various embodiments, the proton pump inhibitor is administered prior to the beta-lactamase, concurrently with the beta-lactamase, or after the beta-lactamase. In some embodiments, the subject has been taking proton pump inhibitors or other GI pH modulating factors for several days prior to the beta-lactamase. In one embodiment, the proton pump inhibitor is esomeprazole.

In some embodiments, the present invention provides for a method of promoting early release of SYN-004 into the intestines by administering SYN-004 with a proton pump inhibitor (e.g., esomeprazole). In some embodiments, the release is earlier than the release of SYN-004 into the intestines in the absence of proton pump inhibitors. Accordingly, in some embodiments, the present invention provides for a regimen in which a beta-lactamase (e.g. SYN-004) is administered simultaneously with the proton pump inhibitor (e.g., esomeprazole such as e.g. NEXIUM)).

In an illustrative embodiment, the SYN-004 may be released into the intestines (e.g., into the intestinal chyme) where it starts to degrade antibiotics (e.g., ceftriaxone) about 4 hours after administration, or about 3 hours after administration, or about 2 hours after administration. In some embodiments, administration of a proton pump inhibitor (e.g., esomeprazole) reduces this lag time and promotes an earlier release of SYN-004 into the intestines (e.g., into the intestinal chyme) compared to release of SYN-004 in the absence of the proton pump inhibitor. For example, rather than being released into the intestines (e.g., into the intestinal chyme) where it starts to degrade antibiotics (e.g., ceftriaxone) about 4 hours after administration, administration of a proton pump inhibitor (e.g., esomeprazole) may allow SYN-004 to be released into the intestines (e.g., into the intestinal chyme) to degrade antibiotics (e.g., ceftriaxone) about 30 minutes earlier, about 1 hour earlier, about 1.5 hours earlier, about 2 hours earlier, about 2.5 hours earlier, about 3 hours earlier. In such embodiments, the SYN-004 may be administered at a dose of 75 mg twice daily or at a dose of 150 mg twice daily.

In some embodiments, the present invention provides for a method of promoting early release of the beta-lactamase into the intestines by administering the beta-lactamase with an antacid. Antacids are generally a chemical salt of an alkaline ion and a counterion. In various embodiments, the alkaline ion is carbonate or bicarbonate. In some embodiments, the alkaline ion is hydroxide. Exemplary antacids that include carbonate or bicarbonate as the alkaline ion include, for example, Alka-Seltzer, Andrews antacid, Brioschi, Equate, Maalox, Pepto-Bismol, Rennie, Rolaids, Tums, Eno, Gaviscon, and Quick-Eze. Exemplary antacids that include hydroxide as the alkaline ion include, for example, Milk of Magnesia, Mylanta, Droxygel, and Gelusil.

Antibiotics

In various embodiments, the beta-lactamase degrades or inactivates one or more antibiotics. In various embodiments, the patient is undergoing treatment or has recently undergone treatment with one or more antibiotics. In various embodiments, the described beta-lactamases (and/or additional therapeutic agents) are formulated in a manner that preserves the therapeutic (e.g. systemic) action of one or more antibiotics while preventing the action of excess amounts of these in the GI tract, where they may disrupt the GI microbiota. For instance, such antibiotics may be administered parenterally (e.g. intravenously) or orally and residual or excess antibiotic may remain in or be excreted into the GI tract (e.g. from lack of absorption into the blood stream or through hepatobiliary excretion back into intestine). Such excess or residual antibiotic may disrupt the GI microbiota (e.g. disrupt a healthy balance (e.g. a healthy ratio and/or healthy distribution) of intestinal microbiota in a patient). In certain embodiments, the parenterally or orally administered antibiotics are selected from beta-lactam containing antibiotics such as penicillins and cephalosporins.

Penicillins include, for example, Amdinocillin, Amoxicillin (e.g. NOVAMOX, AMOXIL); Ampicillin (e.g. PRINCIPEN); Azlocillin; Carbenicillin (e.g. GEOCILLIN); Cloxacillin (e.g. TEGOPEN); Cyclacillin, Dicloxacillin (e.g. DYNAPEN); Flucloxacillin (e.g. FLOXAPEN); Mezlocillin (e.g. MEZLIN); Methicillin (e.g. STAPHCILLIN); Nafcillin (e.g. UNIPEN); Oxacillin (e.g. PROSTAPHLIN); Penicillanic Acid, Penicillin G (e.g. PENTIDS or PFIZERPEN); Penicillin V (e.g. VEETIDS (PEN-VEE-K)); Piperacillin (e.g. PIPRACIL); Sulbactam, Temocillin (e.g. NEGABAN); and Ticarcillin (e.g. TICAR).

Illustrative penicillins include:

| Generic | Brand Name |
| --- | --- |
| Amoxicillin | AMOXIL, POLYMOX, TRIMOX, WYMOX |
| Ampicillin | OMNIPEN, POLYCILLIN, POLYCILLIN-N, PRINCIPEN, TOTACILLIN |
| Bacampicillin | SPECTROBID |
| Carbenicillin | GEOCILLIN, GEOPEN |
| Cloxacillin | CLOXAPEN |
| Dicloxacillin | DYNAPEN, DYCILL, PATHOCIL |
| Flucloxacillin | FLOPEN, FLOXAPEN, STAPHCILLIN |
| Mezlocillin | MEZLIN |
| Nafcillin | NAFCIL, NALLPEN, UNIPEN |
| Oxacillin | BACTOCILL, PROSTAPHLIN |
| Penicillin G | BICILLIN L-A, CRYSTICILLIN 300 A.S., PENTIDS, PERMAPEN, PFIZERPEN, PFIZERPEN-AS, WYCILLIN |
| Penicillin V | BEEPEN-VK, BETAPEN-VK, LEDERCILLIN VK, V-CILLIN K |
| Piperacillin | PIPRACIL |
| Pivampicillin | |
| Pivmecillinam | |
| Ticarcillin | TICAR |

Cephalosporins include, for example, a first generation cephalosporin (e.g. Cefadroxil (e.g. DURICEF); Cefazolin (e.g. ANCEF); Ceftolozane, Cefalotin/Cefalothin (e.g. KEFLIN); Cefalexin (e.g. KEFLEX); a second generation cephalosporin (e.g. Cefaclor (e.g. DISTACLOR); Cefamandole (e.g. MANDOL); Cefoxitin (e.g. MEFOXIN); Cefprozil (e.g. CEFZIL); Cefuroxime (e.g. CEFTIN, ZINNAT)); a third generation cephalosporin (e.g. Cefixime (e.g. SUPRAX); Cefdinir (e.g. OMNICEF, CEFDIEL); Cefditoren (e.g. SPECTRACEF); Cefoperazone (e.g. CEFOBID); Cefotaxime (e.g. CLAFORAN); Cefpodoxime (e.g. VANTIN); Ceftazidime (e.g. FORTAZ); Ceftibuten (e.g. CEDAX) Ceftizoxime (e.g. CEFIZOX); and Ceftriaxone (e.g. ROCEPHIN)); a fourth generation cephalosporin (e.g. Cefepime (e.g. MAXIPIME)); or a fifth generation cephalosporin (e.g. Ceftaroline fosamil (e.g. TEFLARO); Ceftobiprole (e.g. ZEFTERA)). Also included is Latamoxef (or moxalactam). In a specific embodiment, cephalosporins include, for example, cefoperazone, ceftriaxone or cefazolin.

Illustrative cephalosporins include

| Generic | Brand Name |
| --- | --- |
| First Generation | |
| Cefacetrile (cephacetrile) | CELOSPOR, CELTOL, CRISTACEF |
| Cefadroxil (cefadroxyl) | DURICEF, ULTRACEF |
| Cefalexin (cephalexin) | KEFLEX, KEFTAB |
| Cefaloglycin (cephaloglycin) | KEFGLYCIN |
| Cefalonium (cephalonium) | |
| Cefaloridine (cephaloradine) | |
| Cefalotin (cephalothin) | KEFLIN |
| Cefapirin (cephapirin) | CEFADYL |
| Cefatrizine | |
| Cefazaflur | |
| Cefazedone | |
| Cefazolin (cephazolin) | ANCEF, KEFZOL |
| Cefradine (cephradine) | VELOSEF |

-continued

| Generic | Brand Name |
|---|---|
| Cefroxadine | |
| Ceftezole | |
| Second Generation | |
| Cefaclor | CECLOR, CECLOR CD, DISTACLOR, KEFLOR, RANICOR |
| Cefamandole | MANDOL |
| Cefmetazole | |
| Cefonicid | MONOCID |
| Cefotetan | CEFOTAN |
| Cefoxitin | MEFOXIN |
| Cefprozil (cefproxil) | CEFZIL |
| Cefuroxime | CEFTIN, KEFUROX, ZINACEF, ZINNAT |
| Cefuzonam | |
| Third Generation | |
| Cefcapene | |
| Cefdaloxime | |
| Cefdinir | OMNICEF, CEFDIEL |
| Cefditoren | SPECTRACEF |
| Cefetamet | |
| Cefixime | SUPRAX |
| Cefmenoxime | CEFMAX |
| Cefodizime | |
| Cefotaxime | CLAFORAN |
| Cefpimizole | |
| Cefpodoxime | VANTIN |
| Cefteram | |
| Ceftibuten | CEDAX |
| Ceftiofur | EXCEDE |
| Ceftiolene | |
| Ceftizoxime | CEFIZOX |
| Ceftriaxone | ROCEPHIN |
| Cefoperazone | CEFOBID |
| Ceftazidime | CEPTAZ, FORTUM, FORTAZ, TAZICEF, TAZIDIME |
| Fourth Generation | |
| Cefclidine | |
| Cefepime | MAXIPIME |
| Cefluprenam | |
| Cefoselis | |
| Cefozopran | |
| Cefpirome | CEFROM |
| Cefquinome | |
| Fifth Generation | |
| Ceftobiprole | ZEFTERA |
| Ceftaroline | TEFLARO |
| Not Classified | |
| Cefaclomezine | |
| Cefaloram | |
| Cefaparole | |
| Cefcanel | |
| Cefedrolor | |
| Cefempidone | |
| Cefetrizole | |
| Cefivitril | |
| Cefmatilen | |
| Cefmepidium | |
| Cefovecin | |
| Cefoxazole | |
| Cefrotil | |
| Cefsumide | |
| Cefuracetime | |
| Ceftioxide | |

In various embodiments, the beta-lactam antibiotics may be formulated with, combined with or administered with a beta-lactamase inhibitor for example, clavulanic acid, tazobactam, sulbactam, avibactam, or EDTA. In some embodiments, the beta-lactamase inhibitors do not significantly interfere with the activities of the beta-lactamase. In some embodiments, the beta-lactamase inhibitors do not significantly interfere with the activities of the beta-lactamase in the intestinal chyme. In some embodiments, the beta-lactamase inhibitors do not prevent the beta-lactamase from degrading the excess or residual antibiotics in the intestinal chyme.

Methods of Treatment

In various aspects, the present invention provides methods for protecting a patient's gastrointestinal microbiome, comprising administering an effective amount of a pharmaceutical composition comprising a beta-lactamase (e.g. SYN-004), for example, any of the doses and/or formulations described herein. In various embodiments, the patient is undergoing treatment or has recently undergone treatment with an antibiotic.

In various embodiments, the bloodstream or plasma levels of beta-lactam antibiotic in the patient are not substantially reduced relative to an untreated patient. In various embodiments, the bloodstream or plasma of the patient is substantially free of the beta-lactamase. In various embodiments, the beta-lactamase does not substantially interfere with blood or plasma levels of the antibiotic. In various embodiments, the beta-lactamase degrades or inactivates excess or residual antibiotic in the GI tract. In various embodiments, the beta-lactam antibiotic is degraded in the patient's intestinal chyme.

In various embodiments, the patients include, but are not limited to, patients that are at a particular risk for a microbiome-mediated disorder, such as, by way of non-limiting example, those undergoing treatment or having recently undergone treatment with an antibiotic. For example, the patient may have taken an antibiotic during the past about 30 or so days and/or have an immune system that is weak (e.g. from a chronic illness) and/or is a women and/or is elderly (e.g., over about 65 years old) and/or is an elderly woman and/or is undergoing (or has undergone) treatment with for heartburn or stomach acid disorders (e.g. with agents such as PREVACID, TAGAMET, PRILOSEC, or NEXIUM and related drugs) and/or has recently been in the hospital, including in an intensive care unit, or lives in a nursing home. Accordingly, in some embodiments, the methods and uses of the present invention treat or prevent a nosocomial infection and/or a secondary infection and/or an opportunistic infection and/or a hospital acquired infection (HAI).

In some embodiments, the methods and uses of the present invention include those in which an initial and/or adjunctive therapy is administered to a patient. Initial and/or adjunctive therapy indicates therapy that is used to treat for example, a microbiome-mediated disorder or disease upon detection of such disorder or disease. In some embodiments, the initial and/or adjunctive therapy is one or more of metronidazole, vancomycin, fidaxomicin, rifaximin, charcoal-based binder/adsorbent, fecal bacteriotherapy, fecal replacement therapy, probiotic therapy, prebiotic therapy and antibody therapy, as described herein. In various embodiments, the methods and uses of the present invention include use of the pharmaceutical compositions and formulations including a beta-lactamase (and/or additional therapeutic agent) as an adjuvant to any of these initial and/or adjunctive therapies (including co-administration or sequential administration). In various embodiments, the methods and uses of the present invention include use of the pharmaceutical compositions and formulations including a beta-lactamase (and/or additional therapeutic agent) in a patient undergoing initial and/or adjunctive therapies.

In some embodiments, the methods and uses of the present invention include those in which an antibiotic and an inhibitor of beta-lactamase are administered to a patient. In various embodiments, the patient may be receiving a co-formulation of an antibiotic with one or more beta-lactamase inhibitors (e.g. Augmentin is a mixture of amoxicillin and clavulanic acid). Such co-formulations include, but are not limited to, amoxicillin-clavulanic acid (e.g. AUGMENTIN), ticarcillin-clavulanic acid (e.g. TIMENTIN), ampicillin-sulbactam (Sultamicillin, e.g. UNASYN), piperacillin-tazobactam (e.g. ZOSYN), cefoperazone-sulbactam, ceftazidime-avibactam (AVYCAZ), and ceftaroline-avibactam.

In various embodiments, methods of the present invention comprise further administering a beta-lactamase inhibitor that releases in the GI tract proximal to the beta-lactamase. For example, the beta-lactamase inhibitor may be released at the stomach, duodenum, jejunum and ileum. Illustrative beta-lactamase inhibitors include, for example, tazobactam, sulbactam, EDTA, clavulanic acid, avibactam, monobactam derivatives, ATMO derivatives, penems (e.g., BRL42715 and derivatives thereof, Syn1012, oxapenems, trinems, 1-β-methylcarbapenems), penicillin and cephalosporin sulfone derivatives (e.g., C-2/C-3-substituted penicillin and cephalosporin sulfones, C-6-substituted penicillin sulfones), non-β-lactam inhibitors (e.g., boronic acid transition state analogs, phophonates, NXL104, hydroxmates) and metallo-β-lactamase inhibitors such as thiol derivatives, pyridine dicarboxylates, trifluoromethyl ketones and alcohols, carbapenem analogs, tricyclic natural products, succinate derivatives, and C-6-mercaptomethyl penicillinates.

In various embodiments, the methods of the invention comprise treating or preventing a microbiome-mediated disorder. Illustrative microbiome-mediated disorder includes, but are not limited to, for example, those found in Table 3 of WO 2014/121298, the entire contents of which are incorporated herein by reference.

For example, the microbiome-mediated disorder may be selected from an antibiotic-induced adverse effect, a *C. difficile* infection (CDI), a *C. difficile*-associated disease, ulcerative colitis, Crohn's disease, irritable bowel syndrome and antibiotic associated diarrhea (e.g., of unknown origin).

In various embodiments, the microbiome mediated disorders also include, fatty liver disease, autism, depression, Parkinson's disease, obesity, metabolic disorders, chronic fatigue syndrome, immune-mediated disorders (e.g., Lupus), or any disorder associated with an imbalance of the gut microbiome.

For example, in some embodiments, the present invention provides methods of treating or preventing metabolic syndrome, diabetes (type 1 or type 2), hypertension, cardiovascular disease, fatty liver disease (e.g., nonalcoholic fatty liver disease) and other metabolic diseases. Additional metabolic diseases that may be treated using methods of the invention include those described in US2013/0251701, US2011/0206654, and US2004/0115185, the entire contents of which are hereby incorporated by reference.

In some embodiments, the present invention provides methods of treating or preventing neurodegenerative diseases. In some embodiments, the neurodegenerative disease is selected from multiple sclerosis, Alzheimer's disease, Parkinson's disease and parkinsonism, Huntington's disease, or Amyotrophic lateral sclerosis.

In some embodiments, the present invention provides methods of treating or preventing immunological disorders. For example, the immunological disorder may be an autoimmune disorder. Exemplary autoimmune disorders include, but are not limited to, systemic lupus erythematosus (SLE), celiac disease, Crohn's disease, and ulcerative colitis.

In various embodiments, the microbiome-mediated disorder is an antibiotic-induced adverse effect, a *C. difficile* infection (CDI), or a *C. difficile*-associated disease. In an embodiment, the present invention provides methods for treating an antibiotic-induced adverse effect in the GI tract, comprising administering an effective amount of a pharmaceutical composition or formulation including a beta-lactamase (and/or additional therapeutic agent) described herein to a patient who is undergoing treatment or has recently undergone treatment with an antibiotic. In another embodiment, the present invention provides methods for preventing an antibiotic-induced adverse effect in the GI tract, comprising administering an effective amount of a pharmaceutical composition or formulation including a beta-lactamase (and/or additional therapeutic agent) described herein to a patient who is undergoing treatment or has recently undergone treatment with an antibiotic.

In some embodiments, the patient is a human child. For example, microbiome disruption is linked to multiple metabolic, immune, neurological, etc. disorders. Early exposure to antibiotics (e.g. within about the first 2 years of life) can disrupt the microbiome and lead to eventual disease. Bailey, et al. JAMA Pediatr. 168(11), November 2014, the entire contents of which are hereby incorporated by reference, describes how early exposure to antibiotics is linked to obesity. Accordingly, in some embodiments, the present methods protect the microbiome of a child and prevent diseases such as obesity.

In an embodiment, the present invention provides methods for treating *C. difficile* infection (CDI) and/or a *C. difficile*-associated disease, comprising administering an effective amount of a pharmaceutical composition or formulation including a beta-lactamase (and/or additional therapeutic agent) described herein to a patient who is undergoing treatment or has recently undergone treatment with an antibiotic. In another embodiment, the present invention provides methods for preventing *C. difficile* infection (CDI) and/or a *C. difficile*-associated disease, comprising administering an effective amount of a pharmaceutical composition or formulation including a beta-lactamase (and/or additional therapeutic agent) described herein to a patient who is undergoing treatment or has recently undergone treatment with an antibiotic.

In various embodiments, the antibiotic-induced adverse effect and/or CDI or *C. difficile*-associated disease is one or more of: antibiotic-associated diarrhea, *C. difficile* diarrhea (CDD), *C. difficile* intestinal inflammatory disease, colitis, pseudomembranous colitis, fever, abdominal pain, dehydration and disturbances in electrolytes, megacolon, peritonitis, and perforation and/or rupture of the colon. Additional diseases, disorders and conditions which are suitable for treatment with the compositions and methods of the invention include those listed in Table 3 of WO 2014/121298, the entire contents of which are incorporated herein by reference.

In various embodiments, the present uses and methods pertain to co-treatment (simultaneously or sequentially) with the pharmaceutical composition or formulation including a beta-lactamase (and/or additional therapeutic agent) described herein and/or any initial and/or adjunctive therapy, or treatment with a co-formulation of the pharmaceutical composition or formulation including a beta-lactamase (and/or any additional therapeutic agent) described herein and/or any initial and/or adjunctive therapy for treatment of the various diseases described herein.

In various embodiments, the microbiome-mediated disorder is treated or prevented in the context of initial onset or relapse/recurrence (e.g. due to continued or restarted antibiotic therapy). For example, in a patient that has previously suffered from a microbiome-mediated disorder (e.g., CDI), the present pharmaceutical composition or formulation including a beta-lactamase (and/or additional therapeutic agent) may be administered upon the first symptoms of recurrence in the patient. By way of non-limiting example, symptoms of recurrence include, in a mild case, about 3 or more watery bowel movements per day (e.g., about 5 to about 10 watery bowel movements per day), no significant fever, and only mild abdominal cramps while blood tests may show a mild rise in the white blood cell count up to about 15,000 (normal levels are up to about 10,000), and, in a severe case, more than about 10 watery stools per day, nausea, vomiting, high fever (e.g. about 102-104° F.), rectal bleeding, severe abdominal pain (e.g. with tenderness), abdominal distention, and a high white blood count (e.g. of about 15,000 to about 40,000).

Regardless of initial onset or relapse/recurrence, the microbiome-mediated disorder may be diagnosed via any of the symptoms described herein (e.g. watery diarrhea about 3 or more times a day for about 1 day, or about 2 days, or more, mild to bad cramping and pain in the belly, fever, blood or pus in the stool, nausea, dehydration, loss of appetite, loss of weight, etc.). Regardless of initial onset or relapse/recurrence, the microbiome-mediated disorder may also be diagnosed via enzyme immunoassays (e.g. to detect the *C. difficile* toxin A or B antigen and/or glutamine dehydrogenase (GDH), which is produced by *C. difficile* organisms), polymerase chain reactions (e.g., to detect the *C. difficile* toxin A or B gene or a portion thereof (e.g. tcdA or tcdB), including the ILLUMIGENE LAMP assay), a cell cytotoxicity assay. For example, any of the following tests may be used: Meridian ImmunoCard Toxins A/B; Wampole Toxin A/B Quik Chek; Wampole C. diff Quik Chek Complete; Remel Xpect *Clostridium difficile* Toxin NB; Meridian Premier Toxins A/B; Wampole *C. difficile* Tox A/B II; Remel Prospect Toxin A/B EIA; Biomerieux Vidas *C. difficile* Toxin A&B; BD Geneohm C. diff; Prodesse Progastro CD; TecLab Toxin NB and Cepheid Xpert C. diff. In various embodiments, the clinical sample is a patient's stool sample.

The microbiome mediated disorder may also be diagnosed by examination of a stool samples or multiple stool samples from a subject to look for imbalance of the microbiome. This examination can be through 16s rRNA sequencing, deep gene sequencing, metagenomics analysis, transcriptomic analysis, proteomic analysis, and metabolomics analysis. Examination can also be conducted on the resistome of the fecal microbiome to look for antibiotic resistance determinants, including but limited to, beta-lactamases and efflux pumps.

In addition, a flexible sigmoidoscopy "scope" test and/or an abdominal X-ray and/or a computerized tomography (CT) scan, which provides images of the colon, may be used in assessing a patient (e.g. looking for characteristic creamy white or yellow plaques adherent to the wall of the colon). Further, biopsies (e.g. of any region of the GI tract) may be used to assess a potential microbiome-mediated disorder (e.g., CDI and/or *C. difficile* associated disease) in patient.

In various embodiments, the methods and uses of the present invention relate to pharmaceutical compositions and formulations including a beta-lactamase (and/or additional therapeutic agent) which release the beta-lactamase (and/or additional therapeutic agent) in a location in the GI tract in which it degrades or inactivates excess antibiotic residue as described herein.

In some embodiments, methods and uses of the present invention relate to pharmaceutical compositions and formulations including a beta-lactamase (and/or additional therapeutic agent) which maintain a normal intestinal microbiota and/or prevent the overgrowth of one or more pathogenic microorganisms in the GI tract of a patient. In various embodiments, the present invention provides for pharmaceutical compositions and methods that mitigate or prevent the overgrowth of various coliforms in a patient's gut (including coliforms that are virulent and/or antibiotic resistant). In various aspects, the methods, pharmaceutical compositions and formulations described herein prevent or diminish secondary infections with resistant organisms and may, in some embodiments, diminish antibiotic resistance development. Further, the methods, pharmaceutical compositions and formulations described herein may allow for use of antibiotics which are currently avoided due to resistance concerns and/or reduce the need for co-administration or co-formulation with one or more inhibitor of the beta-lactamases. Further the pharmaceutical compositions and formulations described herein may prevent dysbiosis of the gut microbiome which can then lead to metabolic and inflammatory disorders.

In various embodiments, the beta-lactamases and/or pharmaceutical compositions (and/or additional therapeutic agents) do not substantially interfere with blood or plasma levels of an antibiotic. For example, the beta-lactamases and/or pharmaceutical compositions (and/or additional therapeutic agents) of the present invention allow for a patient to receive an antibiotic that might be required for an infection and do not interfere with the systemic activity of the antibiotic. In an embodiment, the beta-lactamases and/or pharmaceutical compositions (and/or additional therapeutic agents) does not substantially interfere with blood or plasma levels of the antibiotic. Rather, the beta-lactamases and/or pharmaceutical compositions (and/or additional therapeutic agents) inactivate excess antibiotic that may populate parts of the GI tract and in doing so, prevent the disruption of the microbiota that is linked to the various disease states described herein.

In various embodiments, the pharmaceutical compositions and formulations including a beta-lactamase and/or additional therapeutic agent are not systemically absorbed or the systemic absorption is minimal. In various embodiments, the beta-lactamase and/or additional therapeutic agent included in the pharmaceutical compositions and formulations of the invention are not systemically bioavailable. In an embodiment, the beta-lactamase and/or additional therapeutic agent included in the pharmaceutical compositions and formulations are not systemically bioavailable after a multiple dosing regimen as described herein.

In various embodiments, the beta-lactamase and/or additional therapeutic agent included in the pharmaceutical compositions and formulations of the invention is substantially absent from the bloodstream or plasma of the subject. In various embodiments, the beta-lactamase and/or additional therapeutic agent does not substantially reduce the bloodstream or plasma anti-infective activity of an antibiotic that a subject is receiving.

In various embodiments, to the extent that any beta-lactamase and/or additional therapeutic agent is present in the bloodstream or plasma of the subject, the peak concentration is about 1, about 2, about 3, about 4, about 5, about 6, about 7, about 8 about 9, about 10, about 11, or about 12 hours following administration. For example the beta-lactamase and/or additional therapeutic agent may reach a peak plasma concentration at about 2, about 3, or about 4 hours post administration. In some embodiments, the administration of an antibiotic may be greater than about 1, greater than about 2, greater than about 3, greater than about 4, greater than about 5, greater than about 6, greater than about 7, greater than about 8, greater than about 9, greater than about 10, greater than about 11, or greater than about 12 hours following administration of any beta-lactamase and/or additional therapeutic agent. In various embodiments, the peak plasma concentration of the beta-lactamase and/or additional therapeutic agent is lower than, at, or near the lower limit of quantification of an assay used to measure plasma concentration. In an embodiment, the peak plasma concentration of the beta-lactamase and/or additional therapeutic agent is lower than, or nears, the lower limit of quantification of an assay used to measure plasma concentration after a multiple dosing regimen as described herein.

In various embodiments, the pharmaceutical compositions and formulations including a beta-lactamase (and/or additional therapeutic agent) do not induce or generate antibodies to the beta-lactamase (and/or additional therapeutic agent).

In various embodiments, the pharmaceutical compositions and formulations including a beta-lactamase (and/or additional therapeutic agent) function to eliminate antibiotics from interfering with the balance of a microbiome (e.g. the gut, including the large intestine). In some embodiments, the pharmaceutical compositions and formulations including a beta-lactamase (and/or additional therapeutic agent) do not interfere with the antibiotic absorption from the gut and/or enterohepatically sufficiently to alter the half-lives of antibiotic circulation. In some embodiments, the compositions and formulations including a beta-lactamase (and/or additional therapeutic agent) do not interfere with the antibiotic absorption from the gut and/or enterohepatically enough to be clinically important.

Additional Therapeutic Agents and Combination Therapy or Co-Formulation

Administration of the present beta-lactamases may be combined with additional therapeutic agents. Co-administration of the additional therapeutic agent and the present formulations may be simultaneous or sequential. Further, the present formulations may comprise an additional therapeutic agent (e.g. via co-formulation). For example, the additional therapeutic agent and the beta-lactamase may be combined into a single formulation. Alternatively, the additional therapeutic agent and the beta-lactamase may be formulated separately.

In one embodiment, the additional therapeutic agent and the beta-lactamase are administered to a patient simultaneously. The term "simultaneously" as used herein, means that the additional therapeutic agent and the beta-lactamase are administered with a time separation of no more than about 60 minutes, such as no more than about 30 minutes, no more than about 20 minutes, no more than about 10 minutes, no more than about 5 minutes, or no more than about 1 minute. Administration of the additional therapeutic agent and the beta-lactamase can be by simultaneous administration of a single formulation (e.g., a formulation comprising the additional therapeutic agent and the beta-lactamase) or of separate formulations (e.g., a first formulation including the additional therapeutic agent and a second formulation including the beta-lactamase).

In a further embodiment, the additional therapeutic agent and the beta-lactamase are administered to a patient simultaneously but the release of additional therapeutic agent and the beta-lactamase from their respective dosage forms (or single unit dosage form if co-formulated) in the GI tract occurs sequentially.

Co-administration does not require the additional therapeutic agents to be administered simultaneously, if the timing of their administration is such that the pharmacological activities of the additional therapeutic agent and the beta-lactamase overlap in time. For example, the additional therapeutic agent and the beta-lactamase can be administered sequentially. The term "sequentially" as used herein means that the additional therapeutic agent and the beta-lactamase are administered with a time separation of more than about 60 minutes. For example, the time between the sequential administration of the additional therapeutic agent and the beta-lactamase can be more than about 60 minutes, more than about 2 hours, more than about 5 hours, more than about 10 hours, more than about 1 day, more than about 2 days, more than about 3 days, or more than about 1 week apart. The optimal administration times will depend on the rates of metabolism, excretion, and/or the pharmacodynamic activity of the additional therapeutic agent and the beta-lactamase being administered. Either the additional therapeutic agent or the beta-lactamase may be administered first.

Co-administration also does not require the additional therapeutic agents to be administered to the patient by the same route of administration. Rather, each additional therapeutic agent can be administered by any appropriate route, for example, parenterally or non-parenterally.

In some embodiments, the additional therapeutic agent is an anti-bacterial agent, which includes, but is not limited to, cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); monobactam antibiotics (aztreonam); and carbapenem antibiotics (ertapenem, doripenem, imipenem/cilastatin, and meropenem). In some embodiments, any of the penicillin, cephalosporin, monobactam, and carbapenem antibiotics described herein may be the additional therapeutic agent. In some embodiments, the additional therapeutic agent is an anti-bacterial agent, which includes, but is not limited to, the antibiotics described elsewhere herein.

In some embodiments, the additional therapeutic agent is a beta-lactamase inhibitor. Illustrative inhibitors include, any of the agents described herein. Illustrative inhibitors include tazobactam, sulbactam, EDTA, clavulanic acid, avibactam, monobactam derivatives, ATMO derivatives, penems (e.g., BRL42715 and derivatives thereof, Syn1012, oxapenems, trinems, 1-β-methylcarbapenems), penicillin and cephalosporin sulfone derivatives (e.g., C-2/C-3-substituted penicillin and cephalosporin sulfones, C-6-substituted penicillin sulfones), non-β-lactam inhibitors (e.g., boronic acid transition state analogs, phophonates, NXL104, hydroxmates) and metallo-β-lactamase inhibitors such as thiol derivatives, pyridine dicarboxylates, trifluoromethyl ketones and alcohols, carbapenem analogs, tricyclic natural products, succinate derivatives, and C-6-mercaptomethyl penicillinates.

In some embodiments, the additional therapeutic agent is an adjunctive therapy that is used in, for example, the treatment of CDI as described herein. In some embodiments, the additional therapeutic agent is metronidazole (e.g. FLAGYL), fidaxomicin (e.g. DIFICID), or vancomycin (e.g. VANCOCIN), rifaximin, charcoal-based binders/adsorbents (e.g. DAV132), fecal bacteriotherapy, probiotic therapy (see, e.g., *Intnat'l J. Inf Dis,* 16 (11): e786, the contents of which are hereby incorporated by reference, illustrative probiotics include *Saccharomyces boulardii;*

*Lactobacillus rhamnosus* GG; *Lactobacillus plantarum* 299v; *Clostridium butyricum* M588; *Clostridium difficile* VP20621 (non-toxigenic *C. difficile* strain); combination of *Lactobacillus casei, Lactobacillus acidophilus* (Bio-K+ CL1285); combination of *Lactobacillus casei, Lactobacillus bulgaricus, Streptococcus thermophilus* (Actimel); combination of *Lactobacillus acidophilus, Bifidobacterium bifidum* (Florajen3); combination of *Lactobacillus acidophilus, Lactobacillus bulgaricus delbrueckii* subsp. *bulgaricus, Lactobacillus bulgaricus casei, Lactobacillus bulgaricus plantarum, Bifidobacterium longum, Bifidobacterium infantis, Bifidobacterium breve, Streptococcus salivarius* subsp. *thermophilus* (VSL #3)) and antibody or other biologic therapy (e.g. monoclonal antibodies against *C. difficile* toxins A and B as described in N Engl J Med. 2010; 362(3):197, the content of which are hereby incorporated by reference in their entirety; neutralizing binding proteins, for example, arranged as multimers, which are directed to one or more of SEQ ID NOs. recited in United States Patent Publication No. 2013/0058962 (e.g. one or more of SEQ ID Nos.: 59, 60, 95, 67, 68, and 87), the contents of which are hereby incorporated by reference); or any neutralizing binding protein directed against *C. difficile* binary toxin.

In some embodiments, the additional therapeutic agent is an antidiarrheal agent. Antidiarrheal agents suitable for use in the present invention include, but are not limited to, DPP-IV inhibitors, natural opioids, such as tincture of opium, paregoric, and codeine, synthetic opioids, such as diphenoxylate, difenoxin and loperamide, bismuth subsalicylate, lanreotide, vapreotide and octreotide, motiln antagonists, COX2 inhibitors like celecoxib, glutamine, thalidomide and traditional antidiarrheal remedies, such as kaolin, pectin, berberine and muscarinic agents.

In some embodiments, the additional therapeutic agent is an anti-inflammatory agent such as steroidal anti-inflammatory agents or non-steroidal anti-inflammatory agents (NSAIDS). Steroids, particularly the adrenal corticosteroids and their synthetic analogues, are well known in the art. Examples of corticosteroids useful in the present invention include, without limitation, hydroxyltriamcinolone, alpha-methyl dexamethasone, beta-methyl betamethasone, beclomethasone dipropionate, betamethasone benzoate, betamethasone dipropionate, betamethasone valerate, clobetasol valerate, desonide, desoxymethasone, dexamethasone, diflorasone diacetate, diflucortolone valerate, fluadrenolone, fluclorolone acetonide, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, clocortelone, clescinolone, dichlorisone, difluprednate, flucloronide, flunisolide, fluorometholone, fluperolone, fluprednisolone, hydrocortisone, meprednisone, paramethasone, prednisolone, prednisone, beclomethasone dipropionate. (NSAIDS) that may be used in the present invention, include but are not limited to, salicylic acid, acetyl salicylic acid, methyl salicylate, glycol salicylate, salicylmides, benzyl-2,5-diacetoxybenzoic acid, ibuprofen, fulindac, naproxen, ketoprofen, etofenamate, phenylbutazone, and indomethacin. Additional anti-inflammatory agents are described, for example, in U.S. Pat. No. 4,537,776, the entire contents of which are incorporated by reference herein.

In some embodiments, the additional therapeutic agent may be an analgesic. Analgesics useful in the compositions and methods of the present invention include, without limitation, morphine, codeine, heroine, methadone and related compounds, thebaine, orpiavine, and their derivatives, buprenorphine, the piperidines, morphinans, benzomorphans, tetrahydroisoquinolines, thiambutanes, benzylamines, tilidine, viminol, nefopam, capsaicin(8-methyl-N-vanillyl-6E-nonenamide), "synthetic" capsaicin(N-vanillylnonamide), and related compounds.

In some embodiments, the additional therapeutic agent may be an anti-viral agent that includes, but is not limited to, Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, and Foscarnet.

In some embodiments, the additional therapeutic agent may be an anti-fungal agent that includes, but is not limited to, nystatin (Mycostatin, Nilstat, Bio-Statin, and Mycostatin Pastilles), amphotericin B, fluconazole (Diflucan), itraconazole, posaconazole, voriconazole, caspofungin, micafungin, and anidulafungin.

In some embodiments, the present invention provides for the co-administration (e.g. via co-formulation or separate formulations) of one or more of the beta-lactamases provided herein. In some embodiments, the present invention provides for the co-administration of one or more of the beta-lactamases described herein with other beta-lactamases known in the art. For example, the beta-lactamases described herein may be co-administered with one or more different beta-lactamase enzymes of class EC 3.5.2.6. In some embodiments, the beta-lactamases described herein may be co-administered with one or more of a group 1, 2, 3, or 4 beta-lactamase, in accordance with the functional classification scheme proposed by Bush et al. (1995, Antimicrob. Agents Chemother. 39: 1211-1233; the entire contents of which are incorporated herein by reference) or a class A, B, C, or D beta-lactamase, in accordance with the Ambler classification which divides beta-lactamases based on their amino acid sequences (Ambler 1980, Philos Trans R Soc Lond B Biol Sci. 289: 321-331; the entire contents of which are incorporated herein by reference).

In various embodiments, the beta-lactamases described herein may be co-administered with one or more beta-lactamase enzymes that inactive or hydrolyze penicillins and/or cephalosporins. In an embodiment, the beta-lactamases described herein may be co-administered with one or more beta-lactamases selected from P1A, P2A, or P4A. In an embodiment, the beta-lactamase is P1A or a derivative thereof. The P1A enzyme is a recombinant form of *Bacillus licheniformis* 749/C small exo beta-lactamase (see WO 2008/065247) which belongs to class A and is grouped to subgroup 2a in functional classification. *B. licheniformis* beta-lactamase and its P1A derivative are considered as penicillinases which have high hydrolytic capacity to degrade e.g. penicillin, ampicillin, amoxicillin or piperacillin and they are generally inhibited by active site-directed beta-lactamase inhibitors such as clavulanic acid, sulbactam or tazobactam. In another embodiment, the beta-lactamase is P3A or a derivative thereof as described, for example, in WO 2011/148041 and U.S. Provisional Patent Application Nos. 61/980,844 and 62/046,627, the entire contents of all of which are incorporated herein by reference. In a further embodiment, the beta-lactamase is P4A or a derivative thereof as described, for example, in U.S. Provisional Patent Application Nos. 61/980,844 and 62/046,627, the entire contents of all of which are incorporated herein by reference.

For all additional therapeutic agent compositions and methods, targeting to various parts of the GI tract may be employed as described herein.

In some embodiments, the present formulations and/or doses are administered to a patient to avoid treatment with an additional therapeutic agent. For example, in the context of preventing *C. difficile* infection (CDI) and/or a *C. difficile*-associated disease, the present formulations may be provided to a patient to avoid the necessity of receiving, for example, vancomycin.

Formulations

In one aspect, the present invention provides modified release formulations comprising at least one beta-lactamase, e.g. at the doses described herein, wherein the formulation releases a substantial amount of the beta-lactamase into one or more regions of the GI tract. In some embodiments, the beta-lactamase is P3A or a variant thereof (e.g. as described above). For example, the formulation may release at least about 60% of the beta-lactamase, for example, P3A, after the stomach and into one or more regions of the GI tract.

In various embodiments, the modified-release formulations of the present invention are designed for immediate release (e.g. upon ingestion). In various embodiments, the modified-release formulations may have sustained-release profiles, i.e. slow release of the active ingredient(s) in the body (e.g., GI tract) over an extended period of time. In various embodiments, the modified-release formulations may have a delayed-release profile, i.e. not immediately release the active ingredient(s) upon ingestion; rather, postponement of the release of the active ingredient(s) until the composition is lower in the gastrointestinal tract; for example, for release in the small intestine (e.g., one or more of duodenum, jejunum, ileum) or the large intestine (e.g., one or more of cecum, ascending, transverse, descending or sigmoid portions of the colon, and rectum). For example, a composition can be enteric coated to delay release of the active ingredient(s) until it reaches the small intestine or large intestine. In some embodiments, there is not a substantial amount of the active ingredient(s) of the present formulations in the stool.

In various embodiments, the modified-release formulation of the present invention releases at least 60% of the beta-lactamase (e.g. P3A or a variant thereof) after the stomach into one or more regions of the intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (e.g. P3A or a variant thereof) in the intestine, which may include the small intestine—inclusive of the duodenum, jejunum, ileum and/or the ileocecal junction—or the large intestine-inclusive of the cecum, ascending colon, transverse colon, descending colon, and sigmoid colon.

In various embodiments, the modified-release formulation does not substantially release the beta-lactamase (e.g. P3A or a variant thereof) in the stomach.

In certain embodiments, the modified-release formulation releases the beta-lactamase (e.g. P3A or a variant thereof) at a specific pH. For example, in some embodiments, the modified-release formulation is substantially stable in an acidic environment and substantially unstable (e.g., dissolves rapidly or is physically unstable) in a near neutral to alkaline environment. In some embodiments, stability is indicative of not substantially releasing while instability is indicative of substantially releasing. For example, in some embodiments, the modified-release formulation is substantially stable at a pH of about 7.0 or less, or about 6.5 or less, or about 6.0 or less, or about 5.5 or less, or about 5.0 or less, or about 4.5 or less, or about 4.0 or less, or about 3.5 or less, or about 3.0 or less, or about 2.5 or less, or about 2.0 or less, or about 1.5 or less, or about 1.0 or less. In some embodiments, the present formulations are stable in lower pH areas and therefore do not substantially release in, for example, the stomach. In some embodiments, modified-release formulation is substantially stable at a pH of about 1 to about 4 or lower and substantially unstable at pH values that are greater. In these embodiments, the modified-release formulation is not substantially released in the stomach. In these embodiments, the modified-release formulation is substantially released in the small intestine (e.g. one or more of the duodenum, jejunum, and ileum) and/or large intestine (e.g. one or more of the cecum, ascending colon, transverse colon, descending colon, and sigmoid colon). In some embodiments, modified-release formulation is substantially stable at a pH of about 4 to about 5 or lower and consequentially is substantially unstable at pH values that are greater and therefore is not substantially released in the stomach and/or small intestine (e.g. one or more of the duodenum, jejunum, and ileum). In these embodiments, the modified-release formulation is substantially released in the large intestine (e.g. one or more of the cecum, ascending colon, transverse colon, descending colon, and sigmoid colon). In various embodiments, the pH values recited herein may be adjusted as known in the art to account for the state of the subject, e.g. whether in a fasting or postprandial state.

In some embodiments, the modified-release formulation is substantially stable in gastric fluid and substantially unstable in intestinal fluid and, accordingly, is substantially released in the small intestine (e.g. one or more of the duodenum, jejunum, and ileum) and/or large intestine (e.g. one or more of the cecum, ascending colon, transverse colon, descending colon, and sigmoid colon).

In some embodiments, the modified-release formulation is stable in gastric fluid or stable in acidic environments. These modified-release formulations release about 30% or less by weight of the beta-lactamase (e.g. P3A or a variant thereof) and/or additional therapeutic agent in the modified-release formulation in gastric fluid with a pH of about 4 to about 5 or less, or simulated gastric fluid with a pH of about 4 to about 5 or less, in about 15, or about 30, or about 45, or about 60, or about 90 minutes. Modified-release formulations of the of the invention may release from about 0% to about 30%, from about 0% to about 25%, from about 0% to about 20%, from about 0% to about 15%, from about 0% to about 10%, about 5% to about 30%, from about 5% to about 25%, from about 5% to about 20%, from about 5% to about 15%, from about 5% to about 10% by weight of the beta-lactamase (e.g. P3A or a variant thereof) and/or additional therapeutic agent in the modified-release formulation in gastric fluid with a pH of 4-5, or less or simulated gastric fluid with a pH of 4-5 or less, in about 15, or about 30, or about 45, or about 60, or about 90 minutes. Modified-release formulations of the invention may release about 1%, about 2%, about 3%, about 4%, about 5%, about 6%, about 7%, about 8%, about 9%, or about 10% by weight of the total beta-lactamase (e.g. P3A or a variant thereof) and/or additional therapeutic agent in the modified-release formulation in gastric fluid with a pH of 5 or less, or simulated gastric fluid with a pH of 5 or less, in about 15, or about 30, or about 45, or about 60, or about 90 minutes.

In some embodiments, the modified-release formulation is unstable in intestinal fluid. These modified-release formulations release about 70% or more by weight of the beta-lactamase (e.g. P3A or a variant thereof) and/or additional therapeutic agent in the modified-release formulation in intestinal fluid or simulated intestinal fluid in about 15, or about 30, or about 45, or about 60, or about 90 minutes. In some embodiments, the modified-release formulation is unstable in near neutral to alkaline environments. These modified-release formulations release about 70% or more by weight of the beta-lactamase (e.g. P3A or a variant thereof) and/or additional therapeutic agent in the modified-release formulation in intestinal fluid with a pH of about 4-5 or greater, or simulated intestinal fluid with a pH of about 4-5 or greater, in about 15, or about 30, or about 45, or about 60, or about 90 minutes. A modified-release formulation that is unstable in near neutral or alkaline environments may release 70% or more by weight of beta-lactamase (e.g. P3A or a variant thereof) and/or additional therapeutic agent in the modified-release formulation in a fluid having a pH greater than about 5 (e.g., a fluid having a pH of from about 5 to about 14, from about 6 to about 14, from about 7 to about 14, from about 8 to about 14, from about 9 to about 14, from about 10 to about 14, or from about 11 to about 14) in from about 5 minutes to about 90 minutes, or from about 10 minutes to about 90 minutes, or from about 15 minutes to about 90 minutes, or from about 20 minutes to about 90 minutes, or from about 25 minutes to about 90 minutes, or from about 30 minutes to about 90 minutes, or from about 5 minutes to about 60 minutes, or from about 10 minutes to about 60 minutes, or from about 15 minutes to about 60 minutes, or from about 20 minutes to about 60 minutes, or from about 25 minutes to about 90 minutes, or from about 30 minutes to about 60 minutes.

In one embodiment, the modified-release formulation may remain essentially intact, or may be essentially insoluble, in gastric fluid. The stability of the delayed-release coating can be pH dependent. Delayed-release coatings that are pH dependent will be substantially stable in acidic environments (pH of about 5 or less), and substantially unstable in near neutral to alkaline environments (pH greater than about 5). For example, the delayed-release coating may essentially disintegrate or dissolve in near neutral to alkaline environments such as are found in the small intestine (e.g. one or more of the duodenum, jejunum, and ileum) and/or large intestine (e.g. one or more of the cecum, ascending colon, transverse colon, descending colon, and sigmoid colon).

Examples of simulated gastric fluid and simulated intestinal fluid include, but are not limited to, those disclosed in the 2005 Pharmacopeia 23NF/28USP in Test Solutions at page 2858 and/or other simulated gastric fluids and simulated intestinal fluids known to those of skill in the art, for example, simulated gastric fluid and/or intestinal fluid prepared without enzymes.

In various embodiments, the modified-release formulations comprising a beta-lactamase (e.g. P3A, or variants thereof) are substantially stable in chyme. For example, there is, in some embodiments, a loss of less about 50% or about 40%, or about 30%, or about 20%, or about 10% of beta-lactamase activity in about 10, or 9, or 8, or 7, or 6, or 5, or 4, or 3, or 2, or 1 hour from administration.

Alternatively, the stability of the modified-release formulation can be enzyme-dependent. Delayed-release coatings that are enzyme dependent will be substantially stable in fluid that does not contain a particular enzyme and substantially unstable in fluid containing the enzyme. The delayed-release coating will essentially disintegrate or dissolve in fluid containing the appropriate enzyme. Enzyme-dependent control can be brought about, for example, by using materials which release the active ingredient only on exposure to enzymes in the intestine, such as galactomannans. Also, the stability of the modified-release formulation can be dependent on enzyme stability in the presence of a microbial enzyme present in the gut flora.

In some embodiments, a dual pulse formulation is provided. In various embodiments, the present invention provides for modified-release formulations that release multiple doses of the beta-lactamase (e.g. P3A or a variant thereof), at different locations along the intestines, at different times, and/or at different pH. In an illustrative embodiment, the modified-release formulation comprises a first dose of the beta-lactamase and a second dose of the beta-lactamase, wherein the first dose and the second dose are released at different locations along the intestines, at different times, and/or at different pH. For example, the first dose is released at the duodenum, and the second dose is released at the ileum. In another example, the first dose is released at the jejunum, and the second dose is released at the ileum. In other embodiments, the first dose is released at a location along the small intestine (e.g., the duodenum), while the second dose is released along the large intestine (e.g., the ascending colon). In various embodiments, the modified-release formulation may release at least one dose, at least two doses, at least three doses, at least four doses, at least five doses, at least six doses, at least seven doses, or at least eight doses of the beta-lactamase (e.g. P3A or a variant thereof) at different locations along the intestines, at different times, and/or at different pH. Further the dual pulse description herein applies to modified-release formulations that release a beta-lactamase (e.g. P3A or a variant thereof) and an additional therapeutic agent.

In some dosage forms, the agents described herein are mixed with at least one inert, pharmaceutically acceptable excipient or carrier such as sodium citrate, dicalcium phosphate, etc., and/or a) fillers or extenders such as starches, lactose, sucrose, glucose, mannitol, silicic acid, microcrystalline cellulose, and Bakers Special Sugar, etc., b) binders such as, for example, carboxymethylcellulose, alginates, gelatin, polyvinylpyrrolidone, sucrose, acacia, polyvinyl alcohol, polyvinylpyrrolidone, methylcellulose, hydroxypropyl cellulose (HPC), and hydroxymethyl cellulose etc., c) humectants such as glycerol, etc., d) disintegrating agents such as agar-agar, calcium carbonate, potato or tapioca starch, alginic acid, certain silicates, sodium carbonate, cross-linked polymers such as crospovidone (cross-linked polyvinylpyrrolidone), croscarmellose sodium (cross-linked sodium carboxymethylcellulose), sodium starch glycolate, etc., e) solution retarding agents such as paraffin, etc., f) absorption accelerators such as quaternary ammonium compounds, etc., g) wetting agents such as, for example, cetyl alcohol and glycerol monostearate, etc., h) absorbents such as kaolin and bentonite clay, etc., and i) lubricants such as talc, calcium stearate, magnesium stearate, solid polyethylene glycols, sodium lauryl sulfate, glyceryl behenate, etc., and mixtures of such excipients. One of skill in the art will recognize that particular excipients may have two or more functions in the oral dosage form. In the case of an oral dosage form, for example, a capsule or a tablet, the dosage form may also comprise buffering agents.

The modified release formulation can additionally include a surface active agent. Surface active agents suitable for use in the present invention include, but are not limited to, any pharmaceutically acceptable, non-toxic surfactant. Classes of surfactants suitable for use in the compositions of the invention include, but are not limited to polyethoxylated fatty acids, PEG-fatty acid diesters, PEG-fatty acid mono- and di-ester mixtures, polyethylene glycol glycerol fatty acid esters, alcohol-oil transesterification products, polyglycerized fatty acids, propylene glycol fatty acid esters, mixtures of propylene glycol esters-glycerol esters, mono- and diglycerides, sterol and sterol derivatives, polyethylene glycol sorbitan fatty acid esters, polyethylene glycol alkyl ethers, sugar esters, polyethylene glycol alkyl phenols, polyoxyethylene-olyoxypropylene block copolymers, sorbitan fatty acid esters, lower alcohol fatty acid esters, ionic surfactants, and mixtures thereof. In some embodiments, compositions of the invention may comprise one or more surfactants including, but not limited to, sodium lauryl sulfate, polysorbate 20, polysorbate 40, polysorbate 60, polysorbate 80, and triethyl citrate.

The modified-release formulation can also contain pharmaceutically acceptable plasticizers to obtain the desired mechanical properties such as flexibility and hardness. Such plasticizers include, but are not limited to, triacetin, citric acid esters, triethyl citrate, phthalic acid esters, dibutyl sebacate, cetyl alcohol, polyethylene glycols, polysorbates or other plasticizers.

The modified-release formulation can also include one or more application solvents. Some of the more common solvents that can be used to apply, for example, a delayed-release coating composition include isopropyl alcohol, acetone, methylene chloride and the like.

The modified-release formulation can also include one or more alkaline materials. Alkaline material suitable for use in compositions of the invention include, but are not limited to, sodium, potassium, calcium, magnesium and aluminum salts of acids such as phosphoric acid, carbonic acid, citric acid and other aluminum/magnesium compounds. In addition the alkaline material may be selected from antacid materials such as aluminum hydroxides, calcium hydroxides, magnesium hydroxides and magnesium oxide.

The solid oral dosage forms can be prepared by, for example granulation (e.g., wet or dry granulation) of the agents of the invention with one or more suitable excipients. Alternatively, the agents of the invention can be layered onto an inert core (e.g., a nonpareil/sugar sphere such as a sucrose sphere or silica sphere) using conventional methods such as fluidized bed or pan coating, or extruded and spheronized using methods known in the art, into active compound-containing beads or pellets. Such beads or pellets can then be incorporated into tablets or capsules using conventional methods.

Besides inert diluents, the oral compositions can also include adjuvants such as sweetening, flavoring, and perfuming agents.

Suspensions, in addition to the active agents, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

The formulations comprising the beta-lactamase (and/or additional therapeutic agents) may conveniently be presented in unit dosage forms, e.g. using the doses provided herein, and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art).

In various embodiments, the invention provides a formulation comprising: a core particle having a base coat comprising one or more beta-lactamases (e.g., P3A or a variant thereof), and a delayed-release coating disposed over the coated core particle. The delayed-release coating may be substantially stable in acidic environments and/or gastric fluid, and/or substantially unstable in near neutral to alkaline environments or intestinal fluid thereby exposing the coated core particle to intestinal fluid. The base coat comprising one or more beta-lactamases may further comprise one or more additional therapeutic agents. Optionally a plurality of base coats may be applied to the core each of which may contain a beta-lactamase and/or an additional therapeutic agent. In an embodiment, the core particle includes sucrose. The formulation can be prepared by methods known in the art. For example, a beta-lactamases (e.g., P3A or a variant thereof) can be sprayed onto an inert core (e.g., a sucrose core) and spray-dried with an enteric layer (e.g., Eudragit L30 D-55) to form P3A containing pellets.

Optionally, the core particle may comprise one or more beta-lactamases (e.g., P3A or a variant thereof) and/or one or more additional therapeutic agents. In one embodiment, one or more doses of the beta-lactamase may be encapsulated in a core particle, for example, in the form of a microsphere. For example, the beta-lactamase may be combined with a polymer (e.g., latex), and then formed into a particulate, micro-encapasulated enzyme preparation, without using a sucrose core. The microspheres thus formed may be optionally covered with a delayed-release coating.

A variety of approaches for generating particulates (such as microspheres, aggregates, other) are known which are amenable to the inclusion of proteins. They typically involve at least two phases, one containing the protein, and one containing a polymer that forms the backbone of the particulate. Most common are coacervation, where the polymer is made to separate from its solvent phase by addition of a third component, or multiple phase emulsions, such as water in oil in water (w/o/w) emulsion where the inner water phase contains the protein, the intermediate organic phase contains the polymer, and the external water phase stabilizers that support the w/o/w double emulsion until the solvents can be removed to form the microspheres. Alternatively, the beta-lactamase (e.g., P3A or variants thereof) and stabilizing excipients (for example, trehalose, mannitol, Tween 80, polyvinyl alcohol) are combined and sprayed from aqueous solution and collected. The particles are then suspended in a dry, water immiscible organic solvent containing polymer and release modifying compounds, and the suspension sonicated to disperse the particles. An additional approach uses aqueous phases but no organic solvent. Specifically, the enzyme, buffer components, a polymer latex, and stabilizing and release-modifying excipients are dissolved/dispersed in water. The aqueous dispersion is spray-dried, leading to coalescence of the latex, and incorporation of the protein and excipients in particles of the coalesced latex. When the release modifiers are insoluble at acidic conditions but soluble at higher pHs (such as carboxylic acid) then release from the matrix is inhibited in the gastric environment.

In various embodiments, the formulation may comprise a plurality of modified-release particles or pellets or microspheres. In one embodiment, the formulation is in the form of capsules comprising multiple pellets. In one embodiment, the formulation is in the form of capsules comprising multiple microspheres.

In various embodiments, the modified-release formulation of the present invention may utilize one or more modified-release coatings such as delayed-release coatings to provide for effective, delayed yet substantial delivery of the beta-lactamase to the GI tract together with, optionally, additional therapeutic agents.

In one embodiment, the delayed-release coating includes an enteric agent that is substantially stable in acidic environments and substantially unstable in near neutral to alkaline environments. In an embodiment, the delayed-release coating contains an enteric agent that is substantially stable in gastric fluid. The enteric agent can be selected from, for example, solutions or dispersions of methacrylic acid copolymers, cellulose acetate phthalate, hydroxypropylmethyl cellulose phthalate, polyvinyl acetate phthalate, carboxymethylethylcellulose, and EUDRAGIT®-type polymer (poly(methacrylic acid, methylmethacrylate), hydroxypropyl methylcellulose acetate succinate, cellulose acetate trimellitate, shellac or other suitable enteric coating polymers. The EUDRAGIT®-type polymer include, for example, EUDRAGIT® FS 30D, L 30 D-55, L 100-55, L 100, L 12.5, L 12.5 P, RL 30 D, RL P0, RL 100, RL 12.5, RS 30 D, RS P0, RS 100, RS 12.5, NE 30 D, NE 40 D, NM 30 D, S 100, S 12.5, and S 12.5 P. In some embodiments, one or more of EUDRAGIT® FS 30D, L 30 D-55, L 100-55, L 100, L 12.5, L 12.5 P RL 30 D, RL P0, RL 100, RL 12.5, RS 30 D, RS P0, RS 100, RS 12.5, NE 30 D, NE 40 D, NM 30 D, S 100, S 12.5 and S 12.5 P is used. The enteric agent may be a combination of the foregoing solutions or dispersions.

In another embodiment, the delayed-release coating may degrade as a function of time when in aqueous solution without regard to the pH and/or presence of enzymes in the solution. Such a coating may comprise a water insoluble polymer. Its solubility in aqueous solution is therefore independent of the pH. The term "pH independent" as used herein means that the water permeability of the polymer and its ability to release pharmaceutical ingredients is not a function of pH and/or is only very slightly dependent on pH. Such coatings may be used to prepare, for example, sustained release formulations. Suitable water insoluble polymers include pharmaceutically acceptable non-toxic polymers that are substantially insoluble in aqueous media, e.g., water, independent of the pH of the solution. Suitable polymers include, but are not limited to, cellulose ethers, cellulose esters, or cellulose ether-esters, i.e., a cellulose derivative in which some of the hydroxy groups on the cellulose skeleton are substituted with alkyl groups and some are modified with alkanoyl groups. Examples include ethyl cellulose, acetyl cellulose, nitrocellulose, and the like. Other examples of insoluble polymers include, but are not limited to, lacquer, and acrylic and/or methacrylic ester polymers, polymers or copolymers of acrylate or methacrylate having a low quaternary ammonium content, or mixture thereof and the like. Other examples of insoluble polymers include EUDRAGIT RS®, EUDRAGIT RL®, and EUDRAGIT NE®. Insoluble polymers useful in the present invention include polyvinyl esters, polyvinyl acetals, polyacrylic acid esters, butadiene styrene copolymers, and the like. In one embodiment, colonic delivery is achieved by use of a slowly-eroding wax plug (e.g., various PEGS, including for example, PEG6000).

In a further embodiment, the delayed-release coating may be degraded by a microbial enzyme present in the gut flora. In one embodiment, the delayed-release coating may be degraded by a bacteria present in the small intestine. In another embodiment, the delayed-release coating may be degraded by a bacteria present in the large intestine.

In some embodiments, before applying the delayed-release coating to the coated core particle the particle can optionally be covered with one or more separating layers comprising pharmaceutical excipients including alkaline compounds such as for instance pH-buffering compounds. The separating layer essentially separates the coated core particle from the delayed-release coating.

The separating layer can be applied to the coated core particle by coating or layering procedures typically used with coating equipment such as a coating pan, coating granulator or in a fluidized bed apparatus using water and/or organic solvents for the coating process. As an alternative the separating layer can be applied to the core material by using a powder coating technique. The materials for separating layers are pharmaceutically acceptable compounds such as, for instance, sugar, polyethylene glycol, polyvinylpyrrolidone, polyvinyl alcohol, polyvinyl acetate, hydroxypropyl cellulose, methyl-cellulose, ethylcellulose, hydroxypropyl methylcellulose, carboxymethylcellulose sodium and others, used alone or in mixtures. Additives such as plasticizers, colorants, pigments, fillers, anti-tacking and anti-static agents, such as for instance magnesium stearate, titanium dioxide, talc and other additives can also be included in the separating layer.

In some embodiments, the coated particles with the delayed-release coating may be further covered with an overcoat layer. The overcoat layer can be applied as described for the other coating compositions. The overcoat materials are pharmaceutically acceptable compounds such as sugar, polyethylene glycol, polyvinylpyrrolidone, polyvinyl alcohol, polyvinyl acetate, hydroxypropyl cellulose, methylcellulose, ethylcellulose, hydroxypropyl methylcellulose, carboxymethylcellulose sodium and others, used alone or in mixtures. The overcoat materials can prevent potential agglomeration of particles coated with the delayed-release coating, protect the delayed-release coating from cracking during the compaction process or enhance the tableting process.

In some embodiments, the present invention contemplates the administration of a modified-release formulation of beta-lactamase as disclosed, for example, in PCT/US2015/054606, the entire contents of which are hereby incorporated by reference. In such embodiments, the formulation may comprise a plurality of modified-release particles or pellets or microspheres. In one embodiment, the formulation is in the form of capsules comprising multiple pellets. In one embodiment, the formulation is in the form of capsules comprising multiple microspheres. In an embodiment, the formulation comprising the beta-lactamase containing pellets or beads may release the beta-lactamase at a pH of about 5.5.

In some embodiments, the modified-release formulation is a capsule filled with a plurality of beta-lactamase-containing pellets (e.g., P3A (or the other beta-lactamase agents described herein, and variants thereof)—containing pellets) from which the beta-lactamase is released. In an embodiment, the capsule is a gelatin capsule, such as a hard gelatin capsule. In another embodiment, the capsule is a hydroxypropyl methylcellulose (HPMC) capsule. For example, the formulation may be in the form of capsules comprising multiple pellets. For example, the formulation may be in the form of capsules such as, for example, gelatin or hydroxypropyl methylcellulose (HPMC) capsules comprising multiple enteric-coated pellets containing beta-lactamase (e.g. P3A, or the other beta-lactamase agents described herein, and variants thereof). In such an embodiment, a combination of pellets may be utilized in which each pellet is designed to release at a specific time point or location. In various embodiments, the pellets (e.g., enteric-coated pellets) are designed to pass through the stomach unchanged and then release the beta-lactamase (e.g. P3A, or the other beta-lactamase agents described herein, and variants thereof) into one or more regions of the intestines. In some embodiments, the beta-lactamase-containing pellets may be enteric-coated to release the beta-lactamase (e.g. P3A, or the other beta-lactamase agents described herein, and variants thereof) at different intestinal pH values.

In various embodiments, the formulation of the present invention is in the form of a capsule (e.g., a hard gelatin or HPMC capsule) comprising a plurality of enteric-coated beta-lactamase-containing pellets. In such embodiments, the pellets (or each individual pellet) comprise a beta-lactamase (e.g. P3A, or the other beta-lactamase agents described herein, and variants thereof), a sucrose sphere, which the beta-lactamase, for example, P3A or a variant, is sprayed onto, a binder excipient (e.g., hydroxypropylcellulose (HPC)), an enteric polymer (e.g., EUDRAGIT L 30 D-55), a plasticizer (e.g., triethyl citrate), a glidant (e.g., glyceryl monostearate), an emulsifier, and buffer salts.

In various embodiments, the formulation of the present invention is in the form of a capsule (e.g., a hard gelatin or HPMC capsule) comprising a plurality of enteric-coated beta-lactamase-containing pellets. In such embodiments, the pellets (or each individual pellet) comprise about 10-20% by weight of beta-lactamase (e.g. P3A, or the other beta-lactamase agents described herein, and variants thereof). For example, the beta-lactamase (e.g. P3A, or the other beta-lactamase agents described herein, and variants thereof) may be present at about 10%, about 11%, about 12%, about 13%, about 14%, about 15%, about 16%, about 17%, about 18%, about 19%, or about 20% by weight. In some embodiments, the pellets (or each individual pellet) comprise about 20-30% by weight sucrose sphere, which the beta-lactamase, for example, P3A or a variant, is sprayed onto. For example, the sucrose sphere may be present at about 20%, about 21%, about 22%, about 23%, about 24%, about 25%, about 26%, about 27%, about 28%, about 29%, or about 30% by weight. In various embodiments, the pellets (or each individual pellet) comprise about 30-40% by weight a binder excipient (e.g., hydroxypropylcellulose (HPC)). For example, the binder excipient may be present at about 30%, about 31%, about 32%, about 33%, about 34%, about 35%, about 36%, about 37%, about 38%, about 39%, or about 40% by weight. In some embodiments, the pellets (or each individual pellet) comprise about 15-25% by weight an enteric polymer (e.g., EUDRAGIT L 30 D-55). For example, the enteric polymer may be present at about 15%, about 16%, about 17%, about 18%, about 19%, about 20%, about 21%, about 22%, about 23%, about 24%, or about 25% by weight. In some embodiments, the pellets (or each individual pellet) comprise about 1.5-2.5% by weight of plasticizer (e.g., triethyl citrate). For example, the plasticizer may be present at about 1.5%, about 1.6%, about 1.7%, about 1.8%, about 1.9%, about 2%, about 2.1%, about 2.2%, about 2.3%, about 2.4%, about 2.5% by weight. In some embodiments, the pellets (or each individual pellet) comprise about 0.5-1.5% by weight glidant (e.g., glyceryl monostearate). For example, the glidant may be present at about 0.5%, about 0.6%, about 0.7%, about 0.8%, about 0.9%, about 1%, about 1.1%, about 1.2%, about 1.3%, about 1.4%, or about 1.5% by weight. In some embodiments, the pellets (or each individual pellet) comprise about 0.1-1.0% by weight emulsifier (e.g. polysorbate-80). For example, the emulsifier may be present at about 0.1%, about 0.2%, about 0.3%, about 0.4%, about 0.5%, about 0.6%, about 0.7%, about 0.8%, about 0.9%, or about 1% by weight. In some embodiments, the pellets (or each individual pellet) further comprise about 1-2% by weight buffer salts. For example, the buffer salts may be present at about 1.1%, about 1.2%, about 1.3%, about 1.4%, about 1.5%, about 1.6%, about 1.7%, about 1.8%, about 1.9%, or about 2% by weight. The weight as described herein refers to the total weight of all components excluding the weight of the capsule itself.

In some embodiments, the pellets (or each individual pellet) comprise about 16% by weight of the beta-lactamase (e.g. P3A, or the other beta-lactamase agents described herein, and variants thereof); about 23% by weight sucrose sphere; about 35% by weight a binder excipient (e.g., hydroxypropylcellulose (HPC)); about 21% by weight an enteric polymer (e.g., EUDRAGIT L 30 D-55); about 2% by weight of plasticizer (e.g., triethyl citrate); about 1% by weight glidant (e.g., glyceryl monostearate); about 0.5% by weight emulsifier (e.g. polysorbate-80); and about 2% by weight buffer salts. The weight as described herein refers to the total weight of all components excluding the weight of the capsule itself.

For example, the pellets (or each individual pellet) comprise about 15.8% by weight of the beta-lactamase (e.g. P3A, or the other beta-lactamase agents described herein, and variants thereof); about 23.3% by weight sucrose sphere; about 35% by weight a binder excipient (e.g., hydroxypropylcellulose (HPC)); about 20.8% by weight an enteric polymer (e.g., EUDRAGIT L 30 D-55); about 2.1% by weight of plasticizer (e.g., triethyl citrate); about 1.0% by weight glidant (e.g., glyceryl monostearate); about 0.4% by weight emulsifier (e.g. polysorbate-80); and about 1.6% by weight buffer salts. The weight as described herein refers to the total weight of all components excluding the weight of the capsule itself.

In various embodiments, the formulation of the present invention is in the form of a capsule (e.g., a hard gelatin or HPMC capsule) comprising about 75 mg of the beta-lactamase (e.g. P3A, or the other beta-lactamase agents described herein, and variants thereof). The capsule includes a plurality of enteric-coated beta-lactamase-containing pellets. In such embodiments, the formulation comprises about 10-20% by weight of the beta-lactamase (e.g. P3A, or the other beta-lactamase agents described herein, and variants thereof). For example, the beta-lactamase (e.g. P3A, or the other beta-lactamase agents described herein, and variants thereof) may be present at about 10%, about 11%, about 12%, about 13%, about 14%, about 15%, about 16%, about 17%, about 18%, about 19%, or about 20% by weight. In some embodiments, the formulation comprises about 15-25% by weight sucrose sphere. For example, the sucrose sphere may be present about 15%, about 16%, about 17%, about 18%, about 19%, about 20%, about 21%, about 22%, about 23%, about 24%, or about 25% by weight. In various embodiments, the formulation comprises about 25-35% by weight a binder excipient (e.g., hydroxypropylcellulose (HPC)). For example, the binder excipient may be present at about 25%, about 26%, about 27%, about 28%, about 29%, about 30%, about 31%, about 32%, about 33%, about 34%, or about 35% by weight. In some embodiments, the formulation comprises about 10-25% by weight an enteric polymer (e.g., EUDRAGIT L 30 D-55). For example, the enteric polymer may be present at about 10%, about 11%, about 12%, about 13%, about 14%, about 15%, about 16%, about 17%, about 18%, about 19%, about 20%, about 21%, about 22%, about 23%, about 24%, or about 25% by weight. In some embodiments, the formulation comprises about 1.5-2.5% by weight of plasticizer (e.g., triethyl citrate). For example, the plasticizer may be present at about 1.5%, about 1.6%, about 1.7%, about 1.8%, about 1.9%, about 2%, about 2.1%, about 2.2%, about 2.3%, about 2.4%, about 2.5% by weight. In some embodiments, the formulation comprises about 0.5-1.5% by weight glidant (e.g., glyceryl monostearate). For example, the glidant may be present at about 0.5%, about 0.6%, about 0.7%, about 0.8%, about 0.9%, about 1%, about 1.1%, about 1.2%, about 1.3%, about 1.4%, or about 1.5% by weight. In some embodiments, the formulation comprises about 0.1-1.0% by weight emulsifier (e.g. polysorbate-80). For example, the emulsifier may be present at about 0.1%, about 0.2%, about 0.3%, about 0.4%, about 0.5%, about 0.6%, about 0.7%, about 0.8%, about 0.9%, or about 1% by weight. In some embodiments, the formulation comprises about 1-2% by weight buffer salts. For example, the buffer salts may be present at about 1%, about 1.1%, about 1.2%, about 1.3%, about 1.4%, about 1.5%, about 1.6%, about 1.7%, about 1.8%, about 1.9%, or about 2% by weight. In some embodiments, the formulation comprises about 10-20% by weight gelatin or HPMC capsule. For example, the gelatin or HPMC capsule may be about 10%, about 11%, about 12%, about 13%, about 14%, about 15%, about 16%, about 17%, about 18%, about 19%, or about 20% by weight.

In some embodiments, the formulation of the present invention comprising about 75 mg of the beta-lactamase (e.g. P3A, or the other beta-lactamase agents described herein, and variants thereof). In such embodiments, the formulation comprises about 13% by weight of the beta-lactamase (e.g. P3A, or the other beta-lactamase agents described herein, and variants thereof); about 19% by weight sucrose sphere; about 29% by weight a binder excipient (e.g., hydroxypropylcellulose (HPC)); about 17% by weight an enteric polymer (e.g., EUDRAGIT L 30 D-55); about 2% by weight of plasticizer (e.g., triethyl citrate); about 1% by weight glidant (e.g., glyceryl monostearate); about 0.5% by weight emulsifier (e.g. polysorbate-80); about 1% by weight buffer salts; and about 17% by weight gelatin or HPMC capsule.

For example, the formulation comprises about 13.1% by weight of the beta-lactamase (e.g. P3A, or the other beta-lactamase agents described herein, and variants thereof); about 19.4% by weight sucrose sphere; about 29.1% by weight a binder excipient (e.g., hydroxypropylcellulose (HPC)); about 17.3% by weight an enteric polymer (e.g., EUDRAGIT L 30 D-55); about 1.7% by weight of plasticizer (e.g., triethyl citrate); about 0.9% by weight glidant (e.g., glyceryl monostearate); about 0.4% by weight emulsifier (e.g. polysorbate-80); about 1.3% by weight buffer salts; and about 16.8% by weight gelatin or HPMC capsule.

In various embodiments, the formulation of the present invention is in the form of a capsule (e.g., a hard gelatin or HPMC capsule) comprising about 25 mg of the beta-lactamase (e.g. P3A, or the other beta-lactamase agents described herein, and variants thereof). The capsule includes a plurality of enteric-coated beta-lactamase-containing pellets. In such embodiments, the formulation comprises about 5-15% by weight of the beta-lactamase (e.g. P3A, or the other beta-lactamase agents described herein, and variants thereof). For example, the beta-lactamase (e.g. P3A, or the other beta-lactamase agents described herein, and variants thereof) may be present at about 5%, about 6%, about 7%, about 8%, about 9%, about 10%, about 11%, about 12%, about 13%, about 14%, or about 15% by weight. In some embodiments, the formulation comprises about 10-20% by weight sucrose sphere. For example, the sucrose sphere may be present about 10%, about 11%, about 12%, about 13%, about 14%, about 15%, about 16%, about 17%, about 18%, about 19%, or about 20% by weight. In various embodiments, the formulation comprises about 15-25% by weight a binder excipient (e.g., hydroxypropylcellulose (HPC)). For example, the binder excipient may be present at about 15%, about 16%, about 17%, about 18%, about 19%, about 20%, about 21%, about 22%, about 23%, about 24%, or about 25% by weight. In some embodiments, the formulation comprises about 10-20% by weight an enteric polymer (e.g., EUDRAGIT L 30 D-55). For example, the enteric polymer may be present at about 10%, about 11%, about 12%, about 13%, about 14%, about 15%, about 16%, about 17%, about 18%, about 19%, or about 20% by weight. In some embodiments, the formulation comprises about 1.0-2.0% by weight of plasticizer (e.g., triethyl citrate). For example, the plasticizer may be present at about 1.0%, about 1.1%, about 1.2%, about 1.3%, about 1.4%, about 1.5%, about 1.6%, about 1.7%, about 1.8%, about 1.9%, or about 2.0% by weight. In some embodiments, the formulation comprises about 0.1-1.0% by weight glidant (e.g., glyceryl monostearate). For example, the glidant may be present at about 0.1%, about 0.2%, about 0.3%, about 0.4%, about 0.5%, about 0.6%, about 0.7%, about 0.8%, about 0.9%, or about 1% by weight. In some embodiments, the formulation comprises about 0.1-1.0% by weight emulsifier (e.g. polysorbate-80). For example, the emulsifier may be present at about 0.1%, about 0.2%, about 0.3%, about 0.4%, about 0.5%, about 0.6%, about 0.7%, about 0.8%, about 0.9%, or about 1% by weight. In some embodiments, the formulation comprises about 0.5-1.5% by weight buffer salts. For example, the buffer salts may be present at about 0.5%, about 0.6%, about 0.7%, about 0.8%, about 0.9%, about 1.0%, about 1.1%, about 1.2%, about 1.3%, about 1.4%, or about 1.5% by weight. In some embodiments, the formulation comprises about 30-40% by weight gelatin or HPMC capsule. For example, the gelatin or HPMC capsule may be about 30%, about 31%, about 32%, about 33%, about 34%, about 35%, about 36%, about 37%, about 38%, about 39%, or about 40% by weight.

In some embodiments, the formulation of the present invention comprising about 25 mg of the beta-lactamase (e.g. P3A, or the other beta-lactamase agents described herein, and variants thereof). In such embodiments, the formulation comprises about 10% by weight of the beta-lactamase (e.g. P3A, or the other beta-lactamase agents described herein, and variants thereof); about 15% by weight sucrose sphere; about 22% by weight a binder excipient (e.g., hydroxypropylcellulose (HPC)); about 13% by weight an enteric polymer (e.g., EUDRAGIT L 30 D-55); about 1% by weight of plasticizer (e.g., triethyl citrate); about 0.5% by weight glidant (e.g., glyceryl monostearate); about 0.3% by weight emulsifier (e.g. polysorbate-80); about 1% by weight buffer salts; and about 38% by weight gelatin or HPMC capsule.

For example, the formulation comprises about 9.8% by weight of the beta-lactamase (e.g. P3A, or the other beta-lactamase agents described herein, and variants thereof); about 14.5% by weight sucrose sphere; about 21.8% by weight a binder excipient (e.g., hydroxypropylcellulose (HPC)); about 13% by weight an enteric polymer (e.g., EUDRAGIT L 30 D-55); about 1.3% by weight of plasticizer (e.g., triethyl citrate); about 0.6% by weight glidant (e.g., glyceryl monostearate); about 0.3% by weight emulsifier (e.g. polysorbate-80); about 1.0% by weight buffer salts; and about 37.7% by weight gelatin or HPMC capsule.

The present invention also provides for modified-release formulations that release multiple doses of the beta-lactamases (e.g., P3A or a variant thereof) and/or additional therapeutic agent along the gastrointestinal tract. The overall release profile of such a formulation may be adjusted by utilizing, for example, multiple particle types or multiple layers. In one embodiment, the first dose of the beta-lactamase may be formulated for release in, for example, the small intestine (e.g., one or more of duodenum, jejunum, ileum) or the large intestine (e.g., one or more of cecum, ascending, transverse, descending or sigmoid portions of the colon, and rectum), whereas the second dose is formulated for delayed release in, for example, the small intestine (e.g., one or more of duodenum, jejunum, ileum) or the large intestine (e.g., one or more of cecum, ascending, transverse, descending or sigmoid portions of the colon, and rectum). Alternatively, multiple doses are released at different locations along the intestine. For example, in one embodiment, the first dose of the beta-lactamase may be formulated for release in, for example, the small intestine (e.g., one or more of duodenum, jejunum, ileum), whereas the second dose is formulated for delayed release in, for example, another part of the small intestine (e.g., one or more of duodenum, jejunum, ileum). In another embodiment, the first dose of the beta-lactamase may be formulated for release in, for example, the large intestine (e.g., one or more of cecum, ascending, transverse, descending or sigmoid portions of the colon, and rectum), whereas the second dose is formulated for delayed release in, for example, another part of the large intestine (e.g., one or more of cecum, ascending, transverse, descending or sigmoid portions of the colon, and rectum).

Furthermore, in various embodiments, the agents described herein may be in the form of a pharmaceutically acceptable salt, namely those salts which are suitable for use in contact with the tissues of humans and other animals without undue toxicity, irritation, allergic response and the like, and are commensurate with a reasonable benefit/risk ratio. Pharmaceutically acceptable salts are well known in the art. The salts can be prepared in situ during the final isolation and purification of the therapeutic agents, or separately by reacting the free base function with a suitable acid or a free acid functionality with an appropriate alkaline moiety. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Kits

The invention provides kits that can simplify the administration of any agent described herein. An illustrative kit of the invention comprises any composition described herein in unit dosage form. In one embodiment, the unit dosage form is a container, such as a pre-filled syringe or a pill bottle or a blister pack, which can be sterile, containing any agent described herein and a pharmaceutically acceptable carrier, diluent, excipient, or vehicle. The kit can further comprise a label or printed instructions instructing the use of any agent described herein. The kit can also further comprise one or more additional therapeutic agents described herein. In one embodiment, the kit comprises a container containing an effective amount of a composition of the invention and an effective amount of another composition, such those described herein.

In one embodiment, the invention provides a kit for use in a patient susceptible to one or more infections, comprising a pharmaceutical composition comprising a beta-lactamase comprises an amino acid sequence having at least 95% identity with SEQ ID NO: 1 in a unit dosage form of between about 1 mg and about 1,000 mg and optionally one or more beta-lactam antibiotics, optionally selected from a penicillin and a cephalosporin. In an embodiment, the kit further comprises a proton pump inhibitor.

EXAMPLES

Example 1: Manufacturing of P3A Delayed-Release Pellets and Capsules

A P3A formulation including P3A enteric-coated pellets was produced. To produce the pellets, P3A was spray-coated onto a sucrose core and spray-dried with an enteric layer, Eudragit L30 D-55, to protect the P3A active pharmaceutical ingredient from the acidic conditions of the stomach. The Eudragit L30 D55 polymer begins to depolymerize when the pH rises to 5.5 and above in the small intestine, thus releasing the active drug from the pellet.

Figure 1A:
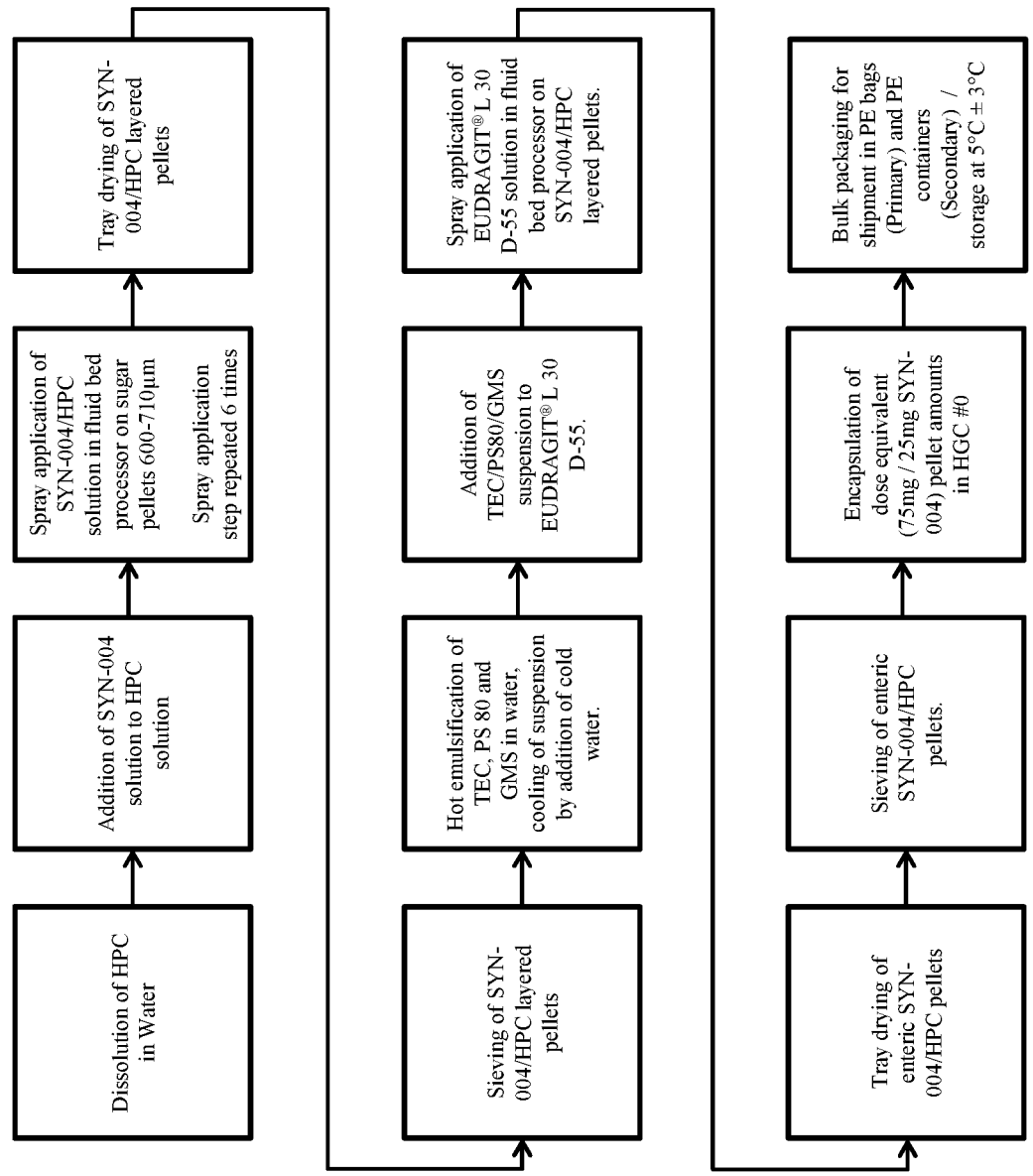
FIG. 1A depicts an embodiment of a manufacturing process for producing P3A delayed-release capsules used in the clinical studies described here.

Delayed-release capsules including the P3A entericcoated pellets were manufactured in a GMP process as depicted in FIG. 1A. Specifically, the GMP manufacture of P3A Delayed-Release Capsule was a three stage sequential process including: 1) P3A drug layering onto sucrose core pellets by spray application, 2) enteric coating with EUDRAGIT® L 30 D-55 using spray application, and 3) encapsulation of pellets into hard gelatin capsules size 0.

P3A layered pellets were produced by spray application of P3A drug substance using hydroxypropylcellulose (HPC) as a binder excipient, water as a solvent, and sucrose spheres as starting material. The spray application was performed using a fluid bed system over six work shifts, in order to achieve a final active pharmaceutical agent (API) percentage of at least 15%. After the sixth work shift of spray application of the P3A/HPC mixture, the P3A layered pellets were dried overnight at room temperature on trays, then sifted through a 1.4 mm sieve prior to bulk packaging in polyethylene (PE) bags and PE containers. The drug-layered pellets were stored at 5±3° C. for further processing. It is notes that attempts to use hydroxymethylcellulose (HMC) as a binder excipient were unsuccessful as this produced flaky pellets that could not be furthered processed (e.g. spray dried).

In a subsequent process, the P3A layered pellets were coated with methacrylic acid ethyl acrylate copolymer (EUDRAGIT® L 30 D-55) as an enteric polymer, triethyl citrate as a plasticizer, glyceryl monostearate as a glidant, polysorbate-80 as an emulsifier, and water as a diluent. The coating was performed using a fluid bed system in a single work shift. The enteric coated P3A layered pellets were dried overnight at room temperature on trays and sifted through a 1.6 mm sieve prior to packaging as bulk pellets in PE bags and PE containers. The enteric coated P3A layered pellets were stored at 5±3° C. for further processing.

The enteric coated P3A layered pellets were encapsulated in hard gelatin capsules using an automated capsule filler with a capsule transport and dosing unit for filling size 0 capsules. The final P3A delayed-release capsules, 75 mg, were packed as bulk Drug Product in PE bags and PE containers, and stored at 5±3° C. ready for shipment.

In a separate manual process to manufacture P3A delayed-release capsules, 25 mg, the enteric P3A layered pellets were encapsulated in hard gelatin capsules using an analytical balance, capsule filling funnel for filling size 0 capsules. The final P3A delayed-release capsule, 25 mg were packed as bulk Drug Product in PE bags and PE containers, and stored at 5±3° C. ready for shipment.

P3A delayed-release capsules, intended for use in clinical trials and stability studies, were packaged in a 100 cc high density polyethylene (HDPE) round bottle with 38 mm polypropylene (PP) child resistant closures, with an induction seal.

During manufacturing, a list of in-process controls, as shown in the table below, were employed for the P3A delayed-release capsules, 75 mg and 25 mg. These tests were performed on manufactured P3A delayed-release pellets prior to encapsulation.

| P3A Delayed-Release Capsule Manufacturing In-Process Controls | | | |
|---|---|---|---|
| Test | In-Process Step | Test Method | Specification |
| Appearance | Post-enteric coating | Visual | White to slightly yellowish, spherical and evenly sized, free flowing |
| Particle Size Distribution | Post-enteric coating | USP | Reported |
| Biological Activity by CENTA Assay | Post-enteric coating | QKY24701 | 12.6-19.0% (80-120% label claim) |

As a control, placebo capsules containing placebo buffer were also produced using an essentially identical process as the P3A delayed-release capsules. Specifically, the placebo capsules were manufactured according to the batch records similar to the P3A delayed-release capsule, 75 mg drug product.

The final placebo capsules were packed as bulk product in PE bags and PE containers, and stored at 5±3° C. ready for shipment. The placebo capsules intended for use in clinical trials were packaged in a 100 cc HDPE round bottle with 38 mm PP child resistant closures, with an induction seal During manufacturing of the placebo capsules, a list of in-process controls, as shown in the table below, were also employed. The tests were performed on the placebo pellets prior to encapsulation.

| P3A Placebo Capsule Manufacturing In-Process Controls | | | |
|---|---|---|---|
| Test | In-Process Step | Test Method | Specification |
| Appearance | Post-enteric coating | Visual | White to slightly yellowish, spherical and evenly sized, free flowing |
| Particle Size Distribution | Post-enteric coating | USP | Reported |
| Biological Activity by CENTA Assay | Post-enteric coating | QKY24701 | ≤Limit of Detection (<1% of label claim) |

In addition, a non-GMP batch of P3A Delayed-Release pellets was manufactured for nonclinical use using the same process flow as described in FIG. 1A, with the exception of the final encapsulation of pellets by the manufacturer. Instead, bulk P3A delayed-release pellets were tested and stored in bulk. Subsequent to the release testing for nonclinical use, the non-GMP batch was encapsulated in size 0 hard gelatin capsules and placed on a stability study

Example 2: Composition and Appearance of P3A Delayed-Release Pellets and Capsules The P3A dosage form is a hard gelatin capsule or a hydroxypropyl methylcellulose (HPMC) capsule filled with delayed-release pellets. The capsule is opaque white or white and is size 0. The delayed-release capsule contains pellets composed of sucrose spheres coated with an inner layer of P3A drug substance in excipients and a pH sensitive enteric outer coat in excipients. The pellets are designed to begin dissolving in the upper small intestine as the pH rises above 5.5, releasing the drug substance.

The list of components and the amounts in P3A delayed-release capsules (75 mg and 25 mg strength) and placebo capsules are provided in the table below. For the 75 mg and 25 mg strength P3A delayed-release capsules, pellets from the same manufacture batch were encapsulated to the desired capsule strength, so the percent of each component is identical. For the placebo capsules, the placebo pellets were encapsulated to match the level of EUDRAGIT® L 30 D-55 enteric coat excipient (20.8%) of the P3A delayed-release capsule, 75 mg drug product.

| Composition of P3A Delayed-Release Capsules, 75 mg and 25 mg, and Placebo Capsule | | | | | | |
|---|---|---|---|---|---|---|
| | 75 mg Capsule | | 25 mg Capsule | | Placebo Capsule | |
| Component | mg | % Total | mg | % Total | mg | % Total |
| Sucrose sphere | 110.8 | 23.3 | 36.9 | 23.3 | 139.8 | 29.5 |
| Hydroxypropylcellulose | 166.3 | 35.0 | 55.4 | 35.0 | 209.6 | 44.2 |
| EUDRAGIT ® L 30 D-55 | 98.9 | 20.8 | 33.0 | 20.8 | 98.7 | 20.8 |
| P3A | 75.0 | 15.8 | 25.0 | 15.8 | — | — |
| Buffer salts | 7.5 | 1.6 | 2.5 | 1.6 | 9.4 | 2.0 |
| Glyceryl monostearate | 4.9 | 1.0 | 1.6 | 1.0 | 4.9 | 1.0 |

Composition of P3A Delayed-Release Capsules, 75 mg and 25 mg, and Placebo Capsule

| Component | 75 mg Capsule | | 25 mg Capsule | | Placebo Capsule | |
|---|---|---|---|---|---|---|
| | mg | % Total | mg | % Total | mg | % Total |
| Polysorbate-80 | 2.0 | 0.4 | 0.7 | 0.4 | 2.0 | 0.4 |
| Triethyl citrate | 9.9 | 2.1 | 3.3 | 2.1 | 9.9 | 2.1 |
| Subtotal | 475.3 | 100.0 | 158.4 | 100.0 | 474.3 | 100.0 |
| Hard gelatin capsule #0 or Hydroxypropyl methylcellulose (HPMC) capsule | 96.0 | | 96.0 | | 96.0 | |
| Total | 571.3 | | 254.4 | | 570.3 | |

Figure 1B:
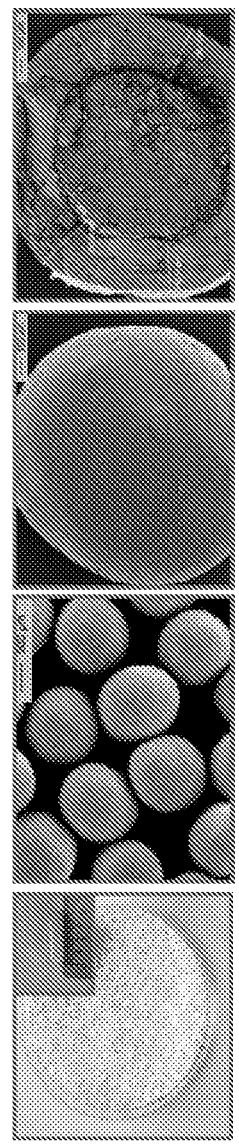
FIG. 1B shows photographs of P3A enteric-coated pellets produced according to an embodiment of the invention.

Representative photographs of P3A delayed-release pellets and capsules are shown in FIG. 1B. The pellets were uniform spheres of 1.0 to 1.3 mm in diameter, with a smooth appearance. Size 0 capsules were filled with the pellets. Each capsule contained approximately 75 mg of P3A (15-16% P3A/pellet) with a weight of approximately 475 mg of active pellet drug product+96 mg empty capsule weight, for a total of approximately 571 mg.

Example 3: A Phase 1, Single Ascending Sequential Dose Safety, Tolerance, and PK Study in Health Adult Subjects A Phase 1, double blind, placebo controlled study was carried out to assess the safety, tolerability, and pharmacokinetics (PK) of SYN-004 in healthy adult subjects. Specifically, a single dose of oral SYN-004 capsule (75 mg, 150 mg, 300 mg, 600 mg, or 750 mg) was administered to subjects. Blood samples were collected for PK evaluation and determination of anti-SYN-004 antibodies. A total of 40 healthy adult subjects were enrolled in the study with 6 active and 2 placebo subjects per cohort.

Overall, no clinically significant safety events were observed. Out of the 40 subjects, 11 subjects (27.5%) had 12 treatment-emergent adverse events (TEAEs). There were no serious adverse events (SAEs), no discontinuations due to an adverse event (AE), and no deaths. Eight of 30 (26.7%) SYN-004 subjects reported 9 TEAEs (flatulence 5, headache 3, and somnolence 1) and 3 of 10 (30%) placebo (PBO) subjects reported 3 TEAEs (headache 2 and neck pain 1). All TEAEs were reported as Grade 1 in intensity (does not interfere with normal activities) and resolved without intervention. These data indicate that SYN-004 was safe and well-tolerated at a single dose of up to 750 mg. There were no identified safety or tolerability concerns attributable to SYN-004.

In addition, SYN-004 taken orally was not systemically bioavailable. In the highest dose group (750 mg), all 6 subjects had at least one SYN-004 plasma concentration above the lower limit of quantification (LLOQ) of 0.8 ng/ml (Cmax 1.4 ng/ml, Tmax 1-4 hours post dose), but none of the lower dose groups had consistent PK parameters. No anti-SYN-004 antibodies were detected. These results indicate that SYN-004 was not systemically bioavailable. Without wishing to be bound by theory, it is believed that SYN-004 goes directly to the gut where antibiotics (e.g., administered by IV) are excreted and has no effect on the antibiotic in the bloodstream. In addition, SYN-004 was not immunogenic at the oral doses tested.

Example 4: A Phase 1, Multiple Ascending Sequential Dose Safety, Tolerance, and PK Study in Health Adult Subjects A Phase 1, double blind, randomized, placebo controlled study was carried out to assess the safety, tolerability, and PK of SYN-004 in healthy adult subjects. Specifically, multiple doses of oral SYN-004 capsules (75 mg, 150 mg, or 300 mg) were administered to the subjects at 4 doses per day for 7 days. Blood samples were collected for PK evaluation and determination of anti-SYN-004 antibodies. A total of 24 healthy adult subjects were enrolled in the study with 6 active and 2 placebo subjects per cohort.

Overall, no clinically significant safety events were observed. Of the 24 subjects randomized (18 received SYN-004; 6 received placebo), 6 subjects (25%) had a total of 7 TEAEs; all occurred in subjects receiving SYN-004.

The 7 TEAEs included 2 flatulence, 2 headache, 1 pollakiura, 1 pyuria, and 1 hematuria. All TEAEs were reported as Grade 1 in intensity (does not interfere with normal activities) and resolved without intervention. The TEAEs of pyuria and of hematuria were in different patients, were both observed on microscopy only, and all AEs resolved without intervention. These data indicate that SYN-004 was safe and well-tolerated at multiple doses of up to 300 mg q.i.d. for seven days.

Consistent with results from the single dose study, SYN-004 was not systemically bioavailable even with a dosing of four times a day for 7 consecutive days. Any measurable peak plasma concentrations tended to occur in the 2-4 hour post-dose and the peak concentrations were at or near the assay LLOQ. Multiple dosing did not result in any prolongation of exposure to SYN-004 levels above the assay LLOQ. No anti-SYN-004 antibodies were detected indicating the SYN-004 was not immunogenic at the oral doses tested.

Example 5: A Phase 1 b/2a, Randomized, Multi-Center, Open-Label, Fixed-Sequence Study to Evaluate the Effect of Oral SYN-004 on the Pharmacokinetics of Intravenous Ceftriaxone in Healthy Adult Subjects with a Functioning Ileostomy This example evaluated the effects of two strengths of oral SYN-004 (75 mg or 150 mg) administered twice in six hours on the plasma pharmacokinetics (PK) and chyme concentrations of a single dose of ceftriaxone administered as an intravenous (IV) infusion (1 g infused over 30 minutes).

Further, this example evaluated if SYN-004 was present in chyme, if there was absorption of SYN-004 into plasma, and the safety and tolerability of SYN-004 (75 mg or 150 mg) in combination with IV ceftriaxone.

This was a Phase 1, randomized, multi-center, open-label study. Ten otherwise healthy subjects with functioning ileostomies who were between the ages of 18 and 80 years, inclusive, were enrolled. As an overview, in the first treatment period (Period 1) all subjects received an IV infusion of 1 gram (g) ceftriaxone. In the second treatment period (Period 2) all subjects received an IV infusion of 1 g ceftriaxone and 2 doses of either 75 mg or 150 mg of SYN-004, according to the randomization schedule, and administered 30 minutes before and 5.5 hours after the ceftriaxone infusion. Subjects were screened for study participation within 45 days prior to Check-in (Day −1), and the entire duration of the study may be up to 64 days (from Screening to the end-of-study visit).

Subjects who satisfied the Screening criteria were admitted to the clinical research unit (CRU) on Day −1 of Period 1 and undergo confirmatory eligibility assessments. On Day 1 of Period 1, eligible subjects were randomly assigned to 1 of 2 treatment groups (AB or AC) in a 1:1 ratio. In each treatment period (Period 1 and Period 2), subjects checked-in the day prior to dosing, underwent an overnight fast of at least 8 hours, and remained confined to the CRU until completion of the Day 1 study procedures (approximately 8.5 hours after the start of the infusion). The confinement period was a total of 4 days (2 sequential days at each Period 1 and Period 2), and the entire duration of the study was up to 64 days (from Screening to the EOS visit). Period 1 and Period 2 were separated by a washout period of 3 to 7 days when subjects remained at home.

The active dosage form of SYN-004 being administered was a hard gelatin, size 0, opaque white capsule containing delayed-release mini-pellets. Subjects randomized to Treatment AB received two oral doses of SYN-004 75 mg (1×75 mg capsule) twice in one day on Day 1 of Period 2. Subjects randomized to Treatment AC received two oral doses of SYN-004 150 mg (2×75 mg capsules) twice in one day on Day 1 of Period 2.

Specifically, in Period 1, all subjects received an IV infusion of 1 g ceftriaxone administered over 30 minutes on Day 1. In Period 2, subjects again received an IV infusion of 1 g ceftriaxone administered over 30 minutes on Day 1, as well as two oral doses of SYN-004 (75 mg or 150 mg) 30 minutes before and 5.5 hours after the IV infusion of 1 g ceftriaxone. All subjects received an infusion of ceftriaxone 1 g over 30 minutes in Period 1 and a second identical, time matched infusion in Period 2. The exact time of day of dosing for consecutive subjects may be staggered (±1 hour) to accommodate sample collection logistics; however, the time of day of ceftriaxone administration on Day 1 in Periods 1 and 2 were consistent for each subject.

With respect to meals and fluid intake, on Day 1 in each period, subjects received a small non-fatty meal approximately 1 hour (7:00 AM) prior to administration of ceftriaxone and again 5 hours after the start of infusion (1:00 PM). Subjects received full meals at approximately 2 and 7.5 hours after the start of the infusion (10:00 AM and 3:30 PM), respectively. In order to generate sufficient chyme output, subjects drank 8 ounces of water or apple juice at the start of the infusion and at 0.5, 1, and 1.5 hours after the start of the infusion (i.e., every half hour between 8:00 AM and 9:30 AM); thereafter, subjects were encouraged to drink 8 ounces of water or apple juice hourly between 2 and 7 hours after the start of the infusion (10:00 AM to 3:00 PM).

Figure 2:
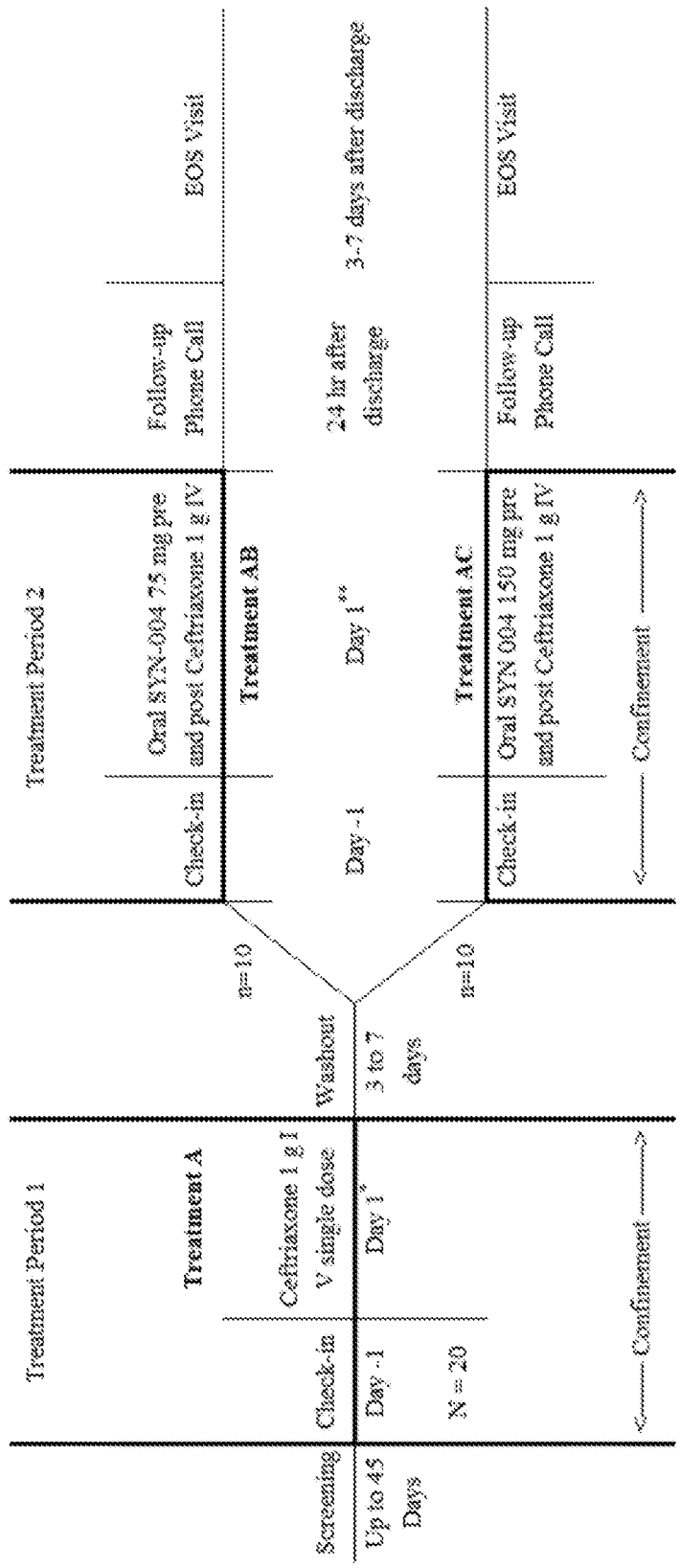
FIG. 2 shows a schematic of the study design employed in Example 5.

On Day 1, Period 1, serial blood and chyme samples were collected from approximately 30 minutes pre-dose through approximately 7 hours for serial blood and 8.5 for chyme after the start of infusion for determination of ceftriaxone concentration. On Day 1 of Period 2, serial blood and chyme samples were collected from approximately 30 minutes pre-dose through approximately 7 hours for serial blood and 8.5 hours for chyme after the start of the infusion for the determination of ceftriaxone and SYN-004 concentrations. Subjects were discharged from the CRU after completion of all study procedures on Day 1 of Period 2. A follow-up phone call was made approximately 24 hours after discharge, and subjects returned to the clinic for EOS assessments 3 to 7 days after discharge. See FIG. 2 for a schematic representation of the study.

Pharmacokinetics: Serial blood (5 mL each) and chyme samples (2 mL minimum) were collected on Day 1 of Period 1 and Period 2. The following PK parameters of SYN-004 and ceftriaxone were determined from the plasma and chyme concentration-time data for all evaluable subjects using non-compartmental methods: maximum observed plasma concentration (Cmax), area under the concentration-time curve from time 0 to the last quantifiable concentration (AUCt), and time to reach Cmax (Tmax) as applicable. In addition, area under the concentration-time curve from time 0 to infinity (AUC∞) was calculated where determinable.

Safety: Safety assessments included clinical laboratories, vital signs, ECGs, PEs, and monitoring for AEs. AEs regardless of relationship to study drug or to ceftriaxone were monitored from the time of IC until the EOS visit. Serious adverse events (SAEs) that were considered by the principal investigator (PI) to be "related" to the investigational product were reported to the contract research organization (CRO) at any time during or after the study.

Figure 4:
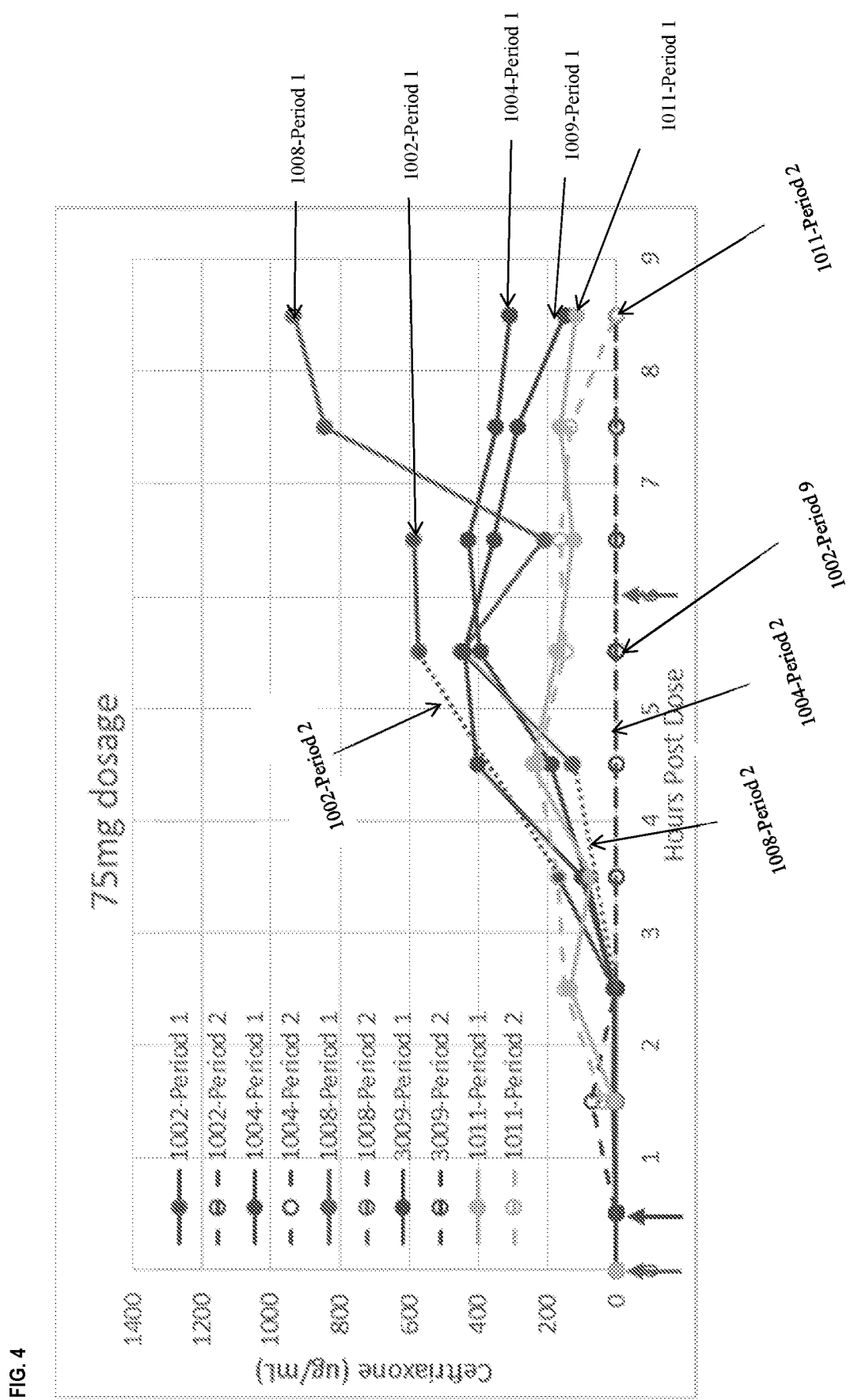
FIG. 4 depicts the ceftriaxone levels of subjects in the 75 mg dosage group as described in Example 5.

Results:

FIG. 4 and the table below summarize the chyme ceftriaxone concentrations during Periods 1 and 2 in five subjects dosed at 75 mg of SYN-004. In 4 of 5 subjects, ceftriaxone was detected in Period 1 and negligible in Period 2. For the fifth subject 1011, SYN-004 was not detected in their chyme until the 8.5 hour mark at which point the ceftriaxone concentration dropped below the limit of quantitation (see FIG. 9)

| | Ceftriaxone | | | | | | | | | |
|---|---|---|---|---|---|---|---|---|---|---|
| | Period 1 | | | | | Period 2 µg/mL | | | | |
| Time (75 mg) | 1002 | 1004 | 1008 | 3009 | 1011 | 1002 | 1004 | 1008 | 3009 | 1011 |
| 0 | 0 | 0 | 0 | 0 | 0 | 0 | 0 | 0 | 0 | 0 |
| 0.5 | | 0 | | 0 | | | 0 | 0 | 0 | |
| 1.5 | | 0 | 3 | 9 | 4 | | 0 | 0 | 74 | 42 |
| 2.5 | 6 | 7 | 0 | 4 | 135 | 1 | 0 | 0 | | 151 |
| 3.5 | 170 | 91 | | 102 | 75 | 0 | 0 | 0 | | 170 |

-continued

| | Ceftriaxone | | | | | | | | | |
|---|---|---|---|---|---|---|---|---|---|---|
| | Period 1 | | | | | Period 2 µg/mL | | | | |
| Time (75 mg) | 1002 | 1004 | 1008 | 3009 | 1011 | 1002 | 1004 | 1008 | 3009 | 1011 |
| 4.5 | | 190 | 128 | 403 | 242 | | 0 | | 0 | 231 |
| 5.5 | 572 | 395 | 449 | 443 | 172 | 3 | 0 | 1 | 0 | 151 |
| 6.5 | 587 | 431 | 210 | 356 | 127 | 0 | 0 | | 0 | 164 |
| 7.5 | | 349 | 846 | 287 | 165 | | 0 | 0 | 0 | 136 |
| 8.5 | | 310 | 934 | 151 | 118 | 0 | 0 | 0 | 0 | 0 |

Figure 5:
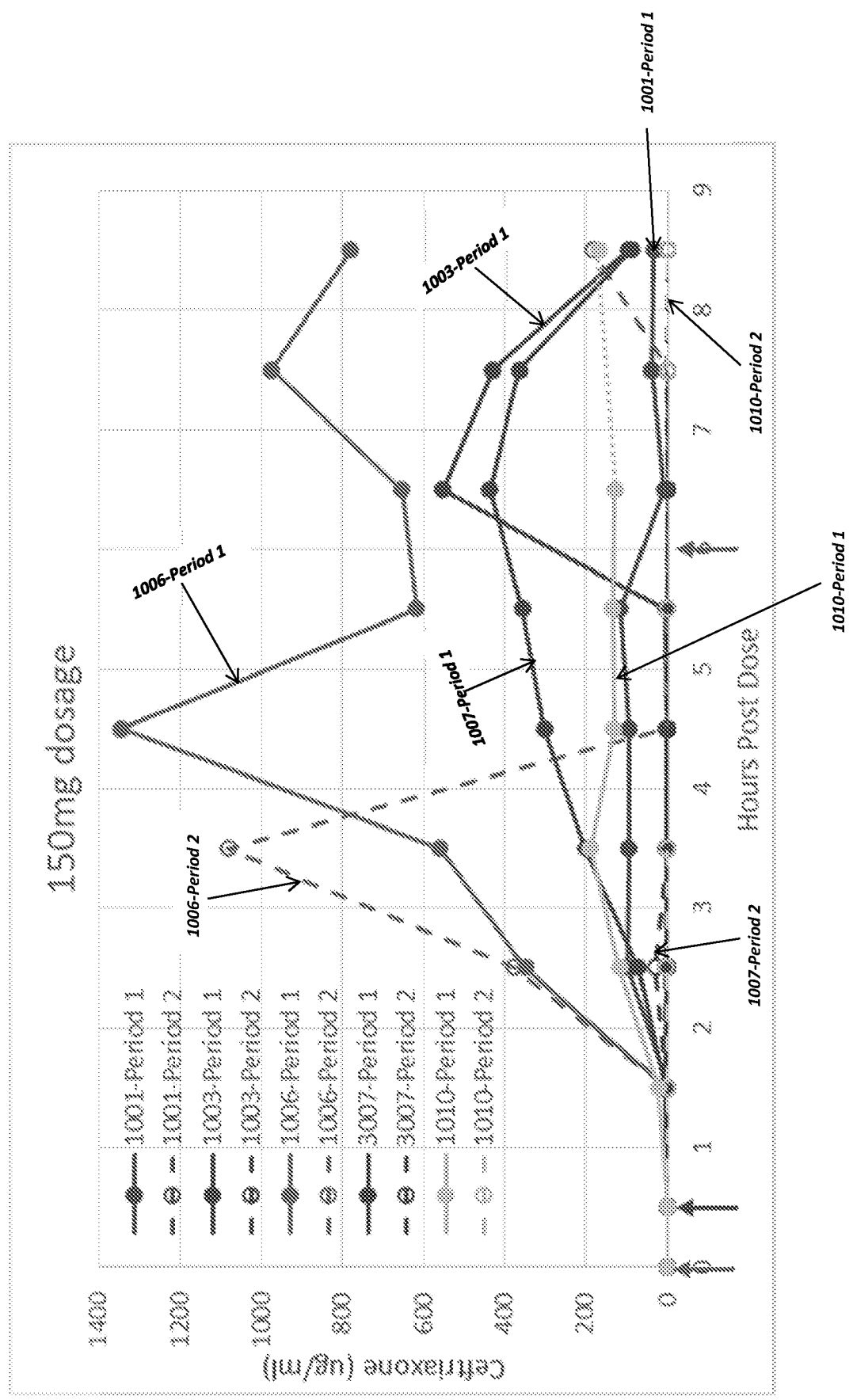
FIG. 5 depicts the ceftriaxone levels of subjects in the 150 mg dosage group as described in Example 5.

FIG. 5 and the table below summarize the ceftriaxone levels during Periods 1 and 2 in five subjects dosed at 150 mg of SYN-004. In 4 of 5 subjects, ceftriaxone was detected in the chyme during period 1 and was negligible period 2. In subject 1006 there was a fairly large peak of ceftriaxone detected early in period 2, but this was reduced below the level of detection when SYN-004 was detected in the chyme (see FIG. 8).

| | Ceftriaxone | | | | | | | | | |
|---|---|---|---|---|---|---|---|---|---|---|
| | Period 1 | | | | | Period 2 µg/mL | | | | |
| Time (150 mg) | 1001 | 1003 | 1006 | 3007 | 1010 | 1001 | 1003 | 1006 | 3007 | 1010 |
| 0 | 0 | 0 | 0 | 0 | 0 | 0 | 0 | 0 | 0 | 0 |
| 0.5 | 0 | 0 | 0 | 0 | 0 | 0 | 0 | 0 | 0 | |
| 1.5 | 0 | 5 | 2 | 8 | 24 | 0 | 4 | 6 | 3 | 0 |
| 2.5 | 97 | 1 | 348 | 71 | 118 | 0 | 5 | 376 | 31 | 3 |
| 3.5 | 94 | 1 | 560 | 201 | 188 | 0 | 3 | 1081 | 0 | 0 |
| 4.5 | 93 | 3 | 1345 | 302 | 129 | 0 | 0 | 1 | 0 | |
| 5.5 | 116 | 4 | 618 | 356 | 134 | 0 | 0 | 1 | 0 | 0 |
| 6.5 | 9 | 552 | 653 | 437 | 128 | 0 | 0 | 0 | 0 | |
| 7.5 | 39 | 430 | 975 | 364 | | 0 | 1 | 0 | 0 | 0 |
| 8.5 | 34 | 96 | 781 | 89 | 166 | 0 | 0 | 182 | 0 | 0 |

Peak(s) are indicated in bold.

Figure 6:
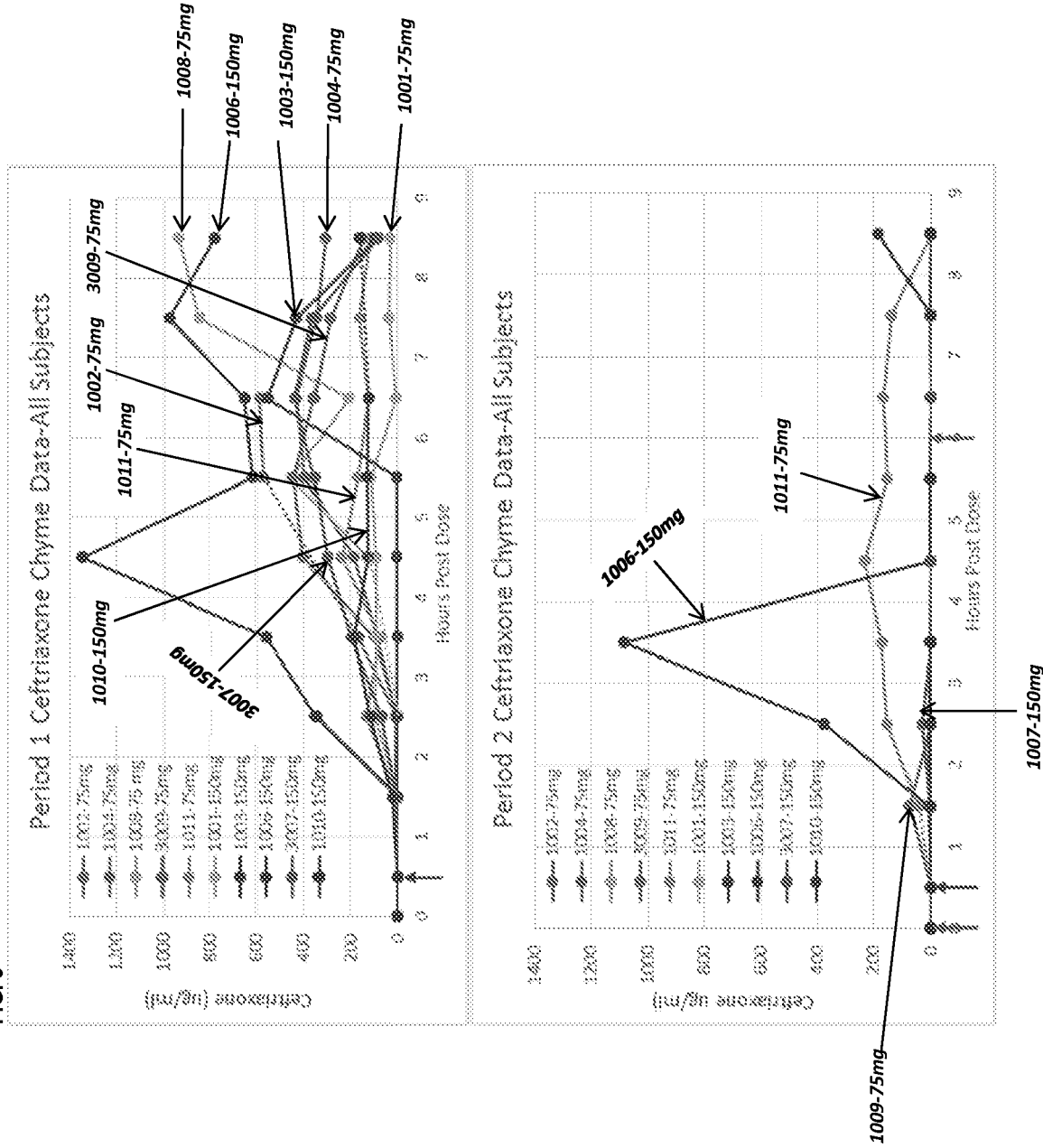
FIG. 6 depicts the ceftriaxone levels of all subjects during Period 1 as described in Example 5.

FIG. 6 depicts the ceftriaxone data of all subjects during Period 1. In general, all subjects had measurable ceftriaxone in their chyme in period 1 with peaks ranging from ~115 ug/ml to almost 1400 ug/ml. These concentrations are substantially above the minimal inhibitory concentration (MIC) for ceftriaxone for most bacteria. Ceftriaxone appeared in the chyme between 1.5 and 2.5 hours post dose for most subjects with a second peak of ceftriaxone that appears at around 6-8 hours post dose.

Figure 7A:
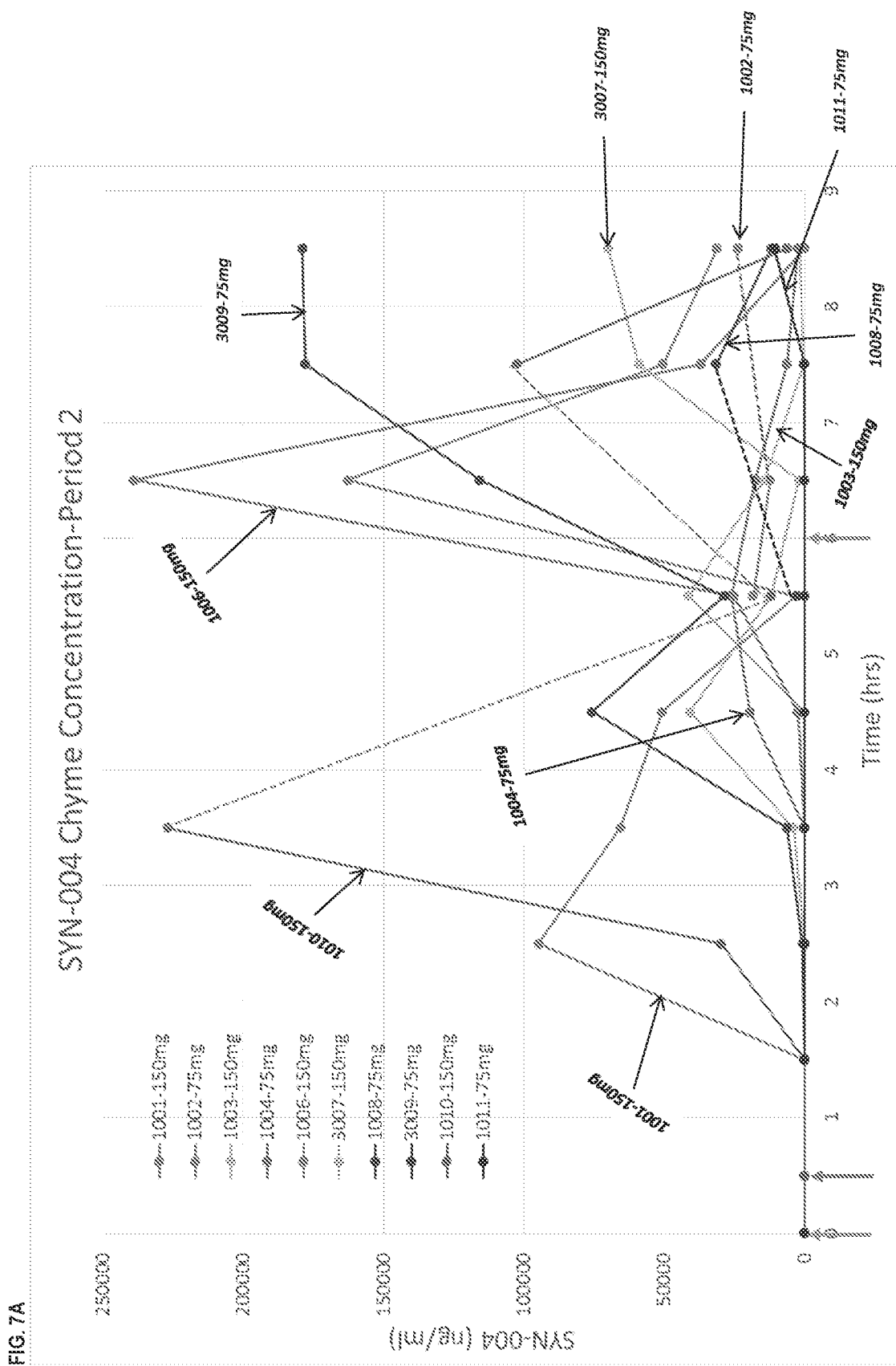
FIG. 7A depicts the SYN-004 levels in the chyme of all subjects during Period 2 as described in Example 5.
Figure 7B:
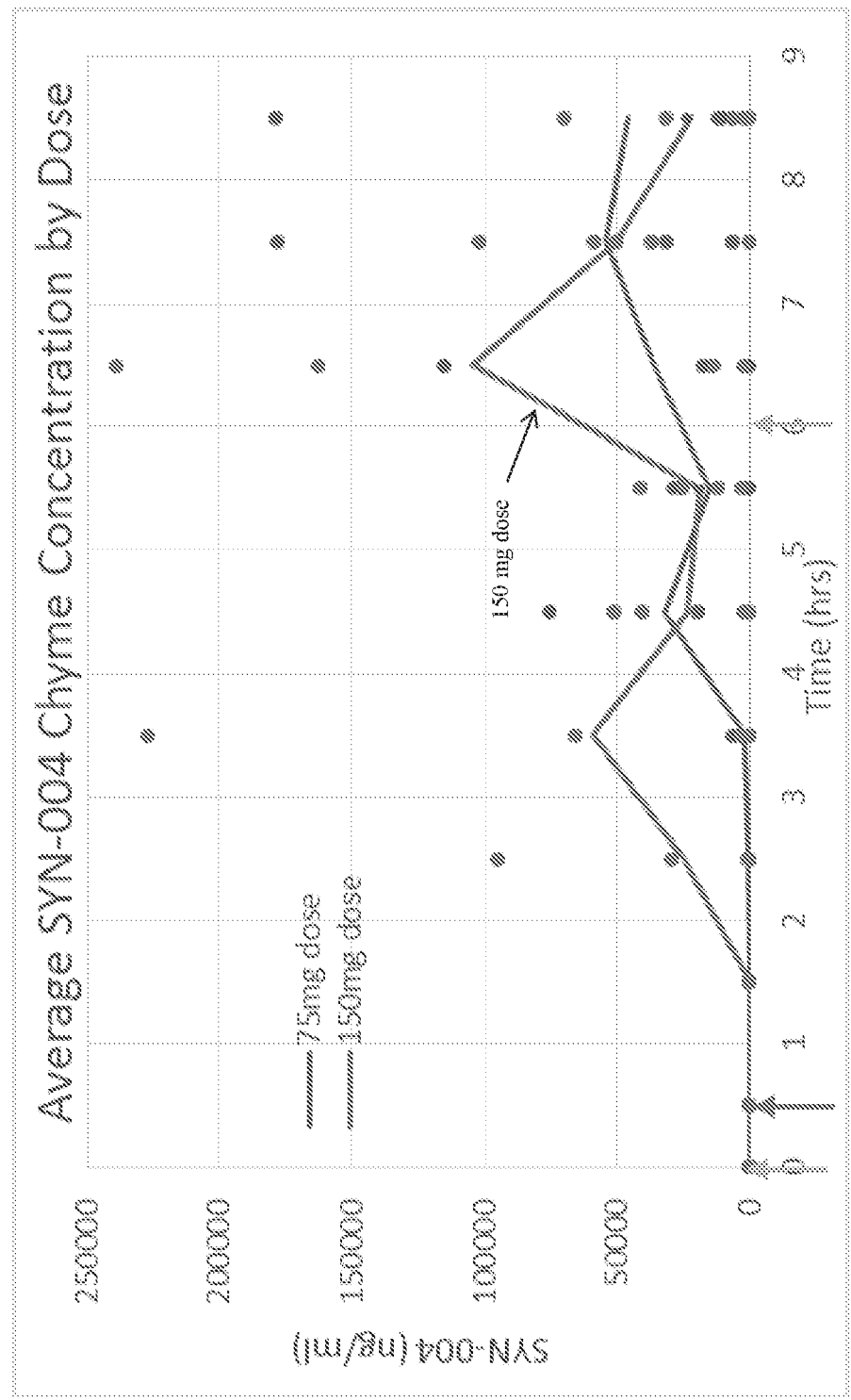
FIG. 7B shows the average SYN-004 levels in the chyme of all subjects. Solid line is the mean while the dots are the individual data comparing dose groups.

FIGS. 7A and 7B and the table below provide the SYN-004 levels in the chyme of all subjects during Period 2. For most subjects, measurable SYN-004 began to be detectable in the chyme 5.5 hours post first dose. Without wishing to be bound by theory, it is believed that the apparent delay in the appearance of detectable SYN-004 in the chyme as compared with detectable ceftriaxone could be a result of ceftriaxone being much smaller than SYN-004 and thus having a faster transit time in the intestine as compared with SYN-004, reaching the ileostomy bag sooner.

| Time | 75 mg dose | | | | | 150 mg dose | | | | |
|---|---|---|---|---|---|---|---|---|---|---|
| (hrs) | 1002 | 1004 | 1008 | 3009 | 1011 | 1001 | 1003 | 1006 | 3007 | 1010 |
| 0 | 0 | 0 | 0 | 0 | 0 | 0 | 0 | 0 | 0 | 0 |
| 0.5 | | 0 | 0 | 0 | 0 | | 0 | 0 | 0 | 0 |
| 1.5 | | | 0 | 0 | 0 | 27 | 0 | 0 | 0 | 0 |
| 2.5 | | 0 | 0 | 883 | 0 | 94818 | 0 | 0 | 29 | 29,760 |
| 3.5 | | 131 | | 6,359 | 0 | 65710 | 0 | 0 | 3,964 | 227,183 |
| 4.5 | | 19,662 | | 75,739 | 0 | 50814 | 164 | 2,491 | 41,008 | |
| 5.5 | 18,331 | 26,285 | 2,904 | 28,788 | 0 | 3151 | 41,604 | 25,283 | 11,939 | 12,133 |
| 6.5 | 12,322 | 17,590 | | 115,729 | 0 | 162827 | 14,265 | 238,919 | 2,096 | |
| 7.5 | | 6,397 | 31,688 | 178,015 | 0 | 50505 | 365 | 37,206 | 59,129 | 102,483 |
| 8.5 | 23,790 | 2,477 | 12,003 | 179,089 | 10,738 | 31307 | 1,884 | 12 | 70,067 | 6,453 |

Peak(s) are indicated in bold.

Figure 8:
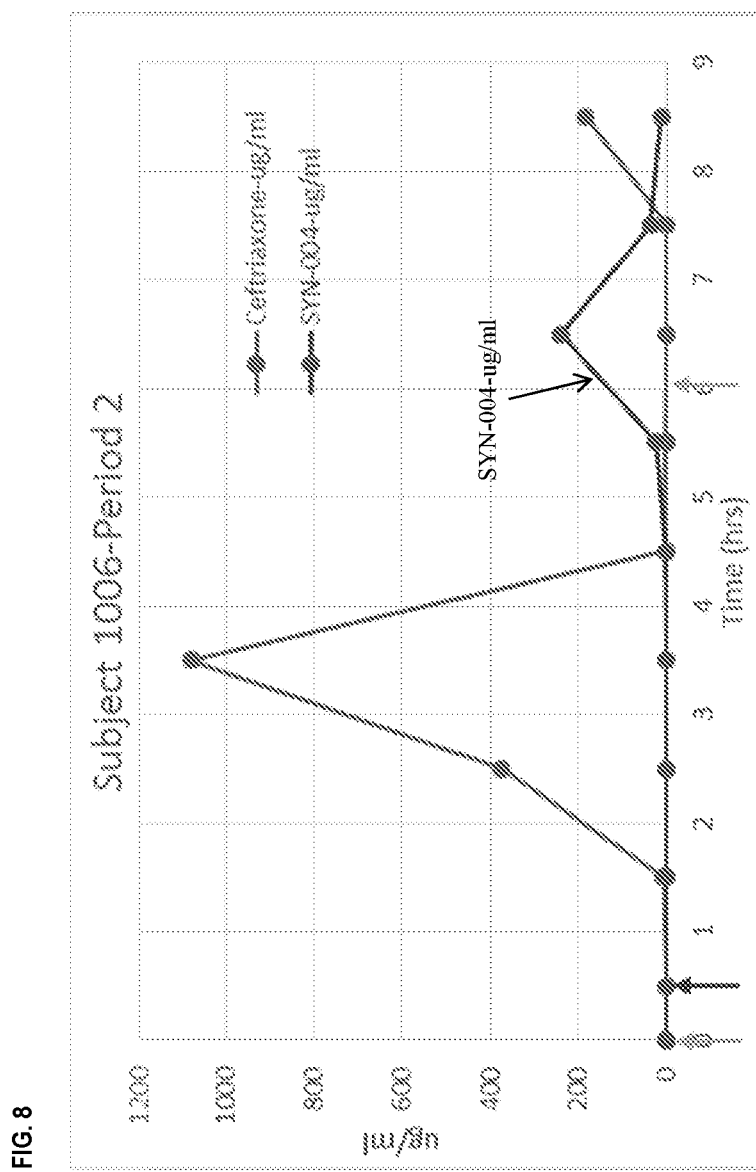
FIG. 8 provides an overlay of the ceftriaxone levels and SYN-004 levels in the chyme of subject 1006 during Period 2 as described in Example 5.
Figure 9:
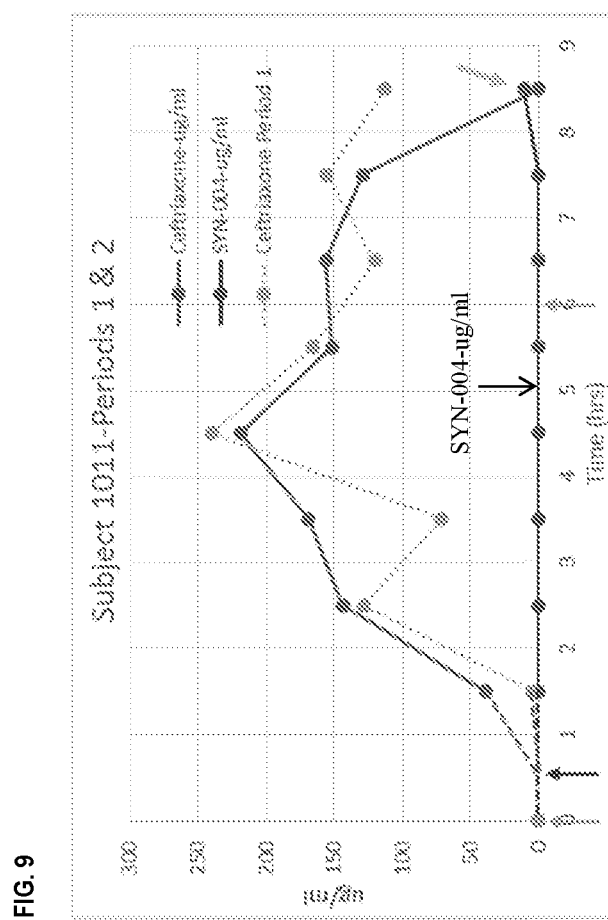
FIG. 9 shows Example 5 study subject 1011 (the fifth subject)'s chyme SYN-004 and ceftriaxone levels.

The ceftriaxone data was compared to the SYN-004 data for Period 2 for Subjects 1006 and 1011 (FIGS. 8 and 9 and table below). Specifically, when the ceftriaxone peak was present during Period 2 for subjects 1006 and 1011, there did not seem to be any SYN-004 detected in the chyme, and when the SYN-004 began to appear at ~4.5 hours and 8.5 hrs respectively, the ceftriaxone was gone from the chyme. As the SYN-004 disappeared around 8.5 hours for subject 1006 the ceftriaxone levels start to increase again. This data suggested that SYN-004 effectively degraded ceftriaxone in both subjects when both substances were present in the chyme. For subject 1011, the ceftriaxone concentration in period 1 is shown below for comparison.

| 1008 Time (hrs) | Ceft ug/ml | SYN-004 ug/ml | 1011 Time (hrs) | Ceft Period 1 | Ceft ug/ml | SYN-004 ug/ml |
|---|---|---|---|---|---|---|
| 0 | 0 | 10 | 0 | 0.00 | 0 | 0 |
| .5 | 0 | 10 | 0.5 |  | 0 | 0 |
| 1.5 | 6.49 | 10 | 1.5 | 4.23 | 39 | 0 |
| 2.5 | 375.79 | 10 | 2.5 | 128.71 | 144 | 0 |
| 3.5 | 1081.12 | 10 | 3.5 | 71.47 | 169 | 0 |
| 4.5 | 1.34 | 2.4 | 4.5 | 240.26 | 219 | 0 |
| 5.5 | 1.33 | ° | 5.5 | 165.24 | 152 | 0 |
| 6.5 | 0 | 239 | 6.5 | 120.51 | 156 | 0 |
| 7.5 | 0 | ° | 7.5 | 155.47 | 129 | 0 |
| 8.5 | 182.25 | 12 | 8.5 | 113.10 | 0 | 11 |

FIG. 10 and the table below provide the ceftriaxone plasma concentrations in periods 1 and 2. There was no significant difference between the plasma concentration of ceftriaxone in Period 1 and 2 supporting the finding that SYN-004 was not systemically bioavailable.

Residual ceftriaxone in the intestinal chyme was degraded when SYN-004 was present and ceftriaxone concentrations were generally lower for the 150 mg SYN-004 dose than for the 75 mg SYN-004 dose.

Plasma concentrations of ceftriaxone were similar after a 1 g IV infusion with and without concomitant oral SYN-004 administration.

Concentrations of SYN-004 were not measurable in plasma when doses of 75 or 150 mg were administered orally approximately 30 min before and 5.5 h after starting a ceftriaxone IV infusion.

Concentrations of SYN-004 in chyme, though variable, were generally higher for the 150 mg dose regimen than for the 75 mg dose regimen.

Altogether, these data demonstrated that following oral administration, a delayed release capsule SYN-004 acted locally in the intestinal tract to degrade residual ceftriaxone. Furthermore, SYN-004 did not appear to impact the plasma PK profile of ceftriaxone.

Example 6: A Phase 1b/2a, Multi-Center, Open-Label, 2-Period, Fixed-Sequence Study Evaluating the Effect of Esomeprazole on SYN-004 Degradation of Ceftriaxone in Healthy Adult Subjects with a Functioning Ileostomy This example evaluated the effect of steady state esomeprazole on the activity of SYN-004 in chyme, as determined by chyme concentrations of ceftriaxone. Further, this example evaluated if SYN-004 was present in chyme and/or absorbed into plasma, determined the effects, if any, on the concentration of ceftriaxone in plasma, and evaluated the

| Period 1 Time | 75 mg 1001 | 150 mg 1002 | 1003 | 1004 | 1006 | 3007 | 1008 | 3009 | 1010 | 1011 |
|---|---|---|---|---|---|---|---|---|---|---|
| 0 | 0 | 0 | 0 | 0 | 0 | 0 | 0 | 0 | 0 | 0 |
| 0.25 | 92100 | 77300 | 154000 | 71700 | 95500 | 73500 | 74300 | 81800 | 90800 | 71200 |
| 0.5 | 154000 | 139000 | 235000 | 132000 | 148000 | 184000 | 131000 | 156000 | 172000 | 131000 |
| 0.75 | 131000 | 122000 | 170000 | 118000 | 146000 | 146000 | 103000 | 114000 | 124000 | 108000 |
| 1 | 121000 | 107000 | 164000 | 103000 | 117000 | 127000 | 93600 | 104000 | 127000 | 93300 |
| 2 | 101000 | 79200 | 132000 | 80000 | 96800 | 112000 | 67100 | 75600 | 10500 | 74000 |
| 3 | 79900 | 60300 | 118000 | 70900 | 78900 | 100000 | 61300 | 67100 | 90600 | 64500 |
| 4 | 76700 | 55300 | 109000 | 64300 | 71000 | 84600 | 47400 | 60400 | 83800 | 56900 |
| 5 | 73000 | 54400 | 104000 | 55200 | 62200 | 78800 | 48500 | 58100 | 77900 | 50300 |
| 6 | 65800 | 49900 | 86500 | 47900 | 55500 | 72800 | 45500 | 53500 | 69700 | 43800 |
| 7 | 56000 | 43500 | 84700 | 42500 | 53700 | 66600 | 42700 | 46000 | 55300 | 42700 |
| Period 2 Time | 1001 | 1002 | 1003 | 1004 | 1006 | 3007 | 1008 | 3009 | 1010 | 1011 |
| 0 | 0 | 0 | 0 | 0 | 0 | 0 | 0 | 0 | 0 | 0 |
| 0.25 | 80200 | 70200 | 168000 | 77500 | 83900 | 68400 | 78400 | 91600 | 96400 | 77000 |
| 0.5 | 139000 | 139000 | 219000 | 140000 | 176000 | 140000 | 135000 | 167000 | 172000 | 138000 |
| 0.75 | 124000 | 120000 | 172000 | 113000 | 144000 | 135000 | 100000 | 121000 | 137000 | 119000 |
| 1 | 110000 | 104000 | 161000 | 107000 | 132000 | 119000 | 91800 | 107000 | 107000 | 104000 |
| 2 | 87800 | 84300 | 127000 | 77400 | 96400 | 99700 | 69900 | 88200 | 92300 | 77900 |
| 3 | 84200 | 72900 | 121000 | 69300 | 84200 | 87000 | 59600 | 78600 | 90900 | 65100 |
| 4 | 77200 | 57700 | 109000 | 60000 | 76400 | 81400 | 52300 | 70300 | 85000 | 56500 |
| 5 | 69400 | 51900 | 102000 | 55200 | 65700 | 75900 | 50500 | 59000 | 81900 | 50000 |
| 6 | 58900 | 47300 | 91200 | 47600 | 59600 | 71900 | 46400 | 53600 | 73800 | 43000 |
| 7 | 58900 | 46100 | 90700 | 41400 | 51600 | 60700 | 39600 | 46100 | 69600 | 40900 |

The following conclusions, inter alia, were drawn from this study:

Beginning approximately 4 hours after starting the ceftriaxone infusion, and in some cases earlier, mean ceftriaxone concentrations in chyme were decreased by concomitant SYN-004 administration.

safety and tolerability of administration of SYN-004 with ceftriaxone in the presence and absence of esomeprazole.

By way of overview, this was a Phase 1b/2a, multi-center, open-label, 2-period, fixed-sequence study. About twenty otherwise healthy subjects with functioning ileostomies who were between the ages of 18 and 70 years, inclusive, were expected to be enrolled. There were 2 in-house treatment periods: in Treatment Period 1, subjects received 2 oral doses of 150 mg SYN-004 (two 75 mg capsules) and 1 g ceftriaxone, and in Treatment Period 2, subjects received 2 oral doses of 150 mg SYN-004 (two 75 mg capsules) and 1 g ceftriaxone in the presence of steady-state esomeprazole. Treatment Periods 1 and 2 were separated by a 5- to 7-day run-in phase, during which subjects self-administered 40 mg of esomeprazole once daily (QD) in the morning, at home. See FIG. 3 for a schematic representation of the study.

Subjects were screened for study participation within 45 days prior to Check-in (Day −1) of Treatment Period 1, and the entire duration of the study was up to 63 days (from Screening to the End-of-Study [EOS] visit). Subjects who satisfied the Screening criteria were admitted to the clinical research unit (CRU) on Day −1 of Treatment Period 1 and underwent confirmatory eligibility assessments; only qualified subjects were allocated to treatment. In each treatment period (Treatment Period 1 and Treatment Period 2), subjects checked into the CRU the day prior to dosing, underwent an overnight fast of at least 8 hours, and remained confined to the CRU until completion of the Day 1 study procedures (approximately 8.5 hours after the start of the ceftriaxone infusion). Thus, in each Treatment Period, subjects were confined to the CRU for 2 consecutive days (Day −1 to Day 1) for a total of 4 confinement days.

The active dosage form of SYN-004 was a hard gelatin, size 0, opaque white capsule containing delayed-release pellets.

Specifically, in the first treatment period (Treatment Period 1), subjects received 2 oral doses of 150 mg (two 75 mg capsules) of SYN-004 (one dose approximately 30 minutes before the start of the ceftriaxone infusion and the second dose 5.5 hours after the start of the ceftriaxone infusion [at approximately 7:30 AM and 1:30 PM]). The subjects also received an intravenous (IV) dose of 1 g of ceftriaxone infused over 30 minutes beginning at approximately 8 AM. As such, the second 150 mg dose was administered about 6 hours after the first 150 mg dose.

Treatment Periods 1 and 2 were separated by a run-in phase, during which subjects self-administered esomeprazole 40 mg QD in the morning for 5 to 7 consecutive days at home before returning to the CRU for Treatment Period 2.

In Treatment Period 2, subjects continued their esomeprazole dosing on Day −1. On Day 1, subjects received a single oral 40 mg dose of esomeprazole at approximately 6:30 AM, which was 1.5 hours prior to the start of the ceftriaxone infusion and then SYN-004 and ceftriaxone were administered in the same manner as previously described for Treatment Period 1.

Accordingly, all subjects received an infusion of ceftriaxone (1 g) over 30 minutes in Treatment Period 1 and a second identical, time-matched infusion of ceftriaxone in Treatment Period 2. In addition, subjects self-administered oral doses of 40 mg of esomeprazole QD in the morning at home for 5 to 7 days during the run-in period prior to Treatment Period 2 including Day −1 of Treatment Period 2 and again in-house on Day 1 of Treatment Period 2.

The exact time of day of dosing for consecutive subjects may be staggered (±1 hour) to accommodate sample collection logistics; however, the time of day of ceftriaxone administration, relative timing of SYN-004 and meals, on Day 1 in Treatment Periods 1 and 2 were consistent for each subject.

With respect to meals and fluid intake, on Day 1 of each Treatment Period, subjects received small non-fatty meals approximately 1 hour prior to and 5 hours after the start of infusion (approximately 7 AM and 1 PM, respectively), and full meals at approximately 2 and 7.5 hours after the start of the infusion (approximately 10 AM and 3:30 PM, respectively). In order to generate sufficient chyme output, subjects were required to drink 8 ounces of water or apple juice at the start of the infusion and at 0.5, 1, and 1.5 hours after the start of the infusion (i.e., every half hour between 8 AM and 9:30 AM); thereafter, subjects were encouraged to drink 8 ounces of water or apple juice hourly between 2 and 7 hours after the start of the infusion (10 AM to 3 PM).

On Day 1 of each Treatment Period, serial blood samples were collected from pre-dose through 7 hours after the start of the infusion, and serial chyme samples were collected from pre-dose through 8.5 hours after the start of the infusion, for the determination of ceftriaxone and SYN-004 concentrations in plasma and chyme.

Subjects were discharged from the CRU after completion of all study procedures in Treatment Period 2. A follow-up phone call was made approximately 24 hours after discharge, and subjects returned to the clinic for EOS assessments 3 to 7 days after discharge.

Pharmacokinetics: Serial blood (no more than 12 mL at each sampling time) and chyme samples (2 mL minimum) were collected on Day 1 of Treatment Period 1 and Treatment Period 2 as outlined in the Schedule of Assessments and Detailed Schedule of Assessments for Day 1 of each Treatment Period. The following PK parameters of SYN-004 and ceftriaxone were determined from the plasma and chyme concentration-time data for all evaluable subjects using non-compartmental methods: maximum observed plasma concentration (Cmax), area under the concentration-time curve from time 0 to the last quantifiable concentration (AUCt), and time to reach Cmax (Tmax) as applicable. In addition, area under the concentration-time curve from time 0 to infinity (AUC∞) was calculated where determinable.

Safety: Safety assessments included evaluations of clinical laboratories, vital signs, ECGs, PEs, and monitoring for AEs. AEs regardless of relationship to study drug, ceftriaxone, or to esomeprazole, were monitored from the time of informed consent until the EOS visit. Serious adverse events (SAEs) that are considered by the principal investigator (PI) to be related to the study drug (SYN-004) were reported to the contract research organization (CRO) at any time during or after the study.

Results:

Topline results are available from the ten ileostomized participants who completed the Phase 2a open-label study in which SYN-004 was administered in the absence or presence of steady state esomeprazole. These results demonstrated that SYN-004 successfully degraded residual IV ceftriaxone in the chyme without affecting the intended level of ceftriaxone in the bloodstream in the absence or presence of esomeprazole. Evaluation of the chyme from the ileostomized participants indicated that SYN-004 (150 mg) degraded residual IV ceftriaxone present in the chyme in the absence or presence of esomeprazole, supporting the proposed (without wishing to be bound by theory) mechanism of action of SYN-004 and demonstrating that it could be administered in the presence of proton pump inhibitors. In addition SYN-004 appeared to be well tolerated by the participants in the study when administered in the presence of esomeprazole. When SYN-004 was administered in the presence of steady state esomeprazole, SYN-004 could be detected in the intestinal chyme earlier than when SYN-004 was administered without esomeprazole. This was consistent with esomeprazole raising the pH of the intestine leading to earlier release of the active enzyme from the pH-dependent formulation. Unexpectedly, this earlier release of SYN-004 into the intestinal chyme when coadministered with steady state esomeprazole seemed to enhance the ability of SYN-004 to degrade the excess ceftriaxone in the chyme as shown in the tables and figures. Overall, the topline data supported the hypothesis that SYN-004 could be administered in the presence of proton pump inhibitors and still have the capacity to degrade residual IV ceftriaxone in the GI tract, thereby preserving the balance of the gut microbiome for the prevention of CDI, AAD and emergence of antibiotic-resistant organisms, without affecting the antibiotic level in the bloodstream intended for treatment of a primary infection.

With respect to ceftriaxone, the results are shown in the table below and in FIG. 11. Specifically, in 10 subjects who were analyzed, there was a ceftriaxone peak during period 1 and no ceftriaxone during period 2 (six subjects are shown in FIG. 13).

Ceftriaxone Data in ug/ml

| Time | 1001-Period 1 | 1001-Period 2 | 1002-Period 1 | 1002-Period 2 |
|---|---|---|---|---|
| 0   | 0      | 0 | 0       | 0     |
| 0.5 | 0      | 0 | 0       | 0     |
| 1.5 | 0      | 0 | 6.88    | 13.19 |
| 2.5 | 150.11 | 0 | 727.09  | 7.09  |
| 3.5 | 0      | 0 | 1204.66 |       |
| 4.5 | 0      | 0 | 909.03  | 0     |
| 5.5 | 0      | 0 | 30.40   | 0     |
| 6.5 | 0      | 0 | 3.15    |       |
| 7.5 | 0      | 0 | 1.31    | 0     |
| 8.5 | 0      | 0 | 1.06    | 0     |

One of the objective of the study was to assess whether SYN-004 can still degrade ceftriaxone in the chyme (and does not degrade ceftriaxone in the plasma) when it is administered in the presence of esomeprazole (e.g., NEXIUM). Unexpectedly, it was discovered that the presence of esomeprazole (e.g., NEXIUM) actually seemed to enhance the degradation of ceftriaxone in the dosing regimen used during the study. As indicated in the table below and in FIGS. 12 and 13, when esomeprazole (e.g., NEXIUM) was used in period 2, SYN-004 was detected in the chyme earlier than it was in period 1 (see, for example, subject 1002). In these data, the highest level of SYN-004 was also observed out of any sample thus far (892,767 ng/ml for subject 1002 in period 2 at 2.5 hours).

| NEXIUM Period 1 | | SYN-004 Period 2 | ng/ml |
|---|---|---|---|
| 1001 | 1002 | 1001 | 1002 |
| 10     | 10    | 10      | 10      |
| 10     | 10    | 10      | 10      |
| 10     | 11.1  | 10      | 54      |
| 10     | 10    | 30,619  | 892,767 |
| 1996   | 10    | 103,597 |         |
| 33992  | 10    | 216,103 |         |
| 400789 | 31587 | 108,165 | 21,695  |
| 214763 | 47657 | 24,238  |         |
| 107450 | 93004 | 4836    | 396     |
| 107596 |       | 1069    | 378     |

Accordingly, the use of esomeprazole (e.g., NEXIUM) led to earlier appearance of SYN-004 in the chyme and this earlier appearance corresponded with no detectable ceftriaxone peak in period 2 for the subjects. In contrast, a ceftriaxone peak was seen in Period 1 for the subjects (FIG. 13).

The presence of esomeprazole (e.g., NEXIUM) seemed to cause an early release of SYN-004 (possibly, without wishing to be bound by theory, due to elevated pH due to esomerprazole) which in this dosing regimen is an advantage for ceftriaxone degradation. Without wishing to be bound by theory, it is believed that this may also be an advantage for the first dose of SYN-004 in a clinical setting where SYN-004 is expected to act as fast as possible to degrade intestinal antibiotics excreted from the first dose administered. As such, without wishing to be bound by theory, it is believed that the combined dosing of SYN-004 and a proton pump inhibitor such as esomeprazole (e.g., NEXIUM) provides advantages in clinical situations where early release of SYN-004 in the intestines is desired, e.g., around the administration of the first dose of IV antibiotic before steady state SYN-004 is achieved in the intestines. Alternatively an antacid may be utilized for early release of SYN-004 into the intestines for ceftriaxone or other β-lactam containing antibiotic degradation.

Example 7: A Phase 2b Study to Evaluate the Capacity of SYN-004 to Reduce the Risk of CDI, CDAD, and AAD in Hospitalized Patients Treated with Ceftriaxone for a Lower Respiratory Tract Infection This example will, among others, evaluate the effectiveness of SYN-004 to prevent *C. difficile* infection (CDI), *C. difficile* associated disease (CDAD) and antibiotic-associated diarrhea (AAD) in patients hospitalized for a lower respiratory tract infection and receiving intravenous (IV) ceftriaxone.

The Phase 2b, parallel-group, double-blind, placebo-controlled study of SYN-004 involves approximately 370 patients at up to 75 global clinical sites. Patients age 50 years and older, hospitalized for a lower respiratory tract infection, are randomized at a 1:1 ratio into two groups. Each group receives either SYN-004 or placebo during the standard of care regimen of ceftriaxone (with or without a macrolide). The primary objectives of the clinical trial are to evaluate the effectiveness of SYN-004 to prevent CDIs and CDAD. The secondary objective of this clinical trial is to evaluate the effectiveness of SYN-004 to prevent AAD.

It is expected that administration of SYN-004 protects the microbiome the treated subjects and effectively prevents CDI, CDAD, and AAD in these subjects.

Example 8: SYN-004 Activity in the Presence of Beta-Lactamase Inhibitors

Ceftriaxone (at 3 ug/ml or 1500 ug/ml) was mixed with human intestinal chyme alone, or with chyme plus SYN-004 (8 ug/ml) or with chyme plus the beta-lactamase inhibitor sulbactam, (20 mg/ml) or chyme plus both and then the samples were flash frozen. The flash frozen samples were thawed on ice and sulbactam was added to some samples, the protein was precipitated with acetonitrile and the samples were analyzed for ceftriaxone concentration by LC/MS-MS. The table below provides results from triplicate samples.

| | Percent of untreated control sample | |
|---|---|---|
| Sample | 3 ug/ml ceftriaxone | 1500 ug/ml ceftriaxone |
| Ceftriaxone alone | 100% [1] | 100% [1] |
| Ceftriaxone plus SYN-004 | 0% | 0% |
| Ceftriaxone plus SYN-004, sulbactam added at sample thaw | 0% | 2% |
| Ceftriaxone plus sulbactam and then add SYN-004 | ND [2] | 53.5% |

[1] Nominally set at 100%
[2] Not done

Even at 20 mg/ml Sulbactam, 8 ug/ml of SYN-004 could not be inhibited (that's a molar ratio of about 287,000:1, sulbactam to SYN-004). Altogether, these data suggested that Sulbactam did not substantially inhibit SYN-004 activity in intestinal chyme.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

What is claimed is:

1. A method of protecting a human patient's gastrointestinal microbiome, comprising administering an effective amount of a pharmaceutical composition comprising a beta-lactamase to a patient in need thereof, wherein:
   the patient is undergoing treatment or has recently undergone treatment with a beta-lactam antibiotic, wherein the beta-lactam antibiotic is a penicillin or a cephalosporin;
   the patient is undergoing treatment with a proton pump inhibitor, wherein the proton pump inhibitor is esomeprazole, omeprazole, lansoprazole, rabeprazole, pantoprazole, or dexlansoprazole; and
   the beta-lactamase comprises an amino acid sequence having at least 98% identity with SEQ ID NO: 1.

2. The method of claim 1, wherein the beta-lactam antibiotic and beta-lactamase are administered simultaneously.

3. The method of claim 1, wherein the beta-lactam antibiotic and beta-lactamase are administered sequentially.

4. The method of claim 1, wherein the beta-lactamase is administered orally.

5. The method of claim 1, wherein the beta-lactam antibiotic is administered parenterally, optionally selected from intravenously and/or by infusion.

6. The method of claim 1, wherein the protection of the patient's microbiome comprises treatment or prevention of a microbiome-mediated disorder selected from an antibiotic-induced adverse effect, C. difficile infection, and a C. difficile-associated disease.

7. The method of claim 6, wherein the antibiotic-induced adverse effect and/or CDI or *C. difficile*-associated disease is one or more of: antibiotic-associated diarrhea, *C. difficile* diarrhea (CDD), *C. difficile* intestinal inflammatory disease, colitis, pseudomembranous colitis, fever, abdominal pain, dehydration and disturbances in electrolytes, megacolon, peritonitis, and perforation and/or rupture of the colon.

8. The method of claim 1, wherein the protection of the patient's microbiome comprises maintenance of a normal intestinal microbiota selected from a healthy microbiota balance and a healthy ratio or distribution.

\* \* \* \* \*

SEQUENCE LISTING

```
<160> NUMBER OF SEQ ID NOS: 2

<210> SEQ ID NO 1
<211> LENGTH: 264
<212> TYPE: PRT
<213> ORGANISM: Artificial Sequence
<220> FEATURE:
<223> OTHER INFORMATION: Synthetic sequence

<400> SEQUENCE: 1

Thr Glu Met Lys Asp Asp Phe Ala Lys Leu Glu Glu Gln Phe Asp Ala
1               5                   10                  15

Lys Leu Gly Ile Phe Ala Leu Asp Thr Gly Thr Asn Arg Thr Val Ala
            20                  25                  30

Tyr Arg Pro Asp Glu Arg Phe Ala Phe Ala Ser Thr Ile Lys Ala Leu
        35                  40                  45

Thr Val Gly Val Leu Leu Gln Gln Lys Ser Ile Glu Asp Leu Asn Gln
    50                  55                  60

Arg Ile Thr Tyr Thr Arg Asp Asp Leu Val Asn Tyr Asn Pro Ile Thr
65                  70                  75                  80

Glu Lys His Val Asp Thr Gly Met Thr Leu Lys Glu Leu Ala Asp Ala
                85                  90                  95

Ser Leu Arg Tyr Ser Asp Asn Ala Ala Gln Asn Leu Ile Leu Lys Gln
            100                 105                 110

Ile Gly Gly Pro Glu Ser Leu Lys Lys Glu Leu Arg Lys Ile Gly Asp
        115                 120                 125

Glu Val Thr Asn Pro Glu Arg Phe Glu Pro Glu Leu Asn Glu Val Asn
    130                 135                 140

Pro Gly Glu Thr Gln Asp Thr Ser Thr Ala Arg Ala Leu Val Thr Ser
```

```
                145                 150                 155                 160
Leu Arg Ala Phe Ala Leu Glu Asp Lys Leu Pro Ser Glu Lys Arg Glu
                165                 170                 175

Leu Leu Ile Asp Trp Met Lys Arg Asn Thr Thr Gly Asp Ala Leu Ile
            180                 185                 190

Arg Ala Gly Val Pro Asp Gly Trp Glu Val Ala Asp Lys Thr Gly Ala
        195                 200                 205

Ala Ser Tyr Gly Thr Arg Asn Asp Ile Ala Ile Ile Trp Pro Pro Lys
    210                 215                 220

Gly Asp Pro Val Val Leu Ala Val Leu Ser Ser Arg Asp Lys Lys Asp
225                 230                 235                 240

Ala Lys Tyr Asp Asn Lys Leu Ile Ala Glu Ala Thr Lys Val Val Met
                245                 250                 255

Lys Ala Leu Asn Met Asn Gly Lys
                260

<210> SEQ ID NO 2
<211> LENGTH: 795
<212> TYPE: DNA
<213> ORGANISM: Artificial Sequence
<220> FEATURE:
<223> OTHER INFORMATION: Synthetic sequence

<400> SEQUENCE: 2
atgactgaga tgaaagatga ttttgcgaag ctggaagaac agtttgacgc aaaattgggc        60
attttcgcgt tggacacggg tacgaatcgt acggttgcct accgtccgga cgagcgcttc       120
gccttcgcga gcacgatcaa agccctgacc gtcggcgtgc tgctccagca aaagagcatc       180
gaggacctga accagcgcat tacctacacc cgtgatgatc tggtgaacta taatccgatc       240
accgagaaac acgttgatac cggtatgacc ctgaaagaac tggcagatgc aagcctgcgc       300
tacagcgata acgcggctca gaatctgatt ctgaagcaaa tcggtggtcc ggagagcttg       360
aagaaagaac tgcgtaaaat cggcgatgaa gtcactaatc cggagcgttt tgagccggag       420
ctgaacgaag tgaatccggg tgaaacgcaa gacacgagca ccgcgcgtgc gcttgtcacc       480
tccctgcgcg ctttcgcact ggaagataag ctgccgtcgg agaaacgcga gctgctgatc       540
gactggatga agcgcaatac gaccggcgac gcgctgattc gtgcgggcgt tccggacggt       600
tgggaagtgg ctgacaagac cggtgcggcg agctacggca cccgtaacga tatcgcgatc       660
atttggccac ctaaaggtga cccggtcgtg ctggccgtac tgagcagccg tgacaagaaa       720
gacgcaaagt atgataacaa gctgattgca gaggcgacca agttgttat gaaggcactg       780 aacatgaatg gtaag                                                       795
```